US010243153B2

(12) United States Patent
Ise

(10) Patent No.: US 10,243,153 B2
(45) Date of Patent: Mar. 26, 2019

(54) MATERIAL FOR ORGANIC ELECTROLUMINESCENCE DEVICE AND ORGANIC ELECTROLUMINESCENCE DEVICE

(71) Applicant: UDC IRELAND LIMITED, Dublin (IE)

(72) Inventor: Toshihiro Ise, Kanagawa (JP)

(73) Assignee: UDC IRELAND LIMITED, Dublin (IE)

( * ) Notice: Subject to any disclaimer, the term of this patent is extended or adjusted under 35 U.S.C. 154(b) by 271 days.

(21) Appl. No.: 15/060,725

(22) Filed: Mar. 4, 2016

(65) Prior Publication Data

US 2016/0254462 A1 Sep. 1, 2016

Related U.S. Application Data

(63) Continuation of application No. 12/872,775, filed on Aug. 31, 2010, now Pat. No. 9,318,714.

(30) Foreign Application Priority Data

Aug. 31, 2009 (JP) ................................ 2009-201159
Sep. 28, 2009 (JP) ................................ 2009-223453
Apr. 23, 2010 (JP) ................................ 2010-100396

(51) Int. Cl.

| | |
|---|---|
| ***C09K 11/06*** | (2006.01) |
| ***H01L 51/54*** | (2006.01) |
| ***H01L 51/00*** | (2006.01) |
| ***C07F 15/00*** | (2006.01) |
| ***C07D 209/86*** | (2006.01) |
| *H01L 51/50* | (2006.01) |
| *H01L 51/52* | (2006.01) |
| *H01L 51/56* | (2006.01) |

(52) U.S. Cl.

CPC ........ *H01L 51/0085* (2013.01); *C07D 209/86* (2013.01); *C07F 15/0033* (2013.01); *C09K 11/06* (2013.01); *C09K 2211/1007* (2013.01); *C09K 2211/1011* (2013.01); *C09K 2211/1029* (2013.01); *C09K 2211/1044* (2013.01); *C09K 2211/185* (2013.01); *H01L 51/0072* (2013.01); *H01L 51/5016* (2013.01); *H01L 51/5024* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5268* (2013.01); *H01L 51/56* (2013.01)

(58) Field of Classification Search

None

See application file for complete search history.

(56) References Cited

U.S. PATENT DOCUMENTS

| | | | | |
|---|---|---|---|---|
| 9,318,714 | B2 * | 4/2016 | Ise | ...................... H01L 51/0085 |
| 2001/0019782 | A1 | 9/2001 | Igarashi et al. | |
| 2001/0050532 | A1 | 12/2001 | Eida et al. | |
| 2002/0033910 | A1 | 3/2002 | Ohnishi et al. | |
| 2003/0124764 | A1 | 7/2003 | Yamazaki et al. | |
| 2005/0003233 | A1 | 1/2005 | Igarashi et al. | |
| 2005/0106322 | A1 | 5/2005 | Yamazaki et al. | |
| 2005/0164030 | A1 | 7/2005 | Knowles et al. | |
| 2007/0190359 | A1 | 8/2007 | Knowles et al. | |
| 2007/0207341 | A1 | 9/2007 | Iida et al. | |
| 2007/0231602 | A1 | 10/2007 | Igarashi et al. | |
| 2008/0081115 | A1 | 4/2008 | Yamazaki et al. | |
| 2008/0297033 | A1 | 12/2008 | Knowles et al. | |
| 2008/0319239 | A1 | 12/2008 | Buesing | |
| 2009/0066223 | A1 | 3/2009 | Yabe et al. | |
| 2009/0284134 | A1 | 11/2009 | Iida et al. | |
| 2010/0141125 | A1 | 6/2010 | Otsu et al. | |
| 2010/0141126 | A1 | 6/2010 | Otsu et al. | |
| 2010/0171113 | A1 | 7/2010 | Igarashi et al. | |
| 2010/0174069 | A1 | 7/2010 | Igarashi et al. | |
| 2010/0174070 | A1 | 7/2010 | Igarashi et al. | |
| 2010/0174071 | A1 | 7/2010 | Igarashi et al. | |

FOREIGN PATENT DOCUMENTS

| | | |
|---|---|---|
| JP | 11-224781 | 8/1999 |
| JP | 2001-247859 | 9/2001 |
| JP | 2003-313654 | 11/2003 |
| JP | 2005/011733 | 1/2005 |
| JP | 2006-066366 | 3/2006 |
| JP | 2006/210095 | 8/2006 |
| JP | 2006-257409 | 9/2006 |
| JP | 2006-278067 | 10/2006 |
| JP | 2006/294534 | 10/2006 |
| JP | 2007/087620 | 4/2007 |
| JP | 2007-123392 | 5/2007 |
| JP | 2007-522126 | 8/2007 |
| JP | 2008-115131 | 5/2008 |
| JP | 2008-192433 | 8/2008 |
| JP | 2009-102533 | 5/2009 |
| JP | 2009-102656 | 5/2009 |
| JP | 2009-146691 | 7/2009 |
| WO | 01/58221 | 8/2001 |

(Continued)

OTHER PUBLICATIONS

Notification of Reasons for Refusal dated Nov. 25, 2009 issued by the Japan Patent Office in counterpart Japanese Application No. 2009-223453.

(Continued)

*Primary Examiner* — Marie R. Yamnitzky
(74) *Attorney, Agent, or Firm* — Riverside Law LLP

(57) ABSTRACT

A material for an organic electroluminescence device, includes: an organic material that is to be provided for a film formation of any of at least one organic layer included in the organic electroluminescence device, the organic material having a water content before the film formation, as measured by the Karl Fischer method, of 100 ppm or more and not more than 1,000 ppm.

9 Claims, 2 Drawing Sheets

(56) References Cited

FOREIGN PATENT DOCUMENTS

| | | |
|---|---|---|
| WO | 2007/063760 | 6/2007 |
| WO | 2008/140114 | 11/2008 |
| WO | 2008140115 | 11/2008 |

OTHER PUBLICATIONS

Notification of Reasons for Refusal dated Jun. 22, 2010 issued by the Japan Patent Office in counterpart Japanese Application No. 2010-100396.

* cited by examiner

MATERIAL FOR ORGANIC ELECTROLUMINESCENCE DEVICE AND ORGANIC ELECTROLUMINESCENCE DEVICE

CROSS-REFERENCE TO RELATED APPLICATIONS

The present application is a continuation of, and claims priority to, U.S. patent application Ser. No. 12/872,775, filed on Aug. 31, 2010, now allowed, which claims priority to Japanese Application Nos. JP 2009-201159, filed Aug. 31, 2009, JP 2009-223453, filed Sep. 28, 2009, and JP 2010-100396, filed Apr. 23, 2010, all of which applications are incorporated by reference herein in their entireties.

BACKGROUND OF THE INVENTION

1. Field of the Invention

The present invention relates to a material for organic electroluminescence device and an organic electroluminescence device (hereinafter also referred to as "device" or "organic EL device"). The invention relates to a technology capable of reducing a rate of occurrence of short-circuit device in the manufacture and enhancing manufacturing yields and a technology capable of enhancing storage stability of the device.

2. Description of the Related Art

In recent years, in view of the fact that light emission with a high brightness is obtainable through low-voltage driving, an organic electroluminescence device has been actively researched and developed. In general, the organic electroluminescence device is constituted of an organic layer including a light emitting layer and a pair of electrodes interposing this light emitting layer therebetween, and energy of an exciton generated through recombination of an electron injected from a cathode and a hole injected from an anode is utilized for the light emission.

In the organic electroluminescence device, an improvement of efficiency of the device is being advanced by using a phosphorescent material. As the phosphorescent material, there is known an iridium complex, a platinum complex or the like, which is capable of undergoing blue, green or red light emission. For example, US-A-2007/0190359 and US-A-2008/0297033 disclose an iridium complex of a ligand having a condensed ring structure.

The organic electroluminescence device is required to have high durability such that it endures long-term light emission. However, it is well known that penetration of moisture into the device generates a dark spot, thereby lowering the durability. It may be considered that this is caused due to the fact that a water molecule accelerates chemical decomposition of a material, or accelerates separation between an organic layer and an electrode interface.

In response to this, there have been made various countermeasures for the purpose of preventing a lowering of durability to be caused due to the penetration of moisture; and there have been disclosed a reduction of the water content in a thin film due to dehydration after film formation (see, for example, WO 01/058221); protection from the penetration of moisture by a sealing structure (see, for example, JP-A-2007-87620, JP-A-2006-294534 and JP-A-2006-278067); utilization of a moisture absorbing material or a moisture capturing material (see, for example, JP-A-2006-66366 and JP-A-2006-210095); and the like.

Also, it is disclosed that a heat treatment is carried out in vacuo during the film formation, thereby removing moisture (see, for example, JP-A-2003-313654).

Also, it is disclosed that in the case where a layer is formed by a wet film formation method, moisture contained in a composition for organic electroluminescence device is decreased as far as possible such that the moisture does not remain in the film after drying, thereby suppressing a lowering of characteristics of the device (see, for example, JP-A-2009-102656).

On the other hand, it is well known that inclusion of fine dusts into a device causes an electrical short circuit of the device, resulting in a lowering of manufacturing yields. As to a method of preventing the short circuit to be caused due to the inclusion of fine dusts, it is proposed that a flattened layer is provided between an anode layer and an organic layer (see, for example, JP-A-11-224781). However, according to this method, occurrence of a defective of the device to be caused due to the fine dusts in the organic layer cannot be avoided.

Also, it is proposed that a relative humidity at the time of film formation by a wet film formation method is regulated to 0.01 ppm or more, thereby suppressing the generation of static electricity during the film formation (see, for example, JP-A-2009-146691).

Also, it is proposed that a relative humidity in a pretreatment step of vapor deposition is regulated to 0.01 ppm or more, thereby making it easy to control the circumstances constant and making it possible to stably manufacture a device (see, for example, JP-A-2008-192433).

SUMMARY OF THE INVENTION

An object of the invention is to provide a material for organic electroluminescence device capable of obtaining an organic electroluminescence device with excellent light emitting characteristics and capable of reducing the number of short-circuit devices; and an organic electroluminescence device using the subject material for organic electroluminescence device.

Also, another object of the invention is to provide a composition useful for organic electroluminescence devices and a light emitting layer. Then, a still another object of the invention is to provide a light emission apparatus and an illumination apparatus each of which includes an organic electroluminescence device.

As disclosed in WO 01/058221 and JP-A-2009-102656 and the like, it is known that the inclusion of even a slight amount of moisture is not preferable for the durability of the device. In an embodiment according to the invention, in which a material containing moisture in an amount within a specified range is used for the material for organic electroluminescence device, in the light of its technical knowledge, it could not be expected that such an embodiment is effective for the manufacture of a device or an enhancement of characteristics.

However, as a result of extensive and intensive investigations made by the present inventor, it has been found that by using, as an organic material to be provided for film formation of any one of layers of at least one organic layer included in an organic electroluminescence device, a material for organic electroluminescence device having a water content before film formation, as measured by the Karl Fischer method, of 100 ppm or more and not more than 1,000 ppm, in an organic electroluminescence device including a layer obtained by film formation of such a material, a probability of occurrence of short-circuit device can be lowered, thereby enhancing the yields without lowering driving durability. The foregoing water content refers to a water content before film formation. Also, at the same time, it has been found that the use of such a material is also effective for suppressing occurrence of cloudiness of the device at the time of device storage. Though mechanisms of these effects have not been elucidated yet, it may be presumed that electrification is suppressed by adsorbed water on the surface of a solid so that attachment of fine dusts to be caused due to the electrification is suppressed. As a result, it may be considered that the inclusion of fine dusts into the device can be suppressed, thereby bringing an effect for reducing an short-circuit device or an enhancement of storage stability.

It may be considered that the water content of the iridium complexes synthesized by the methods disclosed in US-A-2007/0190359 and US-A-2008/0297033 is less than 5 ppm.

That is, the invention has been achieved by the following means.

[1] A material for an organic electroluminescence device, comprising:

an organic material that is to be provided for a film formation of any of at least one organic layer included in the organic electroluminescence device, the organic material having a water content before the film formation, as measured by the Karl Fischer method, of 100 ppm or more and not more than 1,000 ppm.

[2] The material for an organic electroluminescence as described in [1] above, wherein the organic material is an organometallic compound having a carbon-metal bond.

[3] The material for an organic electroluminescence device as described in [2] above, wherein the organometallic compound having a carbon-metal bond is an iridium complex material represented by the following formula (E-1):

(E-1)

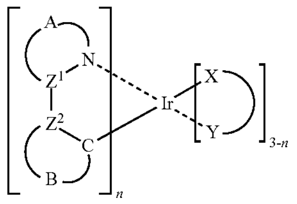

in the formula (E-1), each of $Z^1$ and $Z^2$ independently represents a carbon atom or a nitrogen atom;

A represents an atomic group for forming a 5- or 6-membered aromatic ring together with $Z^1$ and N;

B represents an atomic group for forming a 5- or 6-membered aromatic ring together with $Z^2$ and C;

though each of a line connecting $Z^1$ and N, a line connecting $Z^1$ and the atomic group A, a line connecting N and the atomic group A, a line connecting $Z^2$ and C, a line connecting $Z^2$ and the atomic group B and a line connecting C and the atomic group B is expressed by a single line, each may be either a single bond or a double bond irrespective of a bonding species;

X—Y represents a monoanionic bidentate ligand represented by the following formula (I-1), (I-2) or (I-3); and n represents an integer of from 1 to 3:

(I-1)

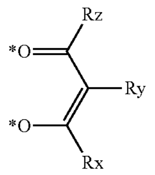

(I-2)

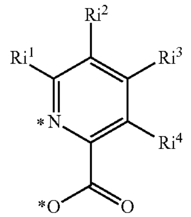

(I-3)

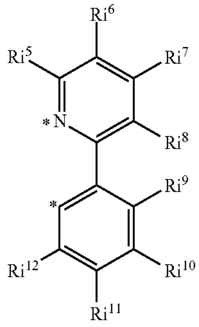

in the formula (I-1), each of Rx and Rz independently represents an alkyl group, a perfluoroalkyl group or an aryl group; and Ry represents a hydrogen atom, an alkyl group, a perfluoroalkyl group or an aryl group, in the formula (I-2), each of $Ri^1$ to $Ri^4$ independently represents a hydrogen atom, an alkyl group, a perfluoroalkyl group, an aryl group, an alkoxy group, an aryloxy group, a dialkylamino group, a diarylamino group, a cyano group, a fluorine atom, a trialkylsilyl group, a triarylsilyl group, an alkyldiarylsilyl group, a dialkylarylsilyl group, a heterocyclic group or a heterocyclic oxy group; and adjacent substituents among $Ri^1$ to $Ri^4$ may be connected to each other, and in the formula (I-3), each of $Ri^5$ to $Ri^{12}$ independently represents a hydrogen atom, an alkyl group, a perfluoroalkyl group, an aryl group, an alkoxy group, an aryloxy group, a dialkylamino group, a diarylamino group, a cyano group, a fluorine atom, a trialkylsilyl group, a triarylsilyl group, an alkyldiarylsilyl group, a dialkylarylsilyl group, a heterocyclic group or a heterocyclic oxy group; and adjacent substituents among $Ri^5$ to $Ri^8$, adjacent substituents among $Ri^9$ to $Ri^{12}$, and $Ri^8$ and $Ri^9$ may be each connected to each other.

[4] The material for an organic electroluminescence device as described in [3] above, wherein the iridium complex material represented by the formula (E-1) is represented by the following formula (E-2):

(E-2)

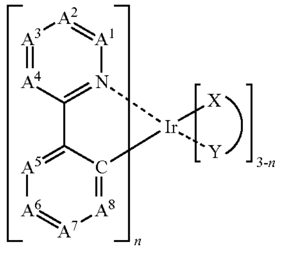

in the formula (E-2), each of $A^1$ to $A^8$ independently represents a nitrogen atom or C—R;

R represents a hydrogen atom, an alkyl group, an aryl group, an aromatic heterocyclic group, a cyano group, a silyl group, an amino group or a fluorine atom;

X—Y is synonymous with X—Y in the formula (E-1); and n represents an integer of from 1 to 3.

[5] The material for an organic electroluminescence device as described in [3] above, wherein the iridium complex material represented by the formula (E-1) is represented by the following formula (E-3):

(E-3)

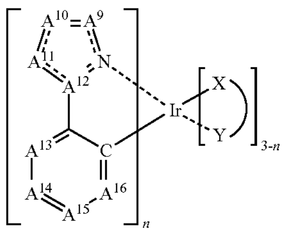

in the formula (E-3), each of $A^9$ to $A^{11}$ and $A^{13}$ to $A^{16}$ independently represents C—R, N or N—R';

$A^{12}$ represents a carbon atom or a nitrogen atom;

R represents a hydrogen atom, an alkyl group, an aryl group, an aromatic heterocyclic group, a cyano group, a silyl group, an amino group or a fluorine atom;

R' represents a hydrogen atom, an alkyl group or an aryl group;

X—Y is synonymous with X—Y in the formula (E-1); and n represents an integer of from 1 to 3.

[6] The material for an organic electroluminescence device as described in [5] above, wherein the iridium complex material represented by the formula (E-3) is represented by the following formula (E-4):

(E-4)

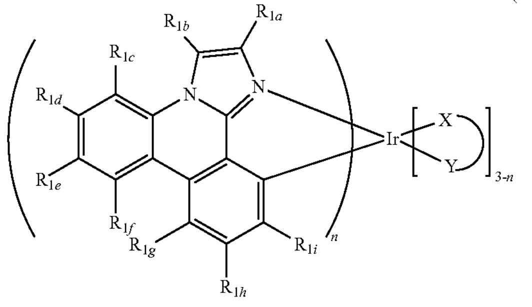

in the formula (E-4), each of $R_{1a}$ to $R_{1i}$ independently represents a hydrogen atom, an alkyl group, an aryl group, an aromatic heterocyclic group, a cyano group, a silyl group, an amino group or a fluorine atom;

X—Y is synonymous with X—Y in the formula (E-1); and n represents an integer of from 1 to 3.

[7] The material for an organic electroluminescence device as described in [6] above, wherein in the formula (E-4), n is 3.

[8] The material for an organic electroluminescence device as described in [2] above, wherein the organometallic compound having a carbon-metal bond is an iridium complex material represented by the following formula (PQ-1):

(PQ-1)

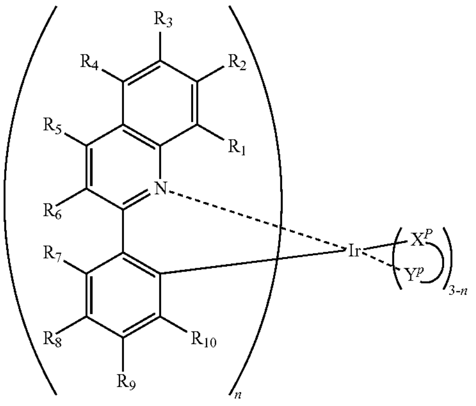

in the formula (PQ-1), each of $R_1$ to $R_{10}$ independently represents a hydrogen atom, an alkyl group, an aryl group, an aromatic heterocyclic group, a cyano group, a silyl group, an amino group or a fluorine atom;

$R_1$ to $R_{10}$ may be bonded to each other to form a ring, if possible;

$X^P$—$Y^P$ represents a monoanionic bidentate ligand represented by the following formula (I-1), (I-2) or (I-3); and n represents an integer of from 1 to 3:

(I-1)

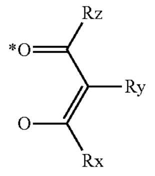

(I-2)

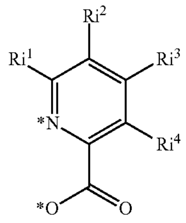

-continued (I-3)

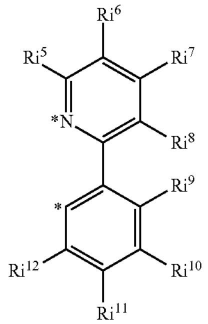

in the formula (I-1), each of Rx and Rz independently represents an alkyl group, a perfluoroalkyl group or an aryl group; and Ry represents a hydrogen atom, an alkyl group, a perfluoroalkyl group or an aryl group, in the formula (I-2), each of $Ri^1$ to $Ri^4$ independently represents a hydrogen atom, an alkyl group, a perfluoroalkyl group, an aryl group, an alkoxy group, an aryloxy group, a dialkylamino group, a diarylamino group, a cyano group, a fluorine atom, a trialkylsilyl group, a triarylsilyl group, an alkyldiarylsilyl group, a dialkylarylsilyl group, a heterocyclic group or a heterocyclic oxy group; and adjacent substituents among $Ri^1$ to $Ri^4$ may be connected to each other, and in the formula (I-3), each of $Ri^5$ to $Ri^{12}$ independently represents a hydrogen atom, an alkyl group, a perfluoroalkyl group, an aryl group, an alkoxy group, an aryloxy group, a dialkylamino group, a diarylamino group, a cyano group, a fluorine atom, a trialkylsilyl group, a triarylsilyl group, an alkyldiarylsilyl group, a dialkylarylsilyl group, a heterocyclic group or a heterocyclic oxy group; and adjacent substituents among $Ri^5$ to $Ri^8$, adjacent substituents among $Ri^9$ to $Ri^{12}$, and $Ri^8$ and $Ri^9$ may be each connected to each other.

[9] The material for an organic electroluminescence device as described in [8] above, wherein in the iridium complex represented by the formula (PQ-1), n is 2; and the monoanionic bidentate ligand represented by $X^P$—$Y^P$ is a ligand represented by the following formula L:

Formula L

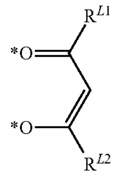

in the formula L, each of $R^{L1}$ and $R^{L2}$ independently represents an alkyl group having from 1 to 5 carbon atoms or a phenyl group which may have a substituent selected from the substituent group T2 consisting of an alkyl group having from 1 to 6 carbon atoms, an alkenyl group having from 2 to 6 carbon atoms, a phenyl group, an aromatic heterocyclic group having from 5 to 10 carbon atoms, an alkoxy group having from 1 to 4 carbon atoms, a phenoxy group, a fluorine atom, a silyl group, an amino group, a cyano group and a group composed of a combination of these groups; and plural substituents selected from the substituent group T2 may be connected to each other to form an aromatic hydrocarbon ring.

[10] A light emitting layer, which is prepared using the material for an organic electroluminescence device as described in any one of [1] to [9] above.

[11] The light emitting layer as described in [10] above, further comprising:

a compound represented by the following formula (4-1) or (4-2):

Formula (4-1)

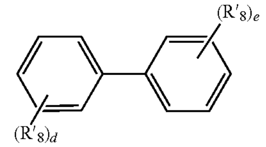

Formula (4-2)

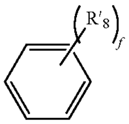

in the formulae (4-1) and (4-2), each of d and e independently represents an integer of from 0 to 3, and at least one of d and e is 1 or more;

f represents an integer of from 1 to 4;

$R'_8$ represents an alkyl group, an aryl group, a heteroaryl group, a fluorine atom, a cyano group, an alkoxy group, an aryloxy group, an amino group or a silyl group, and when plural $R'_8$s are present, each $R'_8$ may be the same as or different from every other $R'_8$; and at least one of $R'_8$s represents a group represented by the following formula (5):

(5)

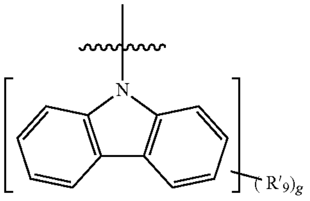

in the formula (5), each of $R'_9$s independently represents an alkyl group, an aryl group, a heteroaryl group, a fluorine atom, a cyano group, an alkoxy group, an aryloxy group, an amino group or a silyl group; and g represents an integer of from 0 to 8.

[12] A composition, comprising:

the material for an organic electroluminescence device as described in any one of [1] to [9] above.

[13] The composition as described in [12] above, further comprising:

a compound represented by the following formula (4-1) or (4-2):

Formula (4-1)

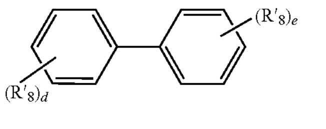

-continued

Formula (4-2)

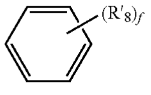

in the formulae (4-1) and (4-2), each of d and e independently represents an integer of from 0 to 3, and at least one of d and e is 1 or more;

f represents an integer of from 1 to 4;

$R'_8$ represents an alkyl group, an aryl group, a heteroaryl group, a fluorine atom, a cyano group, an alkoxy group, an aryloxy group, an amino group or a silyl group, and when plural $R'_8$s are present, each $R'_8$ may be the same as or different from every other $R'_8$; and at least one of $R'_8$s represents a group represented by the following formula (5):

(5)

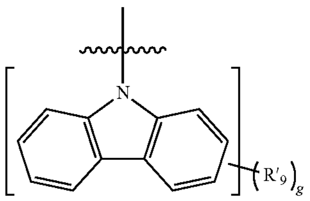

in the formula (5), each of $R'_9$s independently represents an alkyl group, an aryl group, a heteroaryl group, a fluorine atom, a cyano group, an alkoxy group, an aryloxy group, an amino group or a silyl group; and g represents an integer of from 0 to 8.

[14] An organic electroluminescence device, comprising:

a substrate having thereon a pair of electrodes; and at least one organic layer including a light emitting layer between the pair of electrodes, wherein the material for an organic electroluminescence device as described in any one of [1] to [9] above is used in at least one layer of the at least one organic layer.

[15] A method for manufacturing an organic electroluminescence device, comprising:

using the material for an organic electroluminescence device as described in any one of [1] to [9] above.

[16] A method for reducing a rate of occurrence of short-circuit device, comprising:

using the material for an organic electroluminescence device as described in any one of [1] to [9] above.

[17] A display apparatus, comprising:

the material for an organic electroluminescence device as described in any one of [1] to [9] above.

[18] An illumination apparatus, comprising:

the material for an organic electroluminescence device as described in any one of [1] to [9] above.

DETAILED DESCRIPTION OF THE INVENTION

Figure 1:
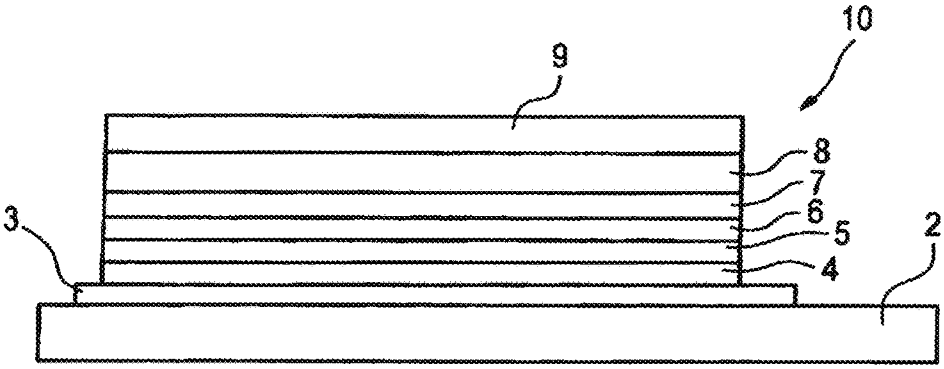
FIG. 1 is a diagrammatic view showing an example of a layer configuration of an organic electroluminescence device according to the invention.

In the invention, a substituent group A and a substituent group B are defined as follows.

(Substituent Group A)

Examples of the substituent group A include an alkyl group (preferably an alkyl group having from 1 to 30 carbon atoms, more preferably an alkyl group having from 1 to 20 carbon atoms, and especially preferably an alkyl group having from 1 to 10 carbon atoms; for example, methyl, ethyl, isopropyl, tert-butyl, n-octyl, n-decyl, n-hexadecyl, cyclopropyl, cyclopentyl, cyclohexyl, etc.), a perfluoroalkyl group (preferably a perfluoroalkyl group having from 1 to 10 carbon atoms, more preferably a perfluoroalkyl group having from 1 to 5 carbon atoms, and especially preferably a perfluoroalkyl group having from 1 to 3 carbon atoms; for example, trifluoromethyl, pentafluoroethyl, etc.), an alkenyl group (preferably an alkenyl group having from 2 to 30 carbon atoms, more preferably an alkenyl group having from 2 to 20 carbon atoms, and especially preferably an alkenyl group having from 2 to 10 carbon atoms; for example, vinyl, allyl, 2-butenyl, 3-pentenyl, etc.), an alkynyl group (preferably an alkynyl group having from 2 to 30 carbon atoms, more preferably an alkynyl group having from 2 to 20 carbon atoms, and especially preferably an alkynyl group having from 2 to 10 carbon atoms; for example, propargyl, 3-pentynyl, etc.), an aryl group (preferably an aryl group having from 6 to 30 carbon atoms, more preferably an aryl group having from 6 to 20 carbon atoms, and especially preferably from 6 to 12 carbon atoms; for example, phenyl, p-methylphenyl, naphthyl, anthranyl, etc.), an amino group (preferably an amino group having from 0 to 30 carbon atoms, more preferably an amino group having from 0 to 20 carbon atoms, and especially preferably an amino group having from 0 to 10 carbon atoms; for example, amino, methylamino, dimethylamino, diethylamino, dibenzylamino, diphenylamino, ditolylamino, etc.), an alkoxy group (preferably an alkoxy group having from 1 to 30 carbon atoms, more preferably an alkoxy group having from 1 to 20 carbon atoms, and especially preferably an alkoxy group having from 1 to 10 carbon atoms; for example, methoxy, ethoxy, butoxy, 2-ethylhexyloxy, etc.), an aryloxy group (preferably an aryloxy group having from 6 to 30 carbon atoms, an aryloxy group having from 6 to 20 carbon atoms, and especially preferably an aryloxy group having from 6 to 12 carbon atoms; for example, phenyloxy, 1-naphthyloxy, 2-naphthyloxy, etc.), a heterocyclic oxy group (preferably a heterocyclic oxy group having from 1 to 30 carbon atoms, more preferably a heterocyclic oxy group having from 1 to 20 carbon atoms, and especially preferably a heterocyclic oxy group having from 1 to 12 carbon atoms; for example, pyridyloxy, pyrazyloxy, pyrimidyloxy, quinolyloxy, etc.), an acyl group (preferably an acyl group having from 1 to 30 carbon atoms, more preferably an acyl group having from 1 to 20 carbon atoms, and especially preferably an acyl group having from 1 to 12 carbon atoms; for example, acetyl, benzoyl, formyl, pivaloyl, etc.), an alkoxycarbonyl group (preferably an alkoxycarbonyl group having from 2 to 30 carbon atoms, more preferably an alkoxycarbonyl group having from 2 to 20 carbon atoms, and especially preferably an alkoxycarbonyl group having from 2 to 12 carbon atoms; for example, methoxycarbonyl, ethoxycarbonyl, etc.), an aryloxycarbonyl group (preferably an aryloxycarbonyl group having from 7 to 30 carbon atoms, more preferably an aryloxycarbonyl group having from 7 to 20 carbon atoms, and especially preferably an aryloxycarbonyl group having from 7 to 12 carbon atoms; for example, phenyloxycarbonyl, etc.), an acyloxy group (preferably an acyloxy group having from 2 to 30 carbon atoms, more preferably an acyloxy group having from 2 to 20 carbon atoms, and especially preferably an acyloxy group having from 2 to 10 carbon atoms; for example, acetoxy, benzoyloxy, etc.), an acylamino group (preferably an acylamino group having from 2 to 30 carbon atoms, more preferably an acylamino group having from 2 to 20 carbon atoms, and especially preferably an acylamino group having from 2 to 10 carbon atoms; for example, acetylamino, benzoylamino, etc.), an alkoxycarbonylamino group (preferably an alkoxycarbonylamino group having from 2 to 30 carbon atoms, more preferably an alkoxycarbonylamino group having from 2 to 20 carbon atoms, and especially preferably an alkoxycarbonylamino group having from 2 to 12 carbon atoms; for example, methoxycarbonylamino, etc.), an aryloxycarbonylamino group (preferably an aryloxycarbonylamino group having from 7 to 30 carbon atoms, more preferably an aryloxycarbonylamino group having from 7 to 20 carbon atoms, and especially preferably an aryloxycarbonylamino group having from 7 to 12 carbon atoms; for example, phenyloxycarbonylamino, etc.), a sulfonylamino group (preferably a sulfonylamino group having from 1 to 30 carbon atoms, more preferably a sulfonylamino group having from 1 to 20 carbon atoms, and especially preferably a sulfonylamino group having from 1 to 12 carbon atoms; for example, methanesulfonylamino, benzenesulfonylamino, etc.), a sulfamoyl group (preferably a sulfamoyl group having from 0 to 30 carbon atoms, more preferably a sulfamoyl group having from 0 to 20 carbon atoms, and especially preferably a sulfamoyl group having from 0 to 12 carbon atoms; for example, sulfamoyl, methylsulfamoyl, dimethylsulfamoyl, phenylsulfamoyl, etc.), a carbamoyl group (preferably a carbamoyl group having from 1 to 30 carbon atoms, more preferably a carbamoyl group having from 1 to 20 carbon atoms, and especially preferably a carbamoyl group having from 1 to 12 carbon atoms; for example, carbamoyl, methylcarbamoyl, diethylcarbamoyl, phenylcarbamoyl, etc.), an alkylthio group (preferably an alkylthio group having from 1 to 30 carbon atoms, more preferably an alkylthio group having from 1 to 20 carbon atoms, and especially preferably an alkylthio group having from 1 to 12 carbon atoms; for example, methylthio, ethylthio, etc.), an arylthio group (preferably an arylthio group having from 6 to 30 carbon atoms, more preferably an arylthio group having from 6 to 20 carbon atoms, and especially preferably an arylthio group having from 6 to 12 carbon atoms; for example, phenylthio, etc.), a heterocyclic thio group (preferably a heterocyclic thio group having from 1 to 30 carbon atoms, more preferably a heterocyclic thio group having from 1 to 20 carbon atoms, and especially preferably a heterocyclic thio group having from 1 to 12 carbon atoms; for example, pyridylthio, 2-benzimidazolylthio, 2-benzoxazolylthio, 2-benzothiazolylthio, etc.), a sulfonyl group (preferably a sulfonyl group having from 1 to 30 carbon atoms, more preferably a sulfonyl group having from 1 to 20 carbon atoms, and especially preferably a sulfonyl group having from 1 to 12 carbon atoms; for example, mesyl, tosyl, etc.), a sulfinyl group (preferably a sulfinyl group having from 1 to 30 carbon atoms, more preferably a sulfinyl group having from 1 to 20 carbon atoms, and especially preferably a sulfinyl group having from 1 to 12 carbon atoms; for example, methanesulfinyl, benzenesulfinyl, etc.), a ureido group (preferably a ureido group having from 1 to 30 carbon atoms, more preferably a ureido group having from 1 to 20 carbon atoms, and especially preferably a ureido group having from 1 to 12 carbon atoms; for example, ureido, methylureido, phenylureido, etc.), a phosphoric acid amide group (preferably a phosphoric acid amide group having from 1 to 30 carbon atoms, more preferably a phosphoric acid amide group having from 1 to 20 carbon atoms, and especially preferably a phosphoric acid amide group having from 1 to 12 carbon atoms; for example, diethylphosphoric acid amide, phenylphosphoric acid amide, etc.), a hydroxyl group, a mercapto group, a halogen atom (for example, a fluorine atom, a chlorine atom, a bromine atom, an iodine atom), a cyano group, a sulfo group, a carboxyl group, a nitro group, a hydroxamic acid group, a sulfino group, a hydrazino group, an imino group, a heterocyclic group (inclusive of an aromatic heterocyclic group) (preferably a heterocyclic group having from 1 to 30 carbon atoms, and more preferably a heterocyclic group having from 1 to 12 carbon atoms; the hetero atom as referred to herein means an atom other than a carbon atom or a hydrogen atom, examples thereof include a nitrogen atom, an oxygen atom, a sulfur atom, phosphorus atom, a silicon atom, a selenium atom and a tellurium atom, and of these, an oxygen atom, a nitrogen atom and a sulfur atom are preferable, with an oxygen atom and a nitrogen atom being more preferable; and specific examples of the heterocyclic group include pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, carbazolyl, azepinyl, silolyl, etc.), a silyl group (preferably a silyl group having from 3 to 40 carbon atoms, more preferably a silyl group having from 3 to 30 carbon atoms, and especially preferably a silyl group having from 3 to 24 carbon atoms; for example, trimethylsilyl, triphenylsilyl, etc.), a silyloxy group (preferably a silyloxy group having from 3 to 40 carbon atoms, more preferably a silyloxy group having from 3 to 30 carbon atoms, and especially preferably a silyloxy group having from 3 to 24 carbon atoms; for example, trimethylsilyloxy, triphenylsilyloxy, etc.) and a phosphoryl group (for example, diphenylphosphoryl, dimethylphosphoryl, etc.). Such a substituent may be further substituted. As the further substituent, those described previously in the substituent group A can be exemplified.

(Substituent Group B)

Examples of the substituent group B include an alkyl group (preferably an alkyl group having from 1 to 30 carbon atoms, more preferably an alkyl group having from 1 to 20 carbon atoms, and especially preferably an alkyl group having from 1 to 10 carbon atoms; for example, methyl, ethyl, isopropyl, tert-butyl, n-octyl, n-decyl, n-hexadecyl, cyclopropyl, cyclopentyl, cyclohexyl, etc.), an alkenyl group (preferably an alkenyl group having from 2 to 30 carbon atoms, more preferably an alkenyl group having from 2 to 20 carbon atoms, and especially preferably an alkenyl group having from 2 to 10 carbon atoms; for example, vinyl, allyl, 2-butenyl, 3-pentenyl, etc.), an alkynyl group (preferably an alkynyl group having from 2 to 30 carbon atoms, more preferably an alkynyl group having from 2 to 20 carbon atoms, and especially preferably an alkynyl group having from 2 to 10 carbon atoms; for example, propargyl, 3-pentynyl, etc.), an aryl group (preferably an aryl group having from 6 to 30 carbon atoms, more preferably an aryl group having from 6 to 20 carbon atoms, and especially preferably from 6 to 12 carbon atoms; for example, phenyl, p-methylphenyl, naphthyl, anthranyl, etc.), a cyano group and a heterocyclic group (inclusive of an aromatic heterocyclic group) (preferably a heterocyclic group having from 1 to 30 carbon atoms, and more preferably a heterocyclic group having from 1 to 12 carbon atoms; examples of the hetero atom include a nitrogen atom, an oxygen atom, a sulfur atom, phosphorus atom, a silicon atom, a selenium atom and a tellurium atom; and specific examples of the heterocyclic group include pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, carbazolyl, azepinyl, silolyl, etc.). Such a substituent may be further substituted. As the further substituent, those described previously in the substituent group A can be exemplified.

The material for organic electroluminescence device of the invention is an organic material to be provided for film formation of any one of layers of at least one organic layer included in the organic electroluminescence device; and this material is a material for organic electroluminescence device having a water content of a sample (organic material) before film formation, as measured by the Karl Fischer method, in other words, a water content obtained by measuring moisture which has been heated and vaporized from a sample (organic material) in a solid state before film formation by vapor deposition or the like, by the Karl Fischer method, is 100 ppm or more and not more than 1,000 ppm (namely, the water content in 1 kg of the sample (organic material) before film formation is 100 mg or more and not more than 1,000 mg).

By preparing an organic electroluminescence device using the material having a water content falling within the foregoing range, it is possible to reduce a probability of occurrence of short-circuit device, thereby enhancing the yields without lowering durability. Also, it is possible to suppress crystallization of a thin film in the device, thereby enhancing storage durability. It may be considered that this is caused due to the fact that by incorporating a trace amount of moisture, not only dust collection due to electrification of the material can be prevented, but inclusion of fine dusts into the device prepared using this material can be prevented.

Examples of the Karl Fischer method include a method in which by using a Karl Fischer trace moisture meter (CA-200, manufactured by Mitsubishi Chemical Analytech Co., Ltd.), a material for organic electroluminescence device is heated to 140° C. by a water vaporizer (VA-200, manufactured by Mitsubishi Chemical Analytech Co., Ltd.), and vaporized moisture is sent to a titration cell with dry $N_2$ at a flow rate of 250 mL/min, thereby measuring a water content of the material.

When the term "water content" is simply referred to in this application, it means a water content measured by the Karl Fischer method.

The material for organic electroluminescence device of the invention is preferably used for film formation of a light emitting layer, and more preferably used for film formation of a light emitting layer as a light emitting material.

The material for organic electroluminescence device having a water content before film formation of 100 ppm or more and not more than 1,000 ppm according to the invention is preferably an organometallic compound having a carbon-metal bond.

From the viewpoint that larger effects are brought, it is preferable that the organometallic compound having a carbon-metal bond is an iridium complex material represented by the following formula (E-1).

The formula (E-1) is described.

(E-1)

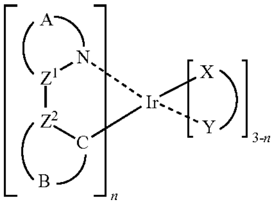

In the formula (E-1), each of $Z^1$ and $Z^2$ independently represents a carbon atom or a nitrogen atom; A represents an atomic group for forming a 5- to 6-membered aromatic ring together with $Z^1$ and N; B represents an atomic group for forming a 5- to 6-membered aromatic ring together with $Z^2$ and C; though each of a line connecting $Z^1$ and N, a line connecting $Z^1$ and the atomic group A, a line connecting N and the atomic group A, a line connecting $Z^2$ and C, a line connecting $Z^2$ and the atomic group B and a line connecting C and the atomic group B is expressed by a single line, each may be either a single bond or a double bond irrespective of a bonding species; X—Y represents a monoanionic bidentate ligand; and n represents an integer of from 1 to 3.

n represents an integer of from 1 to 3. n is preferably 2 or 3, and most preferably 3.

Each of $Z^1$ and $Z^2$ independently represents a carbon atom or a nitrogen atom. For a reason that a device with a high external quantum efficiency is obtained, each of $Z^1$ and $Z^2$ is preferably a carbon atom.

A represents an atomic group for forming a 5- to 6-membered aromatic ring together with $Z^1$ and N. Examples of the 5- to 6-membered aromatic ring containing the atomic group A, $Z^1$ and N include a pyridine ring, a pyrimidine ring, a pyrazine ring, a triazine ring, an imidazole ring, a pyrazole ring, an oxazole ring, a thiazole ring, a triazole ring, an oxadiazole ring and a thiadiazole ring. Such a ring may form a condensed ring together with other ring.

From the viewpoints of stability of the complex, control of light emission wavelength and light emission quantum yield, the 5- to 6-membered aromatic ring formed by the atomic group A, $Z^1$ and N is preferably a pyridine ring, a pyrazine ring, an imidazole ring or a pyrazole ring; more preferably a pyridine ring, an imidazole ring or a pyrazole ring; and further preferably a pyridine ring or an imidazole ring.

The 5- to 6-membered aromatic ring formed by the atomic group A, $Z^1$ and N may have a substituent.

As the substituent which can be substituted on the carbon atom in the 5- to 6-membered aromatic ring formed by the atomic group A, $Z^1$ and N, those described previously in the substituent group A can be exemplified.

The substituent which can be substituted on the carbon atom is preferably an alkyl group, a perfluoroalkyl group, an aryl group, an aromatic heterocyclic group, a dialkylamino group, a diarylamino group, an alkoxy group, a cyano group, a fluorine atom or a cycloalkyl group, and more preferably an alkyl group or an aryl group.

Though the substituent which can be substituted on the carbon atom in the 5- to 6-membered aromatic ring formed by the atomic group A, $Z^1$ and N is properly selected for the purpose of controlling the light emission wavelength or potential, in the case of making the wavelength short, the substituent is preferably an electron donating group, a fluorine atom or an aromatic ring group, and for example, an alkyl group, a dialkylamino group, an alkoxy group, a fluorine atom, an aryl group, an aromatic heterocyclic group and the like are selected. Also, in the case of making the wavelength long, the substituent is preferably an electron withdrawing group, and for example, a cyano group, a perfluoroalkyl group and the like are selected.

At least two of these substituents may be bonded to each other to form a ring; and examples of the ring to be formed include a benzene ring, a pyridine ring, a pyrazine ring, a pyridazine ring, a pyrimidine ring, an imidazole ring, an oxazole ring, a thiazole ring, a pyrazole ring, a thiophene ring and a furan ring, with a benzene ring, a pyridine ring, a pyrazine ring, a pyridazine ring, a pyrimidine ring, an imidazole ring and a pyrazole ring being preferable.

Also, such a substituent may further have a substituent. As the substituent, those described previously in the substituent group A can be exemplified. The substituent is preferably an alkyl group, a perfluoroalkyl group, an aryl group, an aromatic heterocyclic group, a dialkylamino group, a diarylamino group, an alkoxy group, a cyano group, a fluorine atom or a cycloalkyl group; more preferably an alkyl group, an aryl group, a cyano group, a fluorine atom or a cycloalkyl group; and further preferably an alkyl group, a cyano group or a fluorine atom.

As the substituent which can be substituted on the nitrogen atom in the 5- to 6-membered aromatic ring formed by the atomic group A, $Z^1$ and N, those described previously in the substituent group B can be exemplified.

The substituent which can be substituted on the nitrogen atom in the 5- to 6-membered aromatic ring formed by the atomic group A, $Z^1$ and N is preferably an alkyl group, an aryl group or an aromatic heterocyclic group, and from the viewpoint of stability of the complex, the substituent is preferably an alkyl group or an aryl group.

Though the substituent which can be substituted on the nitrogen atom in the 5- to 6-membered aromatic ring formed by the atomic group A, $Z^1$ and N is properly selected for the purpose of controlling the light emission wavelength or potential, in the case of making the wavelength short, the substituent is preferably an electron donating group, a fluorine atom or an aromatic ring group, and for example, an alkyl group, a fluorine atom, an aryl group, an aromatic heterocyclic group and the like are selected. Also, in the case of making the wavelength long, the substituent is preferably an electron withdrawing group, and for example, a cyano group and the like are selected.

The foregoing substituents may be connected to each other to form a condensed ring; and examples of the ring to be formed include a benzene ring, a pyridine ring, a pyrazine ring, a pyridazine ring, a pyrimidine ring, an imidazole ring, an oxazole ring, a thiazole ring, a pyrazole ring, a thiophene ring and a furan ring.

Also, such a substituent may further have a substituent. As the substituent, those described previously in the substituent group A can be exemplified. The substituent is preferably an alkyl group, a perfluoroalkyl group, an aryl group, an aromatic heterocyclic group, a dialkylamino group, a diarylamino group, an alkoxy group, a cyano group, a fluorine atom or a cycloalkyl group; more preferably an alkyl group, an aryl group, a cyano group, a fluorine atom or a cycloalkyl group; and further preferably an alkyl group, a cyano group or a fluorine atom.

B represents an atomic group for forming a 5- to 6-membered aromatic ring together with $Z^2$ and C. Examples of the 5- to 6-membered aromatic ring formed by the atomic group B, $Z^2$ and C include a benzene ring, a pyridine ring, a pyrimidine ring, a pyrazine ring, a pyridazine ring, a triazine ring, an imidazole ring, a pyrazole ring, an oxazole ring, a thiazole ring, a triazole ring, an oxadiazole ring, a thiadiazole ring, a thiophene ring and a furan ring. From the viewpoints of stability of the complex, control of light emission wavelength and light emission quantum yield, the 5- to 6-membered aromatic ring formed by the atomic group B, $Z^2$ and C is preferably a benzene ring, a pyridine ring, a pyrazine ring, an imidazole ring, a pyrazole ring or a thiophene ring; more preferably a benzene ring, a pyridine ring or a pyrazole ring; and further preferably a benzene ring or a pyridine ring.

The 5- to 6-membered aromatic ring formed by the atomic group B, $Z^2$ and C may have a substituent.

As the substituent which can be substituted on the carbon atom in the 5- to 6-membered aromatic ring formed by the atomic group B, $Z^2$ and C, those described previously in the substituent group A can be exemplified.

The substituent which can be substituted on the carbon atom is preferably an alkyl group, a perfluoroalkyl group, an aryl group, an aromatic heterocyclic group, a dialkylamino group, a diarylamino group, an alkoxy group, a cyano group or a fluorine atom.

Though the substituent is properly selected for the purpose of controlling the light emission wavelength or potential, in the case of making the wavelength long, the substituent is preferably an electron donating group or an aromatic ring group, and for example, an alkyl group, a dialkylamino group, an alkoxy group, an aryl group, an aromatic heterocyclic group and the like are selected. Also, in the case of making the wavelength short, the substituent is preferably an electron withdrawing group, and for example, a fluorine atom, a cyano group, a perfluoroalkyl group and the like are selected.

As the substituent which can be substituted on the nitrogen atom in the 5- to 6-membered aromatic ring formed by the atomic group B, $Z^2$ and C, those described previously in the substituent group B can be exemplified.

The substituent which can be substituted on the nitrogen atom is preferably an alkyl group, an aryl group or an aromatic heterocyclic group, and from the viewpoint of stability of the complex, the substituent is preferably an alkyl group or an aryl group.

Though the substituent which can be substituted on the nitrogen atom in the 5- to 6-membered aromatic ring formed by the atomic group B, $Z^2$ and C is properly selected for the purpose of controlling the light emission wavelength or potential, in the case of making the wavelength short, the substituent is preferably an electron donating group, a fluorine atom or an aromatic ring group, and for example, an alkyl group, a fluorine atom, an aryl group, an aromatic heterocyclic group and the like are selected. Also, in the case of making the wavelength long, the substituent is preferably an electron withdrawing group, and for example, a cyano group and the like are selected.

The foregoing substituents may be connected to each other to form a ring; and examples of the ring to be formed include a benzene ring, a pyridine ring, a pyrazine ring, a pyridazine ring, a pyrimidine ring, an imidazole ring, an oxazole ring, a thiazole ring, a pyrazole ring, a thiophene ring, a furan ring and a cyclopentadiene ring (for example, an embodiment as in Illustrative Compound 59).

Also, such a substituent may further have a substituent. As the substituent, those described previously in the substituent group A can be exemplified. The substituent is preferably an alkyl group, a perfluoroalkyl group, an aryl group, an aromatic heterocyclic group, a dialkylamino group, a diarylamino group, an alkoxy group, a cyano group, a fluorine atom or a cycloalkyl group; more preferably an alkyl group, an aryl group, a cyano group, a fluorine atom or a cycloalkyl group; and further preferably an alkyl group, a cyano group or a fluorine atom.

The 5- to 6-membered aromatic ring formed by the atomic group A, $Z^1$ and N and the 5- to 6-membered aromatic ring formed by the atomic group B, $Z^2$ and C may be further bonded to each other via a connecting group, to form a ring.

In the formula (E-1), X—Y represents a monoanionic bidentate ligand. It may be considered that such a ligand does not directly contribute to light emitting characteristics but is able to control the light emitting characteristics of a molecule. The monoanionic bidentate ligand which is used in the light emitting material can be selected from those which are known in the art. Examples of such a monoanionic bidentate ligand include ligands disclosed on pages 89 to 90 of Lamansky, et al., WO 02/15645, but it should not be construed that the invention is limited thereto.

It is preferable that X—Y represents a monoanionic bidentate ligand represented by the following formula (I-1), (I-2) or (I-3).

(I-1)

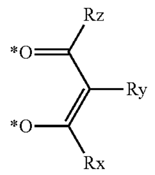

(I-2)

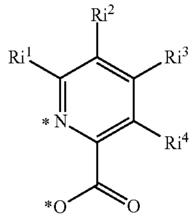

(I-3)

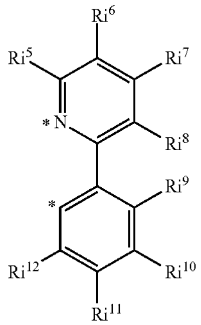

In the formula (I-1), each of Rx and Rz independently represents an alkyl group, a perfluoroalkyl group or an aryl group; and Ry represents a hydrogen atom, an alkyl group, a perfluoroalkyl group or an aryl group.

In the formula (I-2), each of $Ri^1$ to $Ri^4$ independently represents a hydrogen atom, an alkyl group, a perfluoroalkyl group, an aryl group, an alkoxy group, an aryloxy group, a dialkylamino group, a diarylamino group, a cyano group, a fluorine atom, a trialkylsilyl group, a triarylsilyl group, an alkyldiarylsilyl group, a dialkylarylsilyl group, a heterocyclic group or a heterocyclic oxy group; and adjacent substituents among $Ri^1$ to $Ri^4$ may be connected to each other.

In the formula (I-3), each of $Ri^5$ to $Ri^{12}$ independently represents a hydrogen atom, an alkyl group, a perfluoroalkyl group, an aryl group, an alkoxy group, an aryloxy group, a dialkylamino group, a diarylamino group, a cyano group, a fluorine atom, a trialkylsilyl group, a triarylsilyl group, an alkyldiarylsilyl group, a dialkylarylsilyl group, a heterocyclic group or a heterocyclic oxy group; and adjacent substituents among $Ri^5$ to $Ri^8$, adjacent substituents among $Ri^9$ to $Ri^{12}$, and $Ri^8$ and $Ri^9$ may be each connected to each other.

In the formulae (I-1), (I-2) and (I-3), the monoanionic bidentate ligand is bonded to iridium at the atom marked with "*".

In the formula (I-1), each of Rx and Rz independently represents an alkyl group, a perfluoroalkyl group or an aryl group. Each of Rx and Rz is preferably an alkyl group having from 1 to 5 carbon atoms, a trifluoromethyl group or a phenyl group which may have a substituent selected from the following substituent group T (also referred to as "substituent T"). Plural substituents Ts may be connected to each other. In the invention, the substituent group T is defined as follows.

(Substituent Group T)

An alkyl group having a from 1 to 6 carbon atoms, a phenyl group, an aromatic heterocyclic group having from 5 to 10 carbon atoms, an alkoxy group having from 1 to 4 carbon atoms, a phenoxy group, a fluorine atom, a silyl group, an amino group, a cyano group and a group composed of a combination of these groups.

In the formula (I-1), Ry represents a hydrogen atom, an alkyl group, a perfluoroalkyl group or an aryl group. Ry is preferably a hydrogen atom, an alkyl group having from 1 to 5 carbon atoms or a phenyl group which may have the foregoing substituent T, and more preferably a hydrogen atom. Plural substituents Ts may be connected to each other.

In the formula (I-2), each of $Ri^1$ to $Ri^4$ independently represents a hydrogen atom, an alkyl group, a perfluoroalkyl group, an aryl group, an alkoxy group, an aryloxy group, a dialkylamino group, a diarylamino group, a cyano group, a fluorine atom, a trialkylsilyl group, a triarylsilyl group, an alkyldiarylsilyl group, a dialkylarylsilyl group, a heterocyclic group or a heterocyclic oxy group; and adjacent substituents among $Ri^1$ to $Ri^4$ may be connected to each other.

$Ri^1$ is preferably a hydrogen atom or an alkyl group, and more preferably a hydrogen atom.

$Ri^2$ is preferably a hydrogen atom, an alkyl group, an aryl group or a heterocyclic group; more preferably a hydrogen atom or an alkyl group; and further preferably a hydrogen atom.

$Ri^3$ is preferably a hydrogen atom, an alkyl group, an aryl group, an alkoxy group, an aryloxy group, a dialkylamino group, a fluorine atom or a heterocyclic group; more preferably a hydrogen atom, an alkyl group, an aryl group or a fluorine atom; further preferably a hydrogen atom or an alkyl group; and especially preferably a hydrogen atom.

$Ri^4$ is preferably a hydrogen atom, an alkyl group, an aryl group or a heterocyclic group; more preferably a hydrogen atom or an alkyl group; and further preferably a hydrogen atom.

In the formula (I-3), each of $Ri^5$ to $Ri^{12}$ independently represents a hydrogen atom, an alkyl group, a perfluoroalkyl group, an aryl group, an alkoxy group, an aryloxy group, a dialkylamino group, a diarylamino group, a cyano group, a fluorine atom, a trialkylsilyl group, a triarylsilyl group, an alkyldiarylsilyl group, a dialkylarylsilyl group, a heterocyclic group or a heterocyclic oxy group; and adjacent substituents among $Ri^5$ to $Ri^8$, adjacent substituents among $Ri^9$ to $Ri^{12}$, and $Ri^8$ and $Ri^9$ may be each connected to each other.

$Ri^5$ is preferably a hydrogen atom or an alkyl group.

$Ri^6$ is preferably a hydrogen atom, an alkyl group, an aryl group or a heterocyclic group; and more preferably a hydrogen atom or an alkyl group.

$Ri^7$ is preferably a hydrogen atom, an alkyl group, an aryl group, an alkoxy group, an aryloxy group, a dialkylamino group, a fluorine atom or a heterocyclic group; more preferably a hydrogen atom, an alkyl group, an aryl group or a fluorine atom; further preferably a hydrogen atom or an alkyl group; and especially preferably a hydrogen atom.

$Ri^8$ is preferably a hydrogen atom, an alkyl group, an aryl group or a heterocyclic group; more preferably a hydrogen atom or an alkyl group; and further preferably a hydrogen atom.

$Ri^9$ is preferably a hydrogen atom, an alkyl group, an aryl group, a heterocyclic group or a fluorine atom; and more preferably a hydrogen atom, an alkyl group or a fluorine atom.

$R^{10}$ is preferably a hydrogen atom, an alkyl group, an aryl group or a heterocyclic group; and more preferably a hydrogen atom, an alkyl group or an aryl group.

$Ri^{11}$ is preferably a hydrogen atom, an alkyl group, an aryl group, a heterocyclic group or a fluorine atom; and more preferably a hydrogen atom, an alkyl group, an aryl group or a fluorine atom.

$R^{12}$ is preferably a hydrogen atom, an alkyl group, an aryl group or a heterocyclic group; and more preferably a hydrogen atom or an alkyl group.

More preferred examples of the monoanionic bidentate ligand include acetylacetonate (acac), picolinate (pic) and derivatives thereof. In the invention, from the viewpoints of stability of the complex and high light emission quantum yield, the monoanionic bidentate ligand is preferably acetylacetonate.

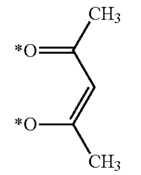

acac

In the foregoing formulae, the monoanionic bidentate ligand is bonded to iridium at the atom marked with "*".

A preferred embodiment of the Ir complex represented by the formula (E-1) is an Ir complex material represented by the following formula (E-2).

Next, the formula (E-2) is described.

(E-2)

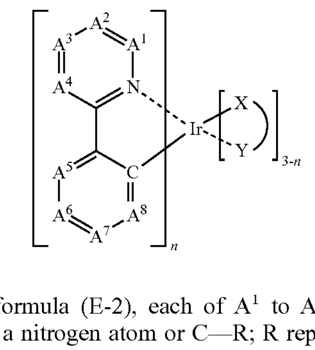

In the formula (E-2), each of $A^1$ to $A^8$ independently represents a nitrogen atom or C—R; R represents a hydrogen atom or a substituent; X—Y represents a monoanionic bidentate ligand; and n represents an integer of from 1 to 3.

Each of $A^1$ to $A^8$ independently represents a nitrogen atom or C—R. R represents a hydrogen atom or a substituent; and Rs may be connected to each other to form a ring. As the substituent represented by R, those exemplified previously in the substituent group A can be applied. R preferably represents a hydrogen atom, an alkyl group, an aryl group, an aromatic heterocyclic group, a cyano group, a silyl group, an amino group or a fluorine atom. If possible, such a substituent can further have a substituent, and as the substituent, those exemplified previously in the substituent group A can be applied. The substituent is preferably an alkyl group, an aryl group, an aromatic heterocyclic group, a cyano group, a silyl group, an amino group or a fluorine atom.

Each of $A^1$ to $A^4$ is preferably C—R. In the case where each of $A^1$ to $A^4$ is C—R, R of $A^3$ is preferably a hydrogen atom, an alkyl group, an aryl group, an amino group, a fluorine atom or a cyano group; more preferably a hydrogen atom, an amino group or a fluorine atom; and especially preferably a hydrogen atom or a fluorine atom.

In the case where each of $A^1$, $A^2$ and $A^4$ is C—R, R is preferably a hydrogen atom, an alkyl group, an aryl group, an amino group, a fluorine atom or a cyano group; more preferably a hydrogen atom, an amino group or a fluorine atom; and especially preferably a hydrogen atom.

Each of $A^5$ to $A^8$ independently represents C—R or a nitrogen atom. R represents a hydrogen atom, an alkyl group, an aryl group, an aromatic heterocyclic group, a cyano group, a silyl group, an amino group or a fluorine atom. If possible, such a substituent can further have a substituent, and as the substituent, those exemplified previously in the substituent group A can be applied. The substituent is preferably an alkyl group, an aryl group, an aromatic heterocyclic group, a cyano group, a silyl group, an amino group or a fluorine atom.

In the case where each of $A^5$ to $A^8$ is C—R, R is preferably a hydrogen atom, an alkyl group, a perfluoroalkyl group, an aryl group, an aromatic heterocyclic group, a dialkylamino group, a diarylamino group, a cyano group or a fluorine atom; more preferably a hydrogen atom, an alkyl group, a perfluoroalkyl group, an aryl group, a dialkylamino group, a cyano group or a fluorine atom; and further preferably a hydrogen atom, an alkyl group, a trifluoromethyl group or a fluorine atom. Also, if possible, the substituents may be connected to each other to form a condensed ring structure. In the case where the light emission wavelength is shifted to the short wavelength side, it is preferable that $A^6$ is an N atom.

X—Y and n are synonymous with X—Y and n in the formula (E-1), and preferred ranges thereof are also the same.

Another preferred embodiment of the Ir complex represented by the formula (E-1) is an iridium complex material represented by the following formula (E-3).

Next, the formula (E-3) is described.

(E-3)

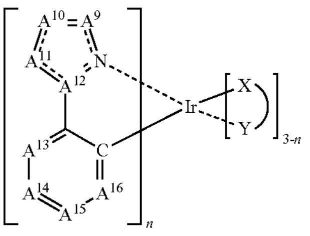

In the formula (E-3), each of $A^9$ to $A^{11}$ and $A^{13}$ to $A^{16}$ independently represents C—R, N or N—R'; $A^{12}$ represents a carbon atom or a nitrogen atom; R represents a hydrogen atom or a substituent; R' represents a hydrogen atom or a substituent; X—Y represents a monoanionic bidentate ligand; and n represents an integer of from 1 to 3.

Each of $A^9$ to $A^{11}$ and $A^{13}$ to $A^{16}$ independently represents C—R, N or N—R'. R preferably represents a hydrogen atom, an alkyl group, an aryl group, an aromatic heterocyclic group, a cyano group, a silyl group, an amino group or a fluorine atom. R' preferably represents a hydrogen atom, an alkyl group or an aryl group.

Each of $A^9$ and $A^{10}$ is preferably C—R. In the case where each of $A^9$ and $A^{10}$ is C—R, R of each of $A^9$ and $A^{10}$ is preferably a hydrogen atom, an alkyl group, an aryl group, an amino group, an alkoxy group, an aryloxy group, a fluorine atom or a cyano group; more preferably a hydrogen atom, an alkyl group, an aryl group, an amino group, a fluorine atom or a cyano group; further preferably a hydrogen atom, an amino group or a fluorine atom; and especially preferably a hydrogen atom or a fluorine atom. If possible, such a substituent can further have a substituent. As the substituent, those exemplified previously in the substituent group A can be applied. The substituent is preferably an alkyl group, an aryl group, an aromatic heterocyclic group, a cyano group, a silyl group, an amino group or a fluorine atom.

$A^{11}$ is preferably N—R', and R' of $A^{11}$ is preferably an alkyl group or an aryl group. Plural Rs or R's may be connected to each other to form a ring.

X—Y and n are synonymous with X—Y and n in the formula (E-1), and preferred ranges thereof are also the same.

The formula (E-3) is more preferably an iridium complex represented by the following formula (E-4).

(E-4)

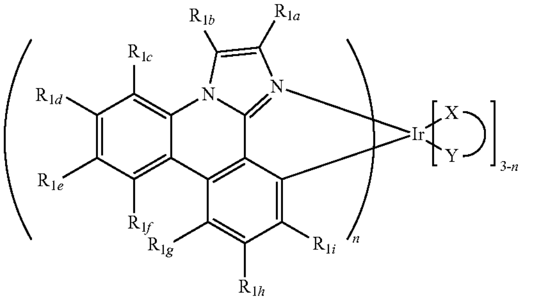

In the formula (E-4), each of $R_{1a}$ to $R_{1i}$ independently represents a hydrogen atom or a substituent; X—Y represents a monoanionic bidentate ligand; and n represents an integer of from 1 to 3.

In the formula (E-4), each of $R_{1a}$ to $R_{1i}$ independently represents a hydrogen atom or a substituent. As the substituent, those exemplified previously in the substituent group A can be applied. Each of $R_{1a}$ to $R_{1i}$ is preferably a hydrogen atom, an alkyl group, an aryl group, an aromatic heterocyclic group, a cyano group, a silyl group, an amino group or a fluorine atom. If possible, such a substituent can further have a substituent. As the substituent, those exemplified previously in the substituent group A can be applied. The substituent is preferably an alkyl group, an aryl group, an aromatic heterocyclic group, a cyano group, a silyl group, an amino group or a fluorine atom. In the case where each of $R_{1a}$ to $R_{1i}$ is bonded to the nitrogen atom, each of $R_{1a}$ to $R_{1i}$ is not a hydrogen atom.

Each of $R_{1a}$ to $R_{1i}$ is preferably a hydrogen atom, an alkyl group, an aryl group, an amino group, a fluorine atom or a cyano group; more preferably a hydrogen atom, an alkyl group, an aryl group, a fluorine atom or a cyano group; and especially preferably a hydrogen atom, an alkyl group or an aryl group.

At least one of $R_{1a}$ to $R_{1i}$ is preferably an aryl group having a dihedral angle against the mother structure of 70 degrees or more, more preferably a substituent represented by the following formula ss-1, and further preferably a 2,6-disubstituted aryl group. It is the most preferable that $R_{1b}$ is a 2,6-disubstituted aryl group.

ss-1

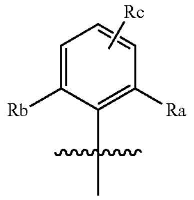

In the formula ss-1, each of Ra, Rb and Rc independently represents any one of a hydrogen atom, an alkyl group and an aryl group.

The alkyl group represented by each of Ra, Rb and Rc has preferably from 1 to 30 carbon atoms, more preferably from 1 to 20 carbon atoms, and especially preferably from 1 to 10 carbon atoms, and examples thereof include methyl, ethyl, n-propyl, isopropyl, n-butyl, tert-butyl, n-octyl, n-nonyl, n-decyl, n-dodecyl, n-octadecyl, n-hexadecyl, cyclopropyl, cyclobutyl, cyclopentyl, cyclohexyl, cyclooctyl, 1-adamantyl and trifluoromethyl. Of those, a methyl group and an isopropyl group are preferable.

The aryl group represented by each of Ra, Rb and Rc has preferably from 6 to 30 carbon atoms, more preferably from 6 to 20 carbon atoms, and especially preferably from 6 to 12 carbon atoms, and examples thereof include phenyl, o-methylphenyl, m-methylphenyl, p-methylphenyl, 2,6-xylyl, p-cumenyl, mesityl, naphthyl and anthranyl. Of those, a phenyl group is preferable.

At least one of Ra and Rb is selected from an alkyl group or an aryl group; it is preferable that at least one of Ra and Rb is selected from an alkyl group; it is more preferable that both Ra and Rb are an alkyl group; and it is the most preferable that both Ra and Rb are a methyl group or an isopropyl group.

The 2,6-disubstituted aryl group is preferably a 2,6-dimethylphenyl group, a 2,4,6-trimethylphenyl group, a 2,6-diisopropylphenyl group, a 2,4,6-triisopropylphenyl group, a 2,6-dimethyl-4-phenylphenyl group, a 2,6-dimethyl-4-(2,6-dimethylpyridin-4-yl)phenyl group, a 2,6-diphenylphenyl group, a 2,6-diphenyl-4-isopropylphenyl group, a 2,4,6-triphenylphenyl group, a 2,6-diisopropyl-4-(4-isopropylphenyl)phenyl group, a 2,6-diisopropyl-4-(3,5-dimethylphenyl)phenyl group, a 2,6-diisopropyl-4-(pyridin-4-yl)phenyl group or a 2,6-di(3,5-dimethylphenyl)phenyl group.

On the other hand, it is preferable that at least one of $R_{1a}$ to $R_{1i}$ is an alkyl group; and it is more preferable that $R_{1e}$ is an alkyl group. The alkyl group is preferably an alkyl group branched at a site far from the benzyl position composed of 4 or more carbon atoms. The alkyl group is preferably a methyl group or a neopentyl group, and more preferably a neopentyl group.

On the other hand, it is preferable and at least one of $R_{1a}$ and $R_{1b}$ is an alkyl group.

On the other hand, $R_{1a}$ is preferably an electron-donating group, and more preferably a methyl group.

X—Y and n are synonymous with X—Y and n in the formula (E-1), and preferred ranges thereof are also the same.

A still another preferred embodiment of the Ir complex represented by the formula (E-1) is an iridium complex material represented by the following formula (PQ-1).

The compound represented by the formula (PQ-1) is described.

(PQ-1)

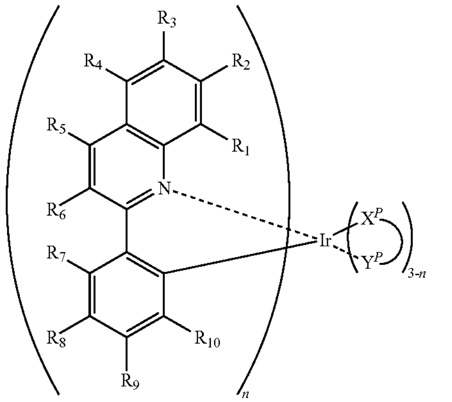

In the formula (PQ-1), each of $R_1$ to $R_{10}$ independently represents a hydrogen atom, an alkyl group, an aryl group, an aromatic heterocyclic group, a cyano group, a silyl group, an amino group or a fluorine atom; $R_1$ to $R_{10}$ may be bonded to each other to form a ring, if possible; $X^P$—$Y^P$ represents a monoanionic bidentate ligand represented by the foregoing formula (I-1), (I-2) or (I-3); and n represents an integer of from 1 to 3.

Each of $R_1$ to $R_{10}$ independently represents a hydrogen atom, an alkyl group, an aryl group, an amino group, a cyano group, an aromatic heterocyclic group, a silyl group or a fluorine atom; preferably a hydrogen atom, an alkyl group, an aryl group, an amino group, a cyano group, a silyl group or a fluorine atom; more preferably a hydrogen atom, an alkyl group or an aryl group; especially preferably a hydrogen atom, a methyl group, an ethyl group, an isopropyl group, a t-butyl group, a neopentyl group, an isobutyl group, a phenyl group, a naphthyl group, a phenanthryl group or a tolyl group; and most preferably a hydrogen atom, a methyl group or a phenyl group.

If possible, such a substituent can further have a substituent, and as the substituent, those exemplified previously in the substituent group A can be applied. The substituent is preferably an alkyl group, an aryl group, an aromatic heterocyclic group, a cyano group, a silyl group, an amino group or a fluorine atom.

Also, if possible, these substituents may be bonded to each other to form a ring.

The ring which the substituents form each other is preferably a 5- to 6-membered ring, and examples thereof include a benzene ring, a pyridine ring, a pyrimidine ring, a pyrazine ring, an imidazole ring, a pyrazole ring, an oxazole ring, a thiazole ring, a thiophene ring and a furan ring. Of these, a benzene ring, a pyridine ring and a pyrazine ring are more preferable; a benzene ring and a pyridine ring are further preferable; and a benzene ring is especially preferable. The ring which the substituents form each other may further have a substituent, and as the substituent, those exemplified previously in the substituent group A can be applied. The substituent is preferably an alkyl group, a perfluoroalkyl group, an aryl group, an aromatic heterocyclic group, a dialkylamino group, a diarylamino group, an alkoxy group, a cyano group or a fluorine atom.

n is preferably from 2 to 3, and more preferably 2.

($X^P$—$Y^P$) is synonymous with X—Y in the foregoing formula (E-1), and a preferred range thereof is also the same. It may be considered that such a ligand does not directly contribute to light emitting characteristics but is able to control the light emitting characteristics of a molecule. Examples of such a monoanionic bidentate ligand include ligands disclosed on pages 89 to 90 of Lamansky, et al., WO 02/15645. Preferred examples of the monoanionic bidentate ligand include acetylacetonate (acac), picolinate (pic) and derivatives thereof.

($X^P$—$Y^P$) is especially preferably a bidentate ligand represented by the following formula L.

Formula L

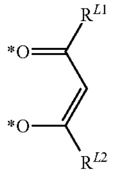

In the formula L, each of $R^{L1}$ and $R^{L2}$ independently represents an alkyl group having from 1 to 5 carbon atoms or a phenyl group which may have a substituent selected from a substituent group T2. In the invention, the substituent group T2 is defined as follows.

(Substituent Group T2)

An alkyl group having from 1 to 6 carbon atoms, an alkenyl group having from 2 to 6 carbon atoms, a phenyl group, an aromatic heterocyclic group having from 5 to 10 carbon atoms, an alkoxy group having from 1 to 4 carbon atoms, a phenoxy group, a fluorine atom, a silyl group, an amino group, a cyano group and a group composed of a combination of these groups.

Plural substituents selected from the substituent group T2 may be connected to each other to form an aromatic hydrocarbon ring; and the monoanionic bidentate ligand is bonded to iridium at the atom marked with "*".

Each of $R^{L1}$ and $R^{L2}$ is preferably a methyl group, an ethyl group, an n-propyl group, an isopropyl group, an n-butyl group, an isobutyl group, a t-butyl group, a phenyl group, a tolyl group, an ethylphenyl group, a biphenyl group or a naphthyl group; more preferably a methyl group, an ethyl group, a t-butyl group or a phenyl group; and further preferably a methyl group, a t-butyl group or a phenyl group.

Examples of the organometallic complex of the invention are enumerated below, but it should not be construed that the invention is limited thereto.

1
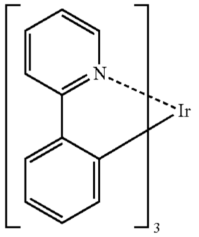
2
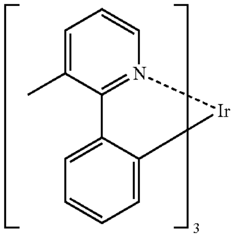
3
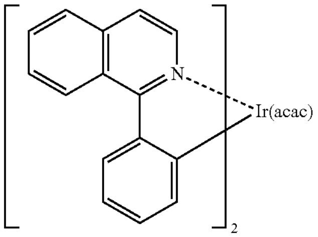
4
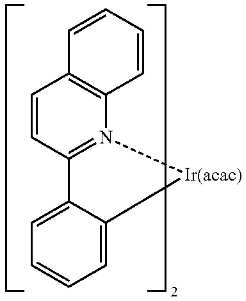
5
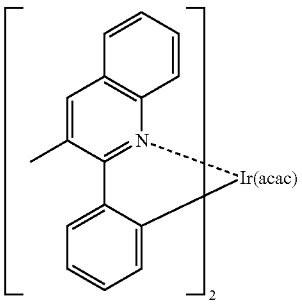
-continued
6
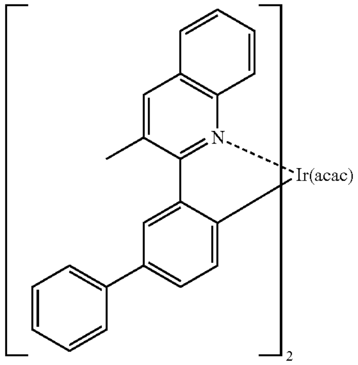
7
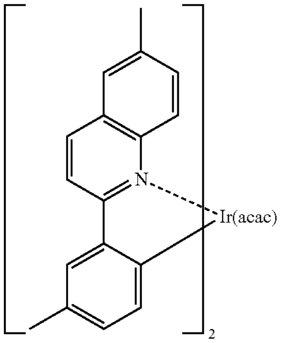
8
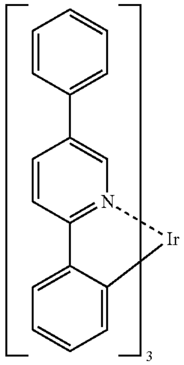
9
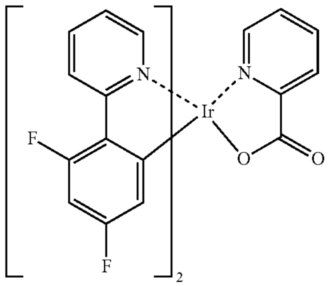

-continued
10
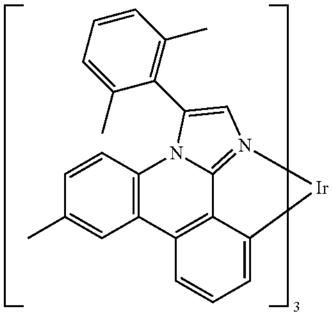
11
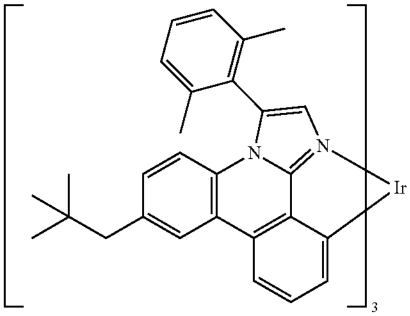
12
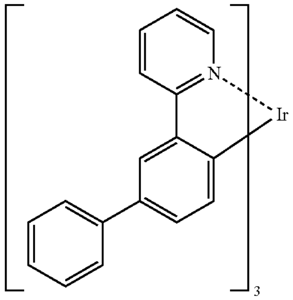
13
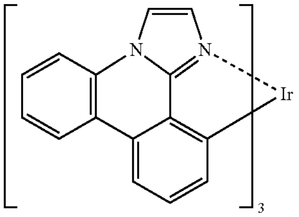
14
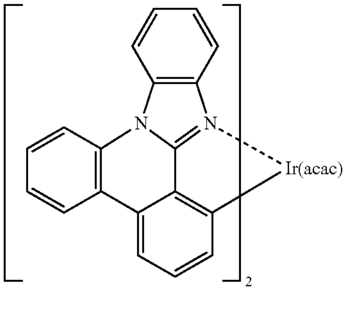
-continued
15
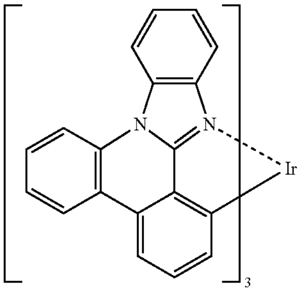
16
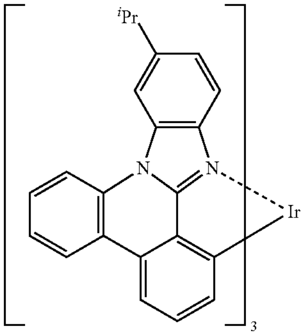
17
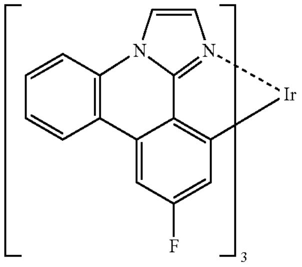
18
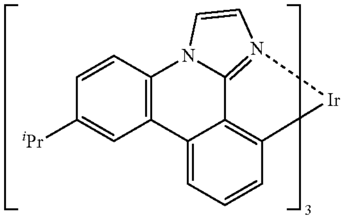
19
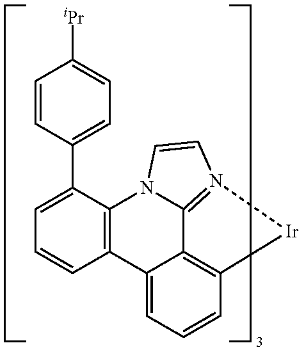

-continued
20
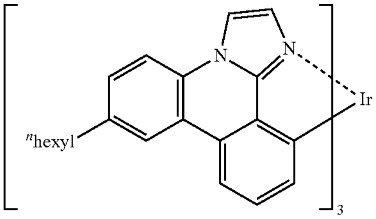
21
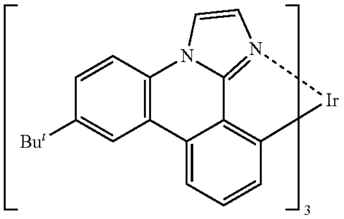
22
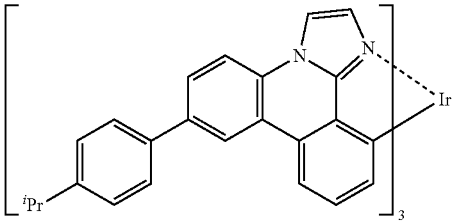
23
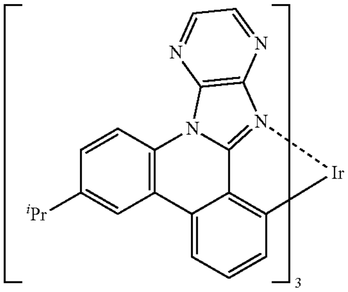
24
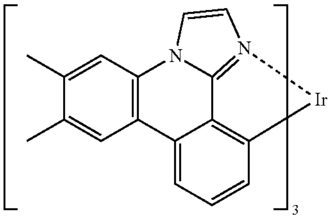
25
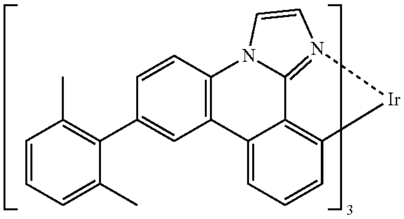
-continued
26
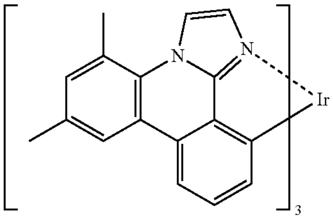
27
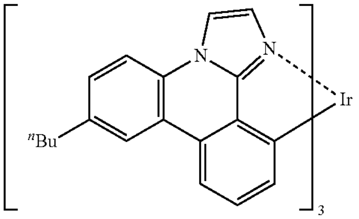
28
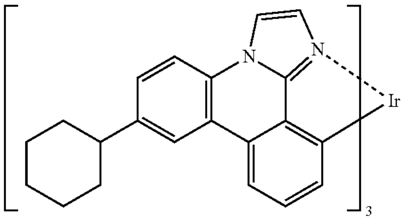
29
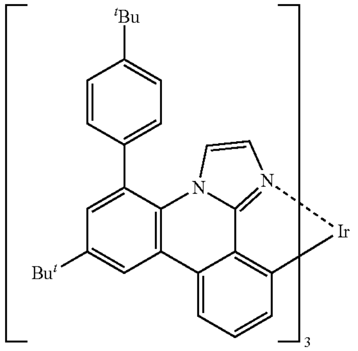
30
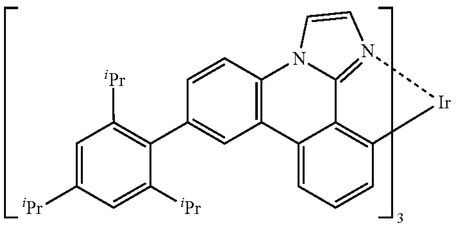
31
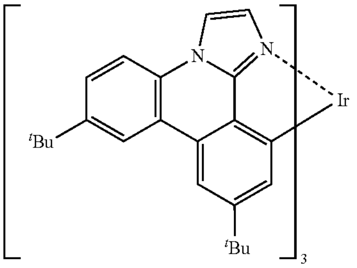

-continued
32
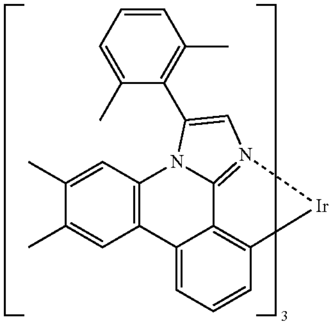
33
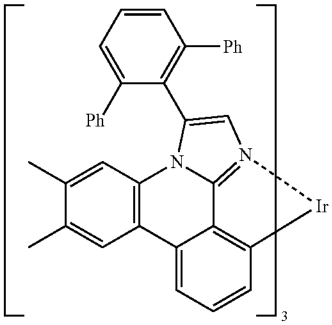
34
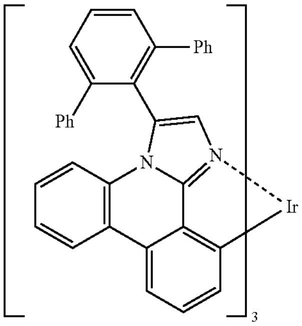
35
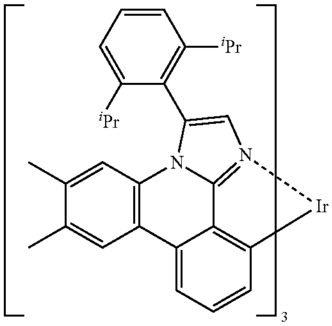
36
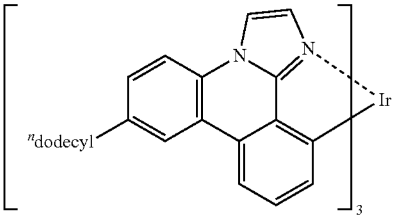
-continued
37
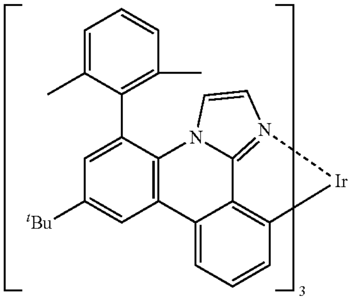
38
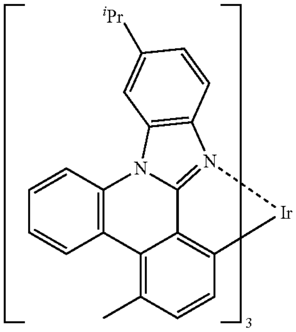
39
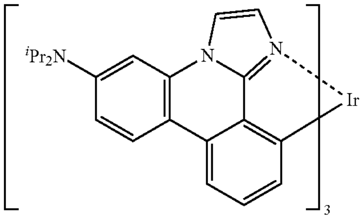
40
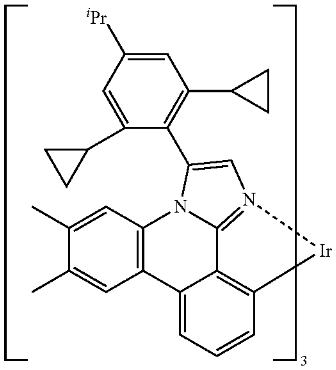
41
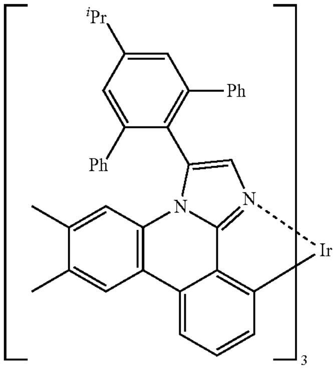

-continued
42
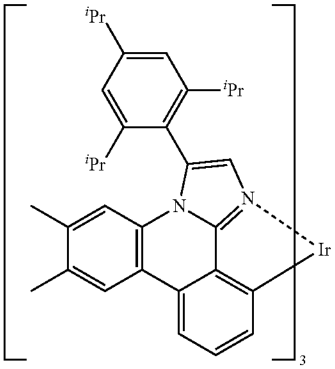
43
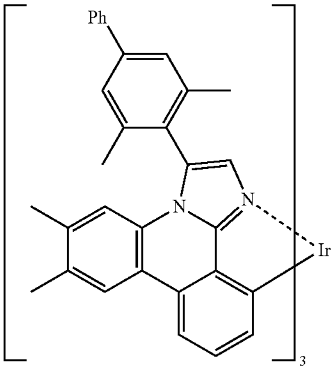
44
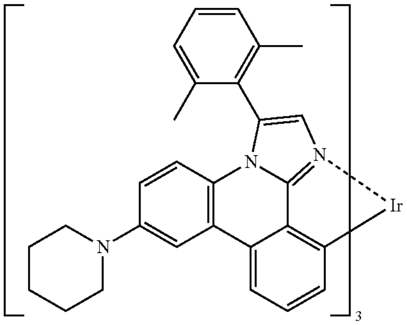
45
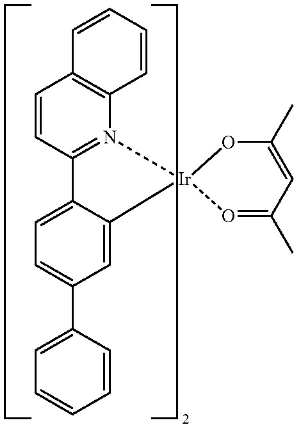
-continued
46
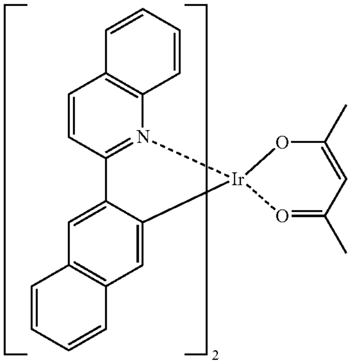
47
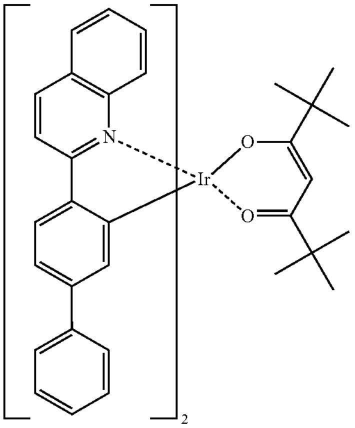
48
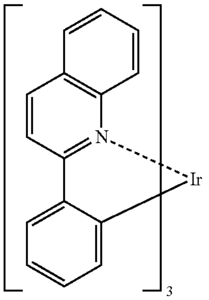
49
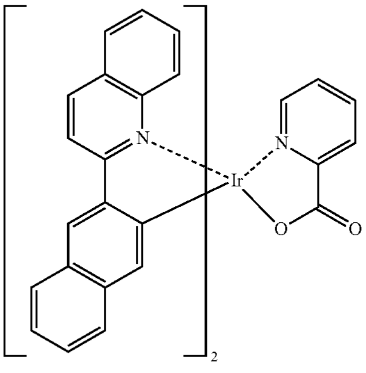

-continued
50
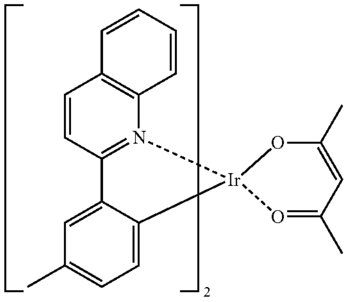
51
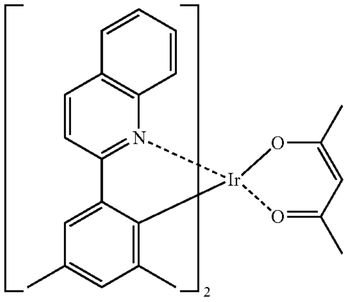
52
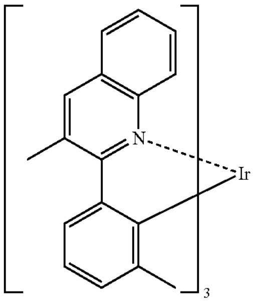
53
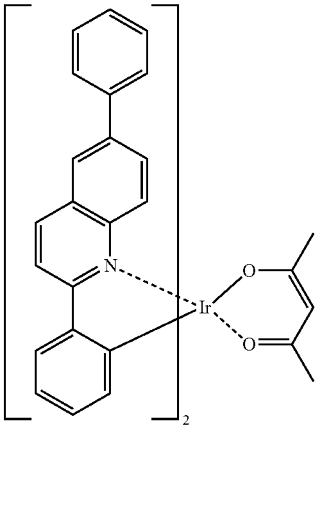
-continued
54
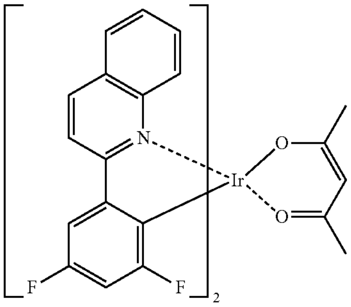
55
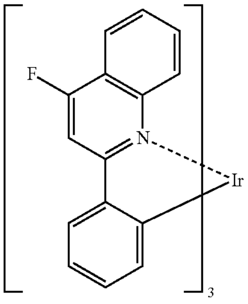
56
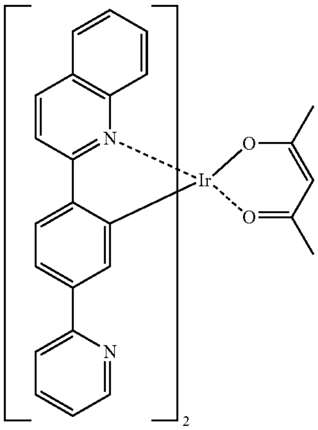
57
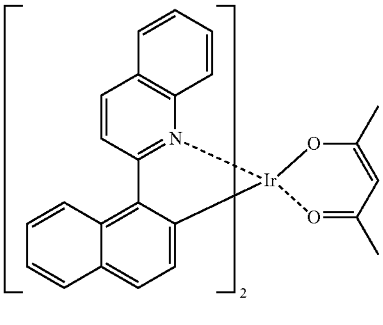

-continued
58
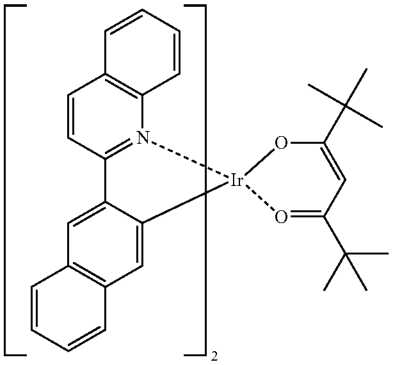
59
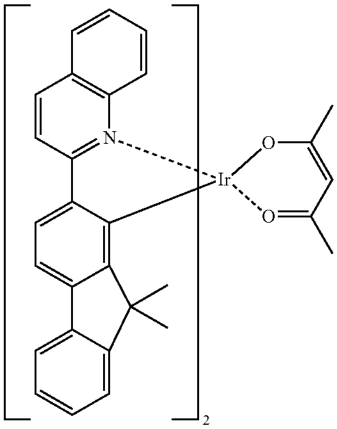
60
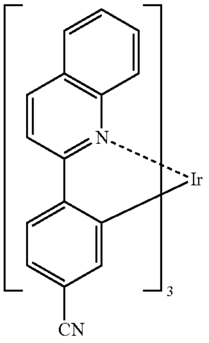
61
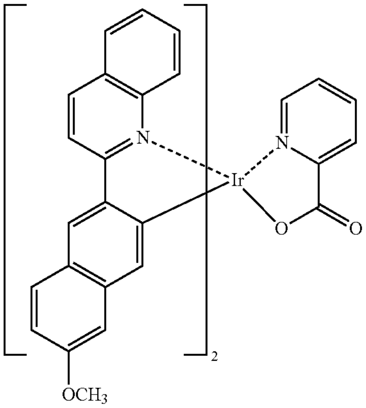
-continued
62
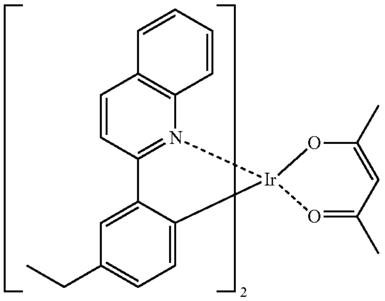
63
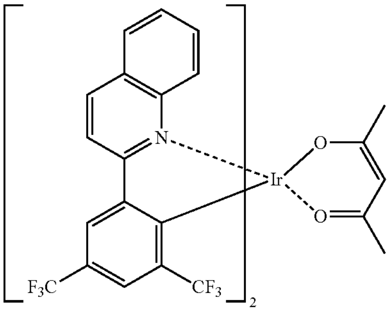
64
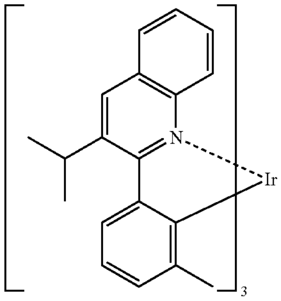
65
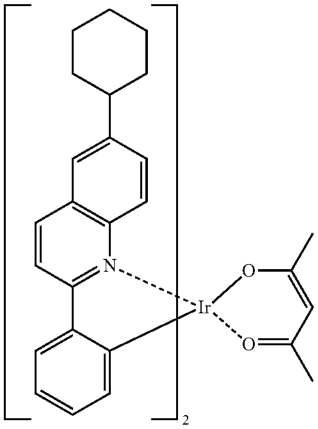

-continued
66
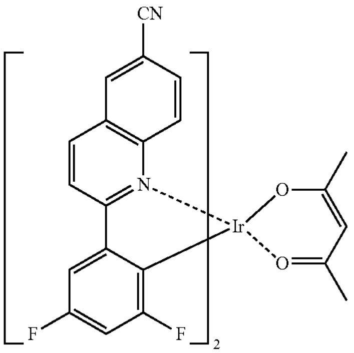
67
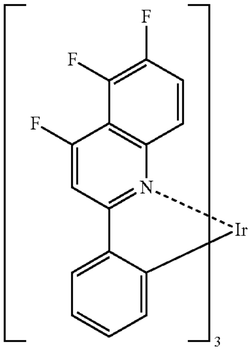
68
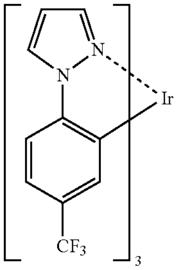
69
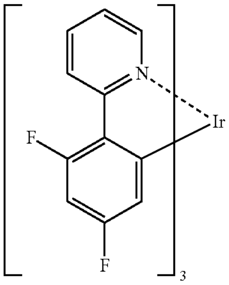
70
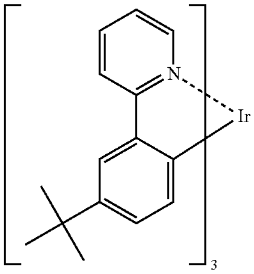
-continued
71
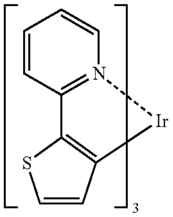
72
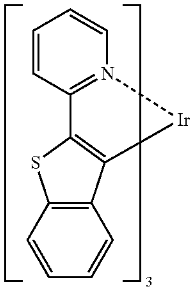
73
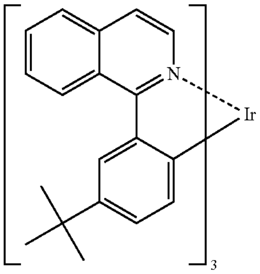
74
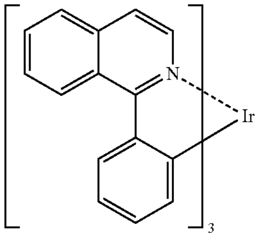
75
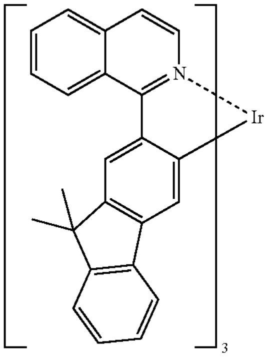
76
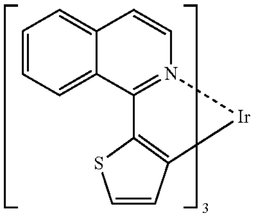

-continued
77
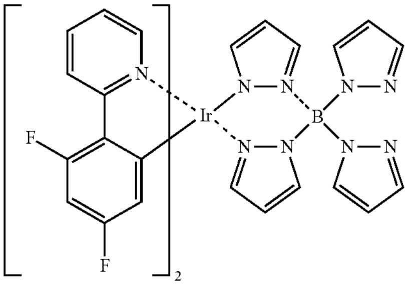
78
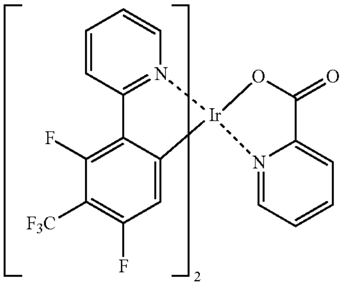
79
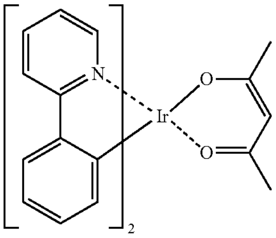
80
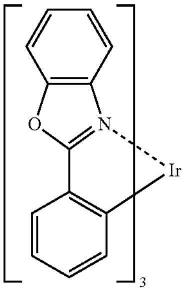
81
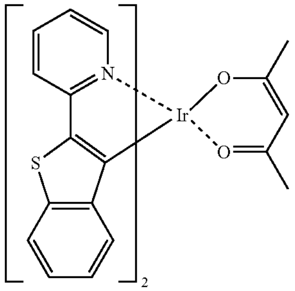
-continued
82
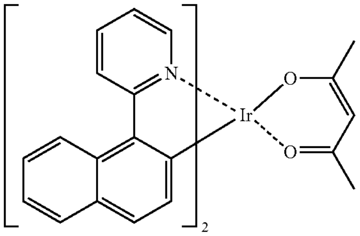
83
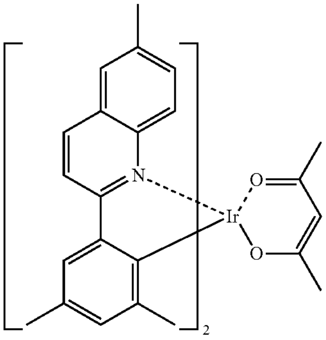
84
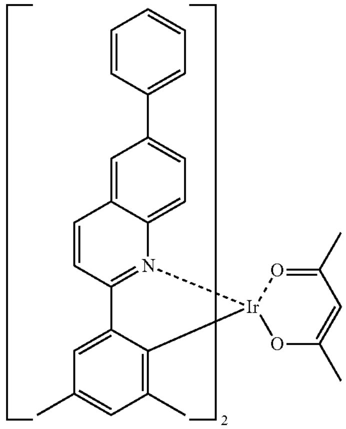
85
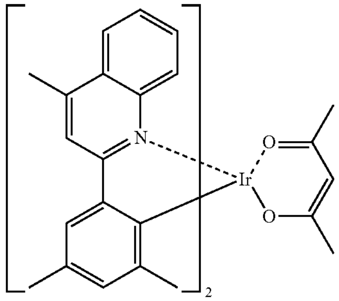
86
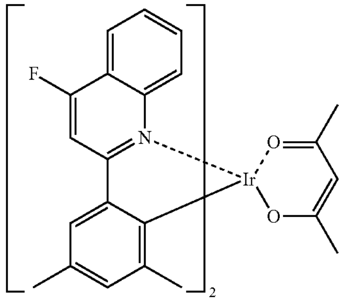

-continued
87
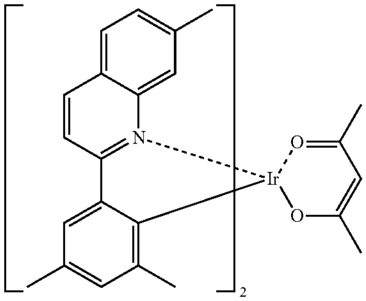
88
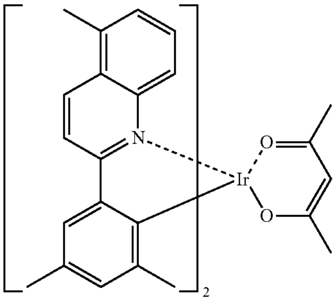
89
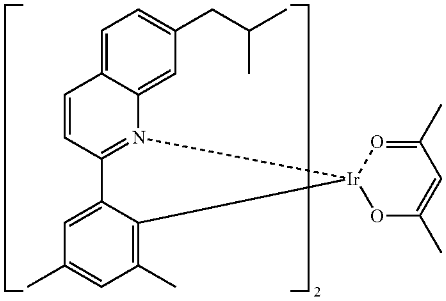
90
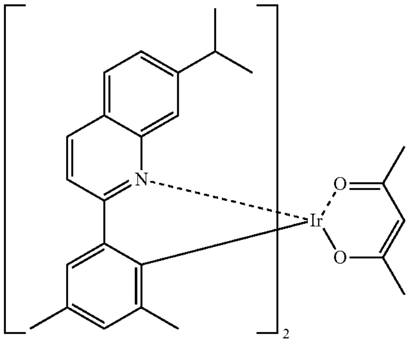
91
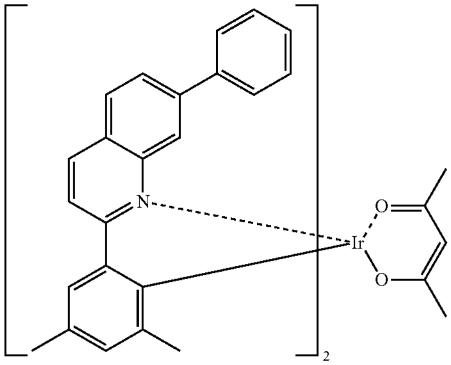
-continued
92
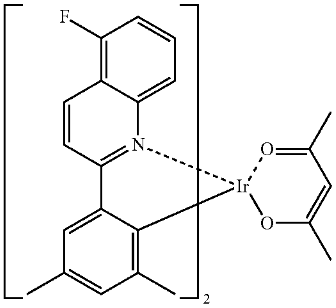
93
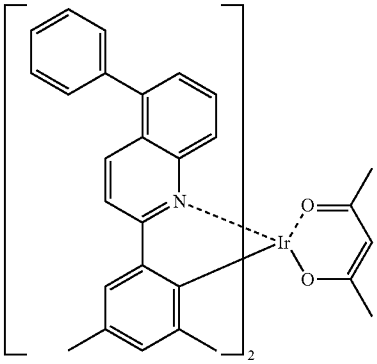
94
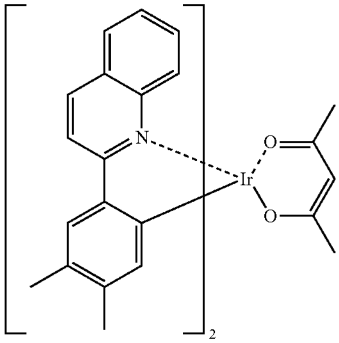
95
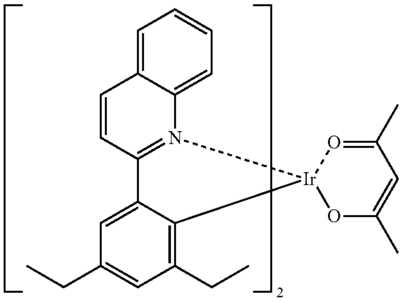

-continued

96

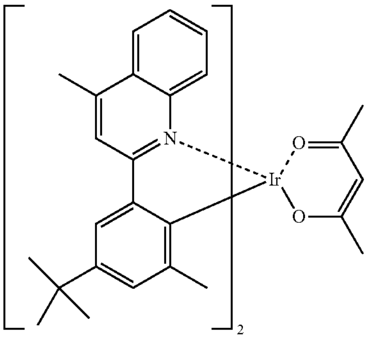

97

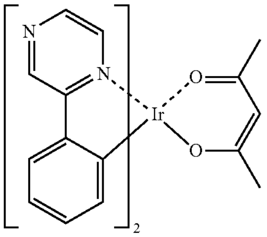

98

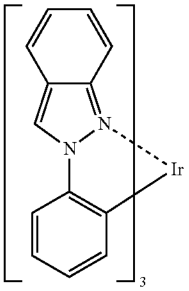

99

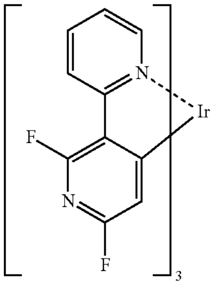

100

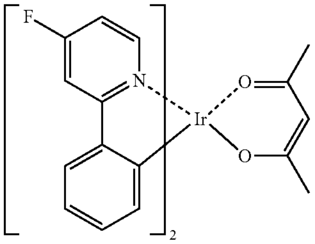

-continued

101

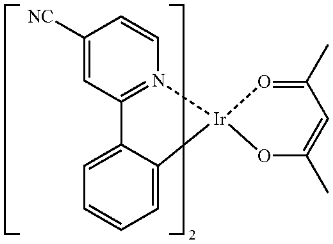

102

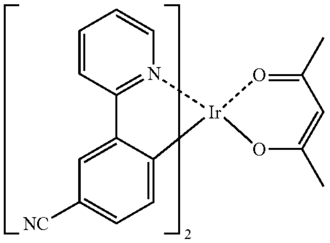

103

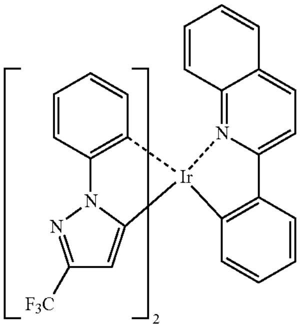

104

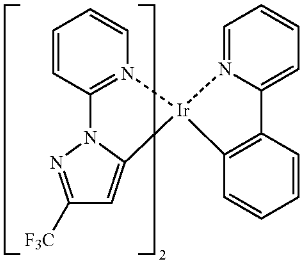

The phosphorescent metal complex containing the mono-anionic bidentate ligand represented by any one of the formulae (E-1) to (E-4) and iridium can be synthesized by various techniques such as methods disclosed in, for example, US2007/0190359 and US2008/0297033.

For example, the phosphorescent metal complex can be obtained by a reaction of a ligand or a dissociated material thereof and a metal compound in the absence or presence of a solvent (for example, halogen based solvents, alcohol based solvents, ether based solvents, ester based solvents, ketone based solvents, nitrile based solvents, amide based solvents, sulfone based solvents, sulfoxide based solvents, water, etc.) and in the absence or presence of a base (various inorganic or organic bases, for example, sodium methoxide, t-butoxypotassium, triethylamine, potassium carbonate, etc.) at a temperature of not higher than room temperature or by heating (in addition to usual heating, a heating technique with a microwave is also effective).

Also, the compounds exemplified previously as the compound represented by the formula (PQ-1) can be synthesized by various methods such as a method disclosed in, for example, U.S. Pat. No. 3,929,689. For example, Compound 4 can be synthesized using 2-phenylquinoline as a starting raw material by a method disclosed at page 18, lines 2 to 13 of U.S. Pat. No. 3,929,689. Also, Compound 58 can be synthesized using 2-(2-naphthyl)quinoline as a starting raw material by a method disclosed at page 18, line 14 to page 19, line 8 of U.S. Pat. No. 3,929,689.

The material for organic luminescence device of the invention can be used for the preparation of an organic electroluminescence device.

[Light Emitting Layer Prepared Using the Material for Organic Electroluminescence Material Having a Water Content Before Film Formation of 100 ppm or More and not More than 1,000 ppm]

The invention is also concerned with a light emitting layer prepared using the foregoing material for organic electroluminescence material having a water content before film formation of 100 ppm or more and not more than 1,000 ppm. The light emitting layer of the invention can be used for an organic electroluminescence device.

In the light emitting layer of the invention, a preferred range of the material for organic electroluminescence device having a water content before film formation of 100 ppm or more and not more than 1,000 ppm is one described previously, and it is preferable that the material for organic electroluminescence device is the foregoing phosphorescent iridium complex.

It is preferable that the light emitting layer of the invention is subjected to film formation by further using at least one host material in addition to the foregoing phosphorescent organometallic complex. Though the host material may be any of a hole transporting host material or an electron transporting host material, it is preferably a both charge transporting host material.

From the viewpoint that an organic electroluminescence device with excellent external quantum efficiency and driving durability, the host material is preferably a compound represented by the following formula (4-1) or (4-2).

The material represented by the formula (4-1) or (4-2) is described.

Formula (4-1)

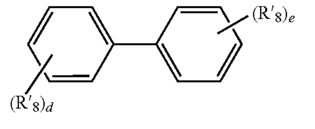

Formula (4-2)

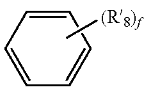

In the formulae (4-1) and (4-2), each of d and e represents an integer of from 0 to 3, and at least one of them is 1 or more; f represents an integer of from 1 to 4; $R'_8$ represents a substituent; when plural $R'_8$s are present, each $R'_8$ may be the same as or different from every other $R'_8$; and at least one of $R'_8$s represents a carbazole group represented by the following formula (5).

(5)

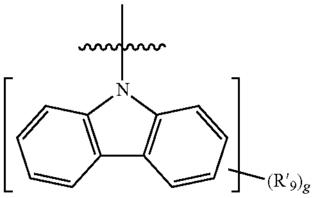

In the formula (5), each of $R'_9$s independently represents a substituent; and g represents an integer of from 0 to 8.

Each of $R'_8$s independently represents a substituent, and specifically, it is a halogen atom, an alkoxy group, a cyano group, a nitro group, an alkyl group, an aryl group, a heterocyclic group or the substituent represented by the formula (5). In the case where $R'_8$ does not represent the formula (5), it is preferably an alkyl group having not more than 10 carbon atoms or a substituted or unsubstituted aryl group having not more than 10 carbon atoms, and more preferably an alkyl group having not more than 6 carbon atoms.

Each of $R'_9$s independently represents a substituent, and specifically, it is a halogen atom, an alkoxy group, a cyano group, a nitro group, an alkyl group, an aryl group or a heterocyclic group, preferably an alkyl group having not more than 10 carbon atoms or a substituted or unsubstituted aryl group having not more than 10 carbon atoms, and more preferably an alkyl group having not more than 6 carbon atoms.

g represents an integer of from 0 to 8; and from the viewpoint that the carbazole structure bearing charge transport is not excessively blocked, g is preferably from 0 to 4. Also, from the viewpoint of easy synthesis, in the case where the carbazole has a substituent, it is preferable to have a substituent such that it is symmetrical about the nitrogen atom.

In the formula (4-1), from the viewpoint of keeping charge transport capability, the sum of d and e is preferably 2 or more. Also, it is preferable that $R'_8$ is substituted at a meta-position against the other benzene ring. This is because in the ortho-substitution, a steric hindrance between the adjacent substituents to each other is large, and therefore, the bond is easily cleaved, and the durability becomes low. Also, in the para-substitution, the molecular shape becomes close to a rigid rod-like form, and crystallization is easy to take place, and therefore, device deterioration is easy to take place under a high-temperature condition. Specifically, it is preferable that the compound represented by the formula (4-1) is a compound represented by the following structure.

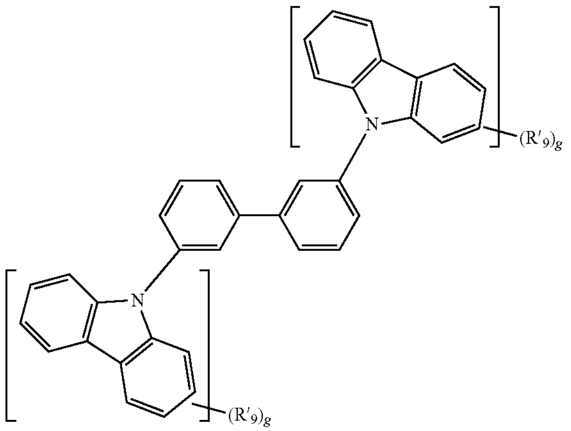

In the foregoing formula, each of $R'_9$s independently represents a substituent; and g represents an integer of from 0 to 8.

In the formula (4-2), from the viewpoint of keeping charge transport capability, f is preferably 2 or more. In the case where f is 2 or 3, from the same viewpoint, it is preferable that $R'_8$s are substituted at the meta-position each other. Specifically, it is preferable that the compound represented by the formula (4-2) is a compound represented by the following structure.

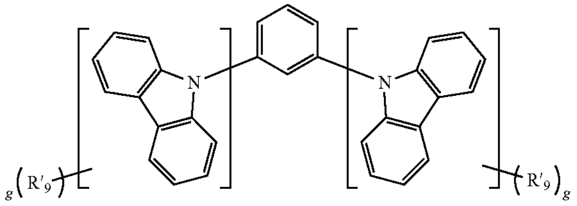

In the foregoing formula, each of $R'_9$s independently represents a substituent; and g represents an integer of from 0 to 8.

In the case where each of the formulae (4-1) and (4-2) has a hydrogen atom, there is included an isotope of hydrogen (for example, a deuterium atom, etc.). In that case, all of the hydrogen atoms in the compound may be replaced by an isotope of hydrogen. Also, the compound represented by each of the formulae (4-1) and (4-2) may be a mixture including a compound in which a part of the hydrogen atoms is an isotope of hydrogen. The compound represented by each of the formulae (4-1) and (4-2) is preferably a compound in which $R'_9$ in the formula (5) is substituted with deuterium, and the following structures are especially preferable.

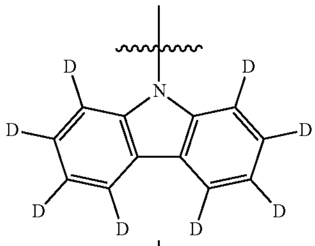

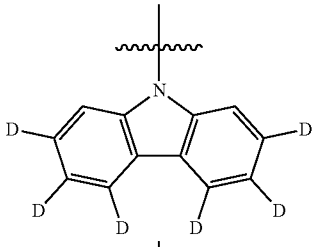

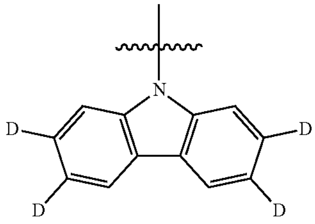

-continued

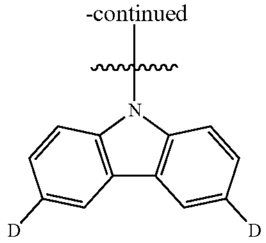

Furthermore, it is expressed that atoms constituting each substituent include isotopes thereof.

It is possible to synthesize the compound represented by each of the formulae (4-1) and (4-2) by a combination of various known synthesis methods. Most generally, with respect to the carbazole compound, there is exemplified a synthesis by the Aza-Cope rearrangement reaction of a condensate of an aryl hydrazine and a cyclohexane derivative and subsequent dehydroaromatization (*Reactions and Syntheses: In the Organic Chemistry*, page 339, written by L. F. Tieze and Th. Eicher, translated by Takano and Ogasawara and published by Nankodo). Also, with respect to a coupling reaction of the obtained carbazole compound and a halogenated aryl compound using a palladium catalyst, there are exemplified the methods described in *Tetrahedron Letters*, Vol. 39, page 617 (1998), ibid., Vol. 39, page 2367 (1998) and ibid., Vol. 40, page 6393 (1999) and so on. The reaction temperature and the reaction time are not particularly limited, and conditions described in the foregoing documents can be applied. Also, with respect to some compounds including mCP, etc., commercially available compounds can be suitably used.

With respect to the compound represented by each of the formulae (4-1) and (4-2) according to the invention, though it is preferable to form a thin layer by a vacuum vapor deposition process, a wet process such as solution coating can also be suitably adopted. From the viewpoints of vapor deposition aptitude and solubility, a molecular weight of the compound represented by each of the formulae (4-1) and (4-2) is preferably not more than 2,000, more preferably not more than 1,200, and especially preferably not more than 800. Also, from the viewpoint of vapor deposition aptitude, when the molecular weight is too low, a vapor pressure is small, change from a gas phase to a solid phase does not take place, and it is difficult to form an organic layer. Therefore, the molecular weight of the compound represented by each of the formulae (4-1) and (4-2) is preferably 250 or more, and especially preferably 300 or more.

The compound represented by each of the formulae (4-1) and (4-2) is a compound having any one of the following structures or a compound obtained by substituting one or more hydrogen atoms thereof with a deuterium atom.

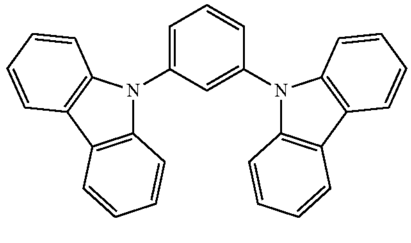

-continued
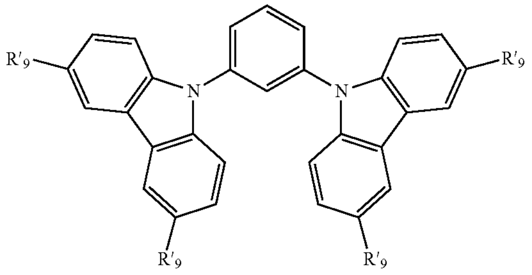
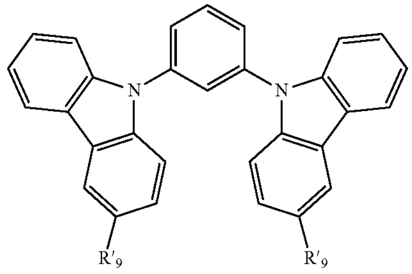
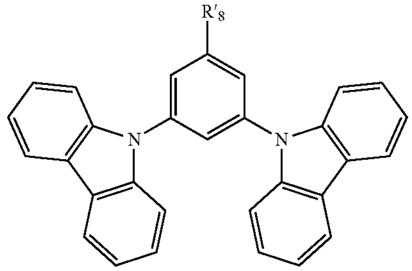
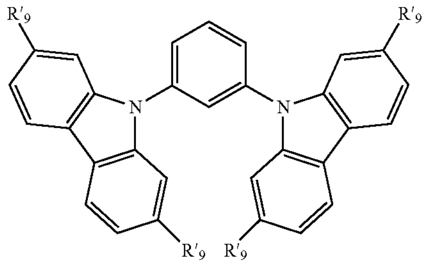
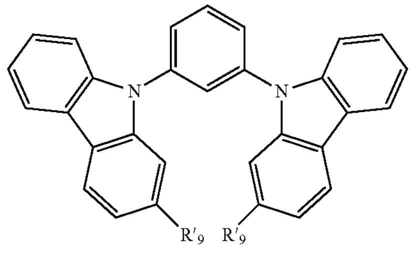
-continued
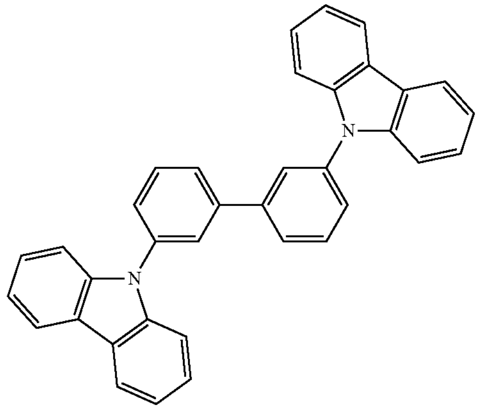
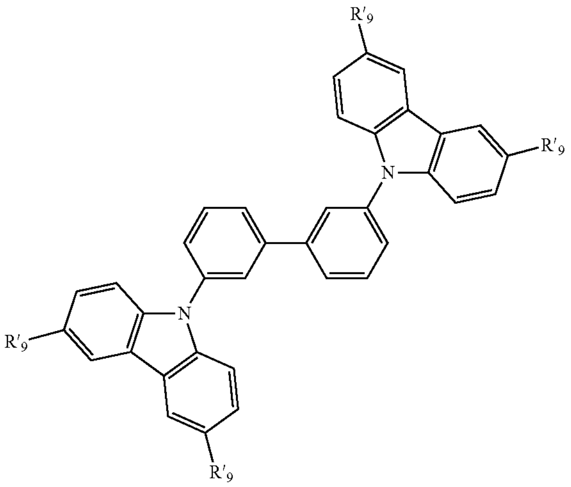
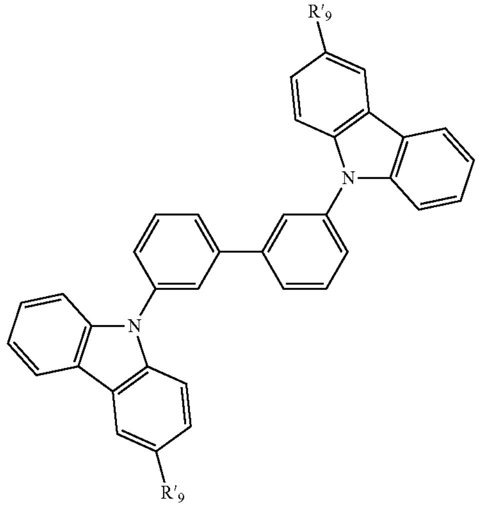

-continued
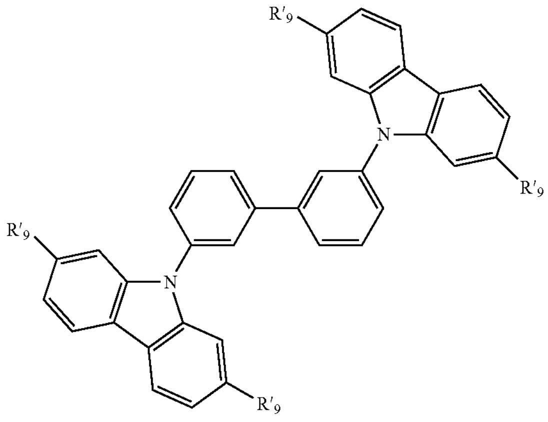
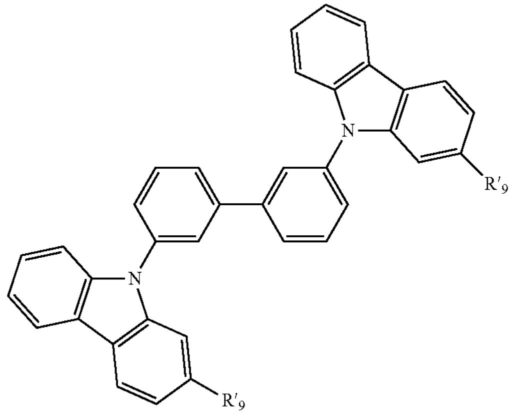
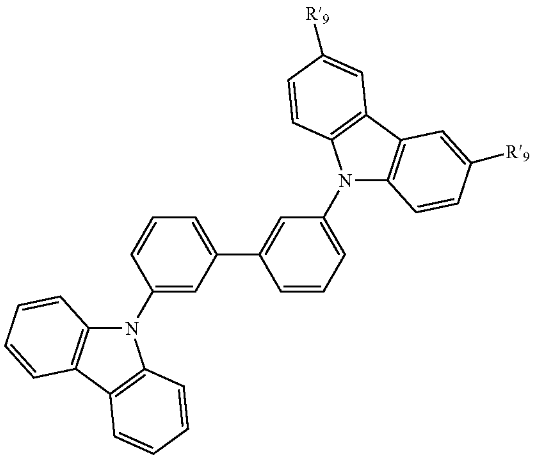
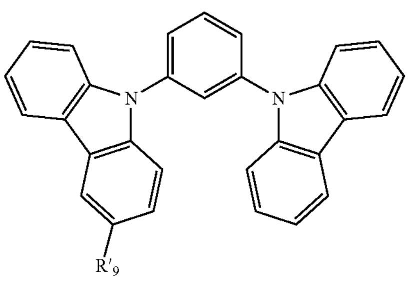
-continued
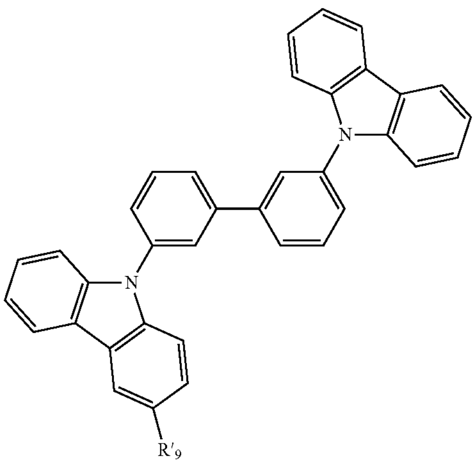
In the foregoing formulae, each of R'$_9$s independently represents a substituent.
Specific examples of the compound represented by each of the formulae (4-1) and (4-2) in the invention are enumerated below, but it should not be construed that the invention is limited thereto.
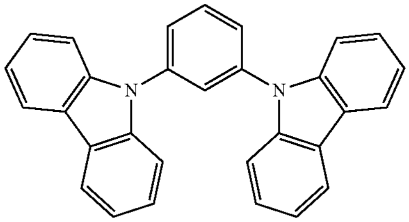
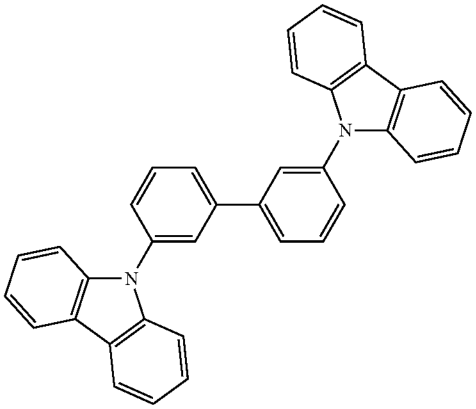
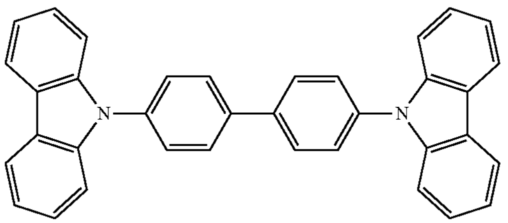

-continued
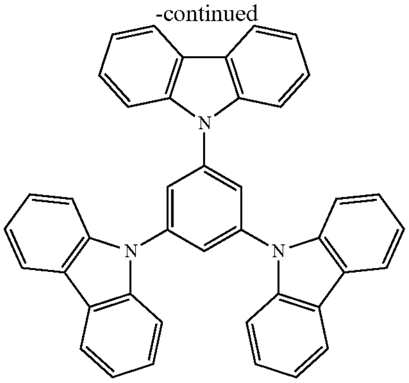
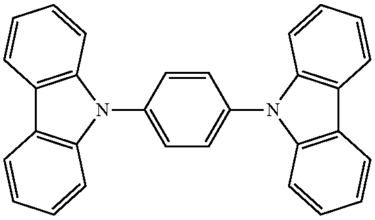
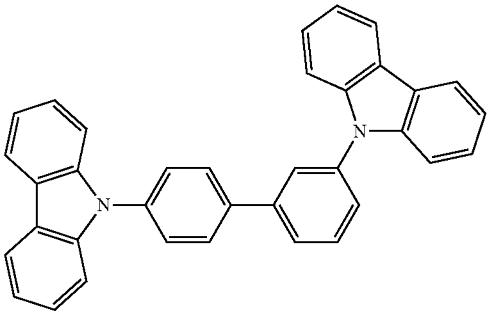
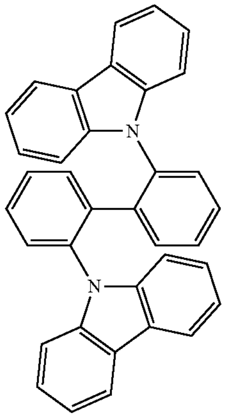
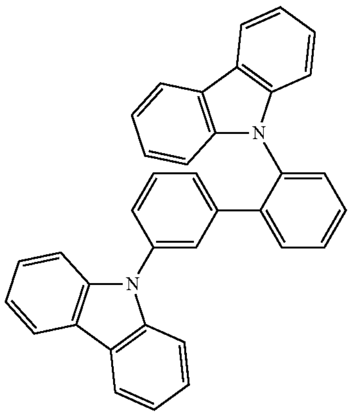
-continued
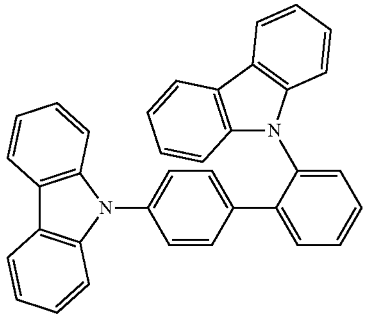
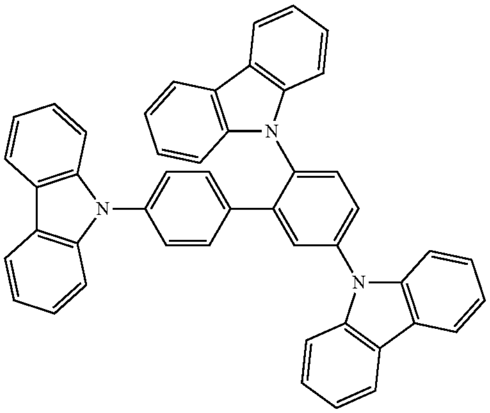
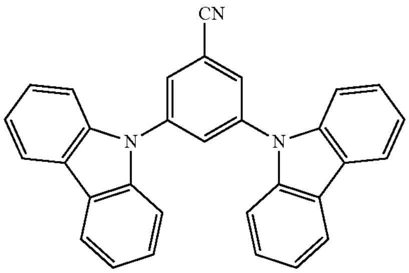
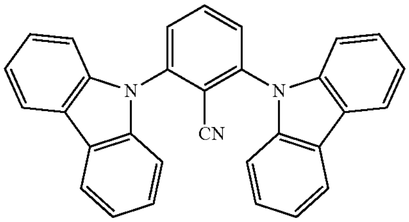
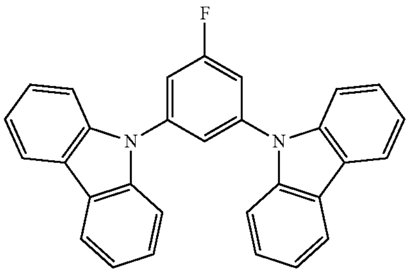
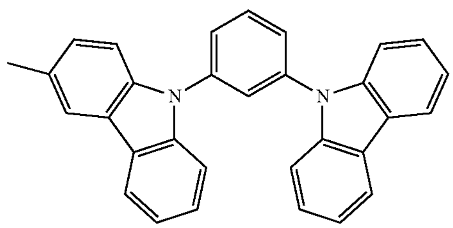

-continued
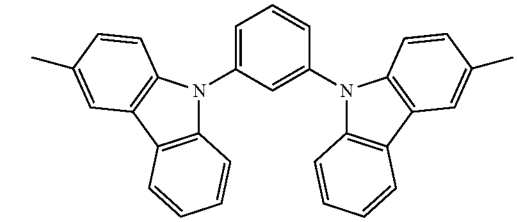
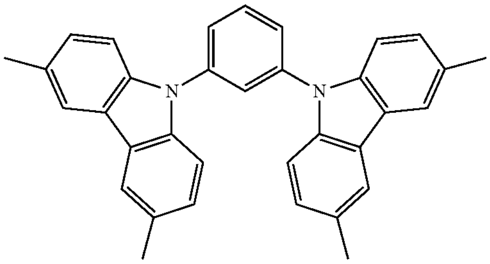
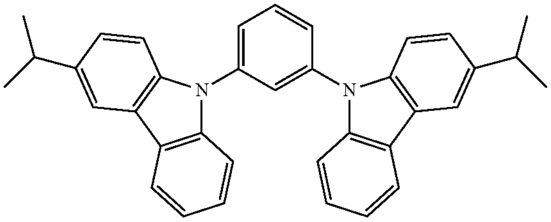
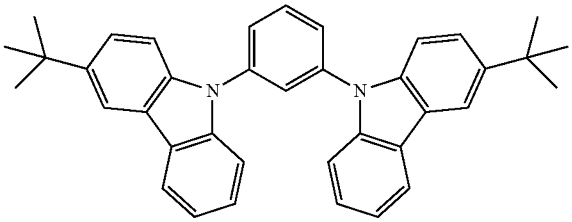
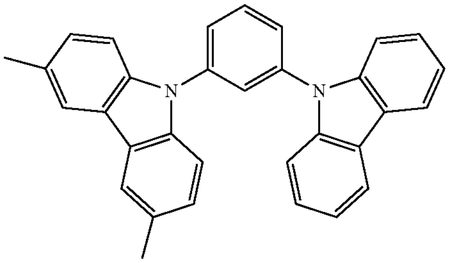
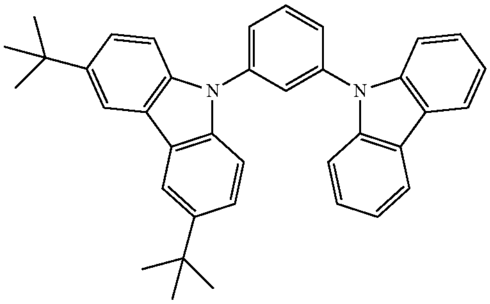
-continued
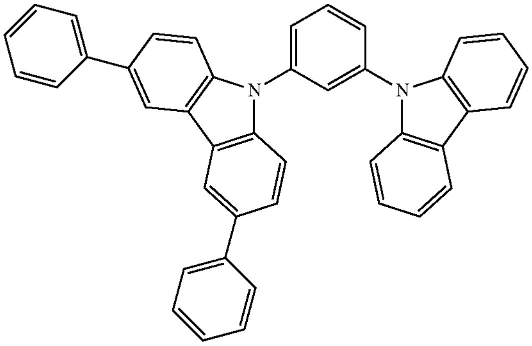
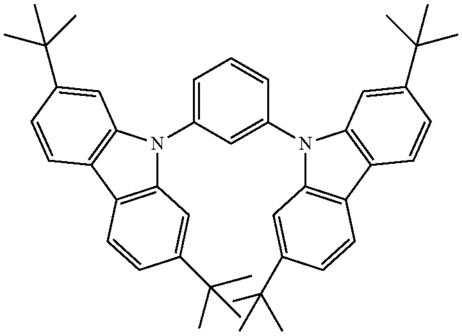
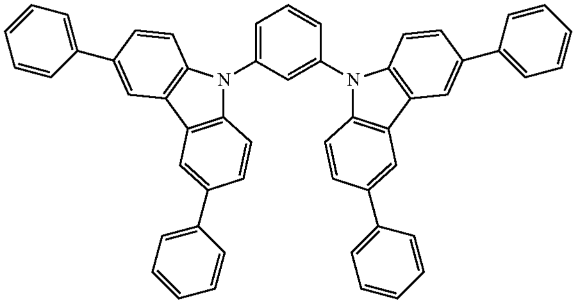
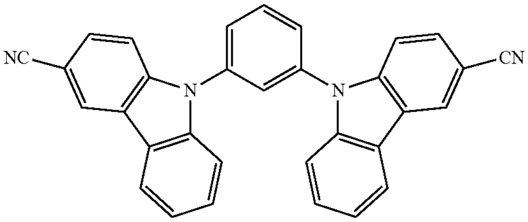
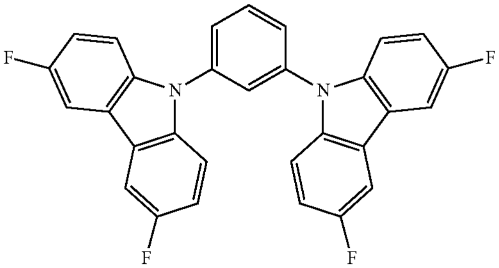
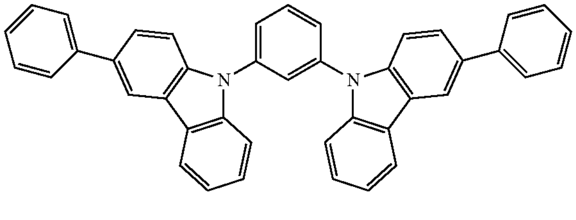

-continued
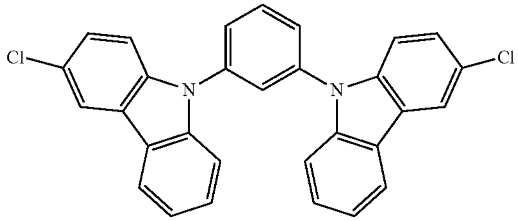
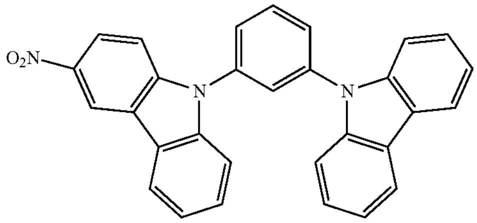
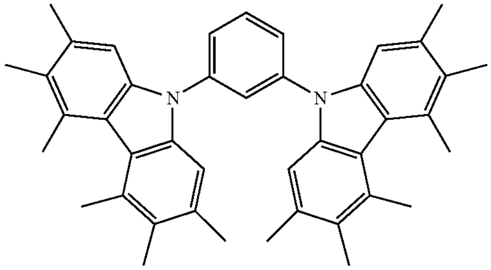
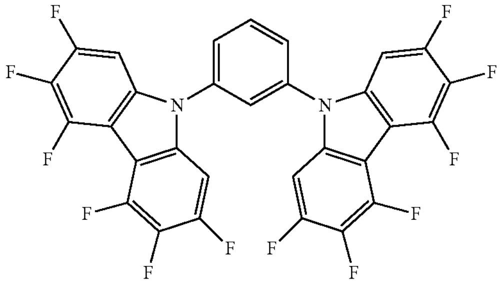
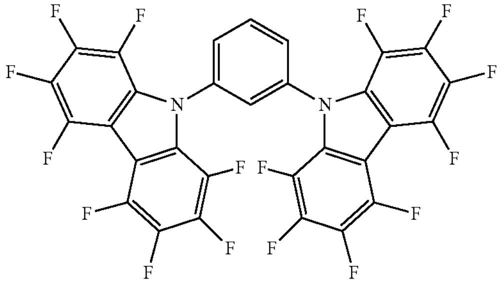
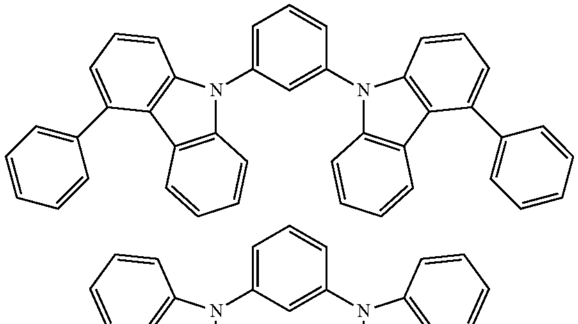
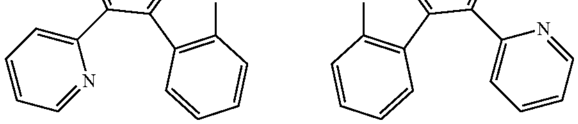
-continued
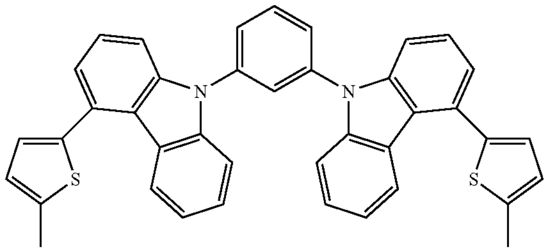
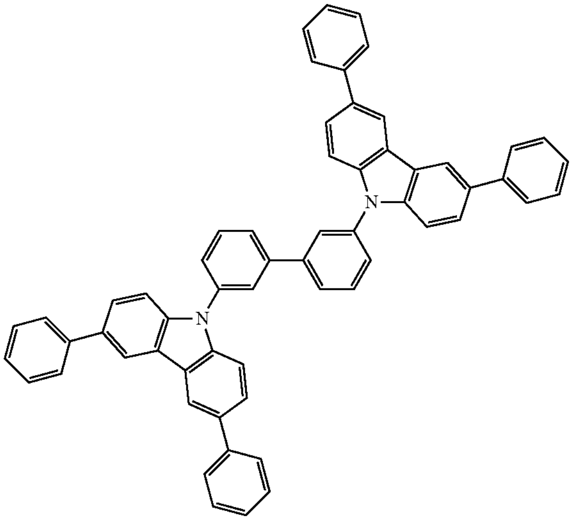
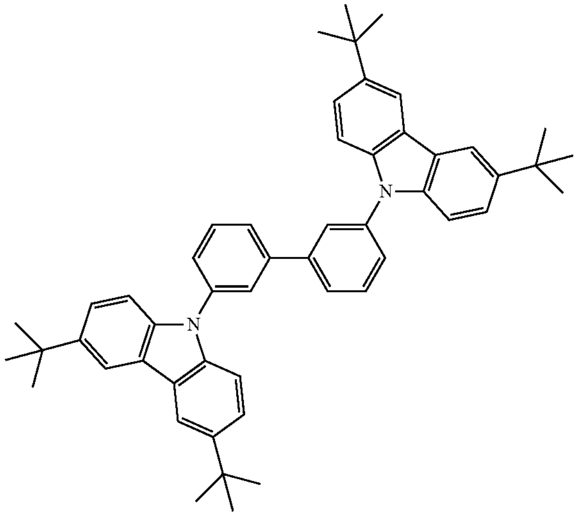

-continued
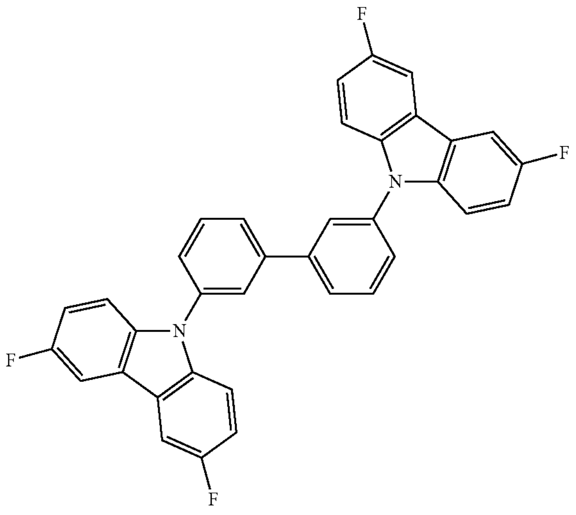
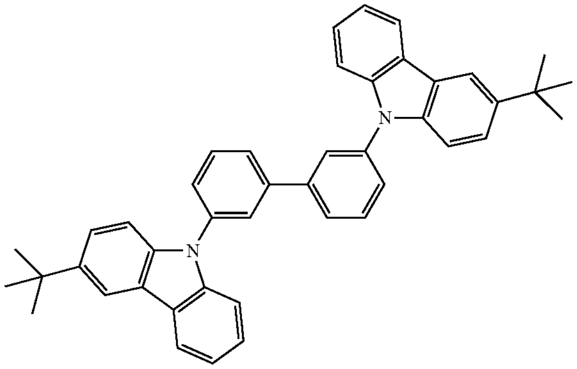
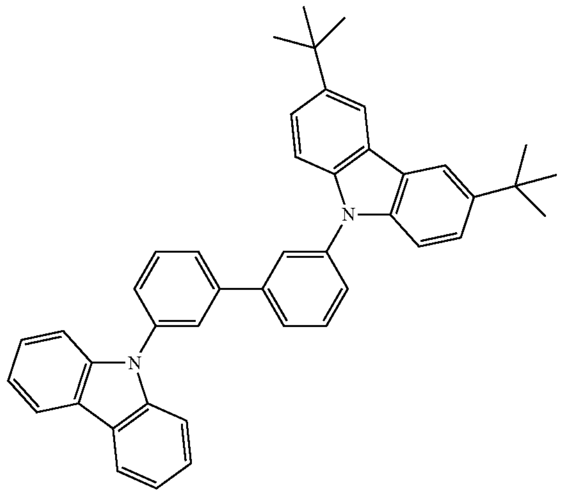
-continued
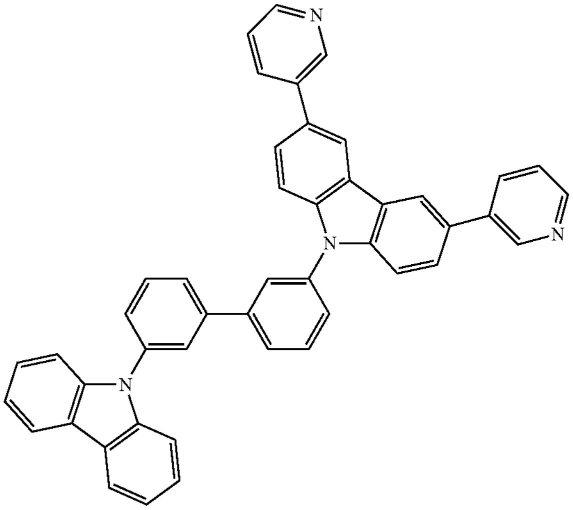
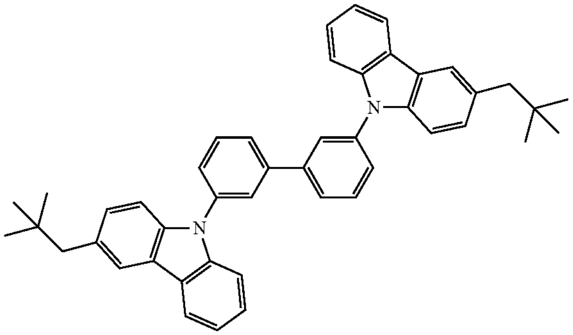
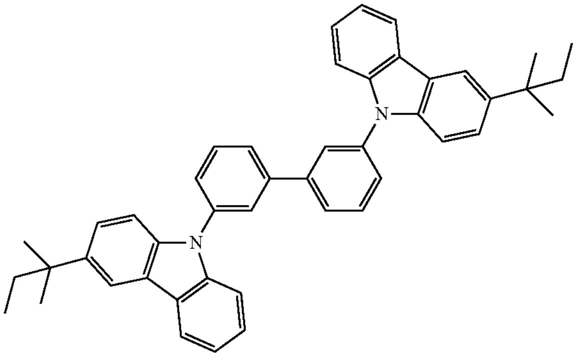
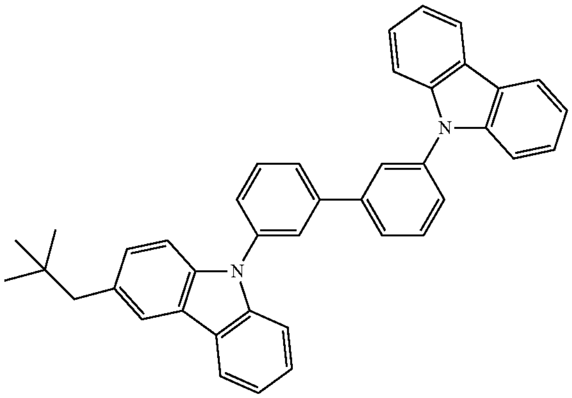

-continued
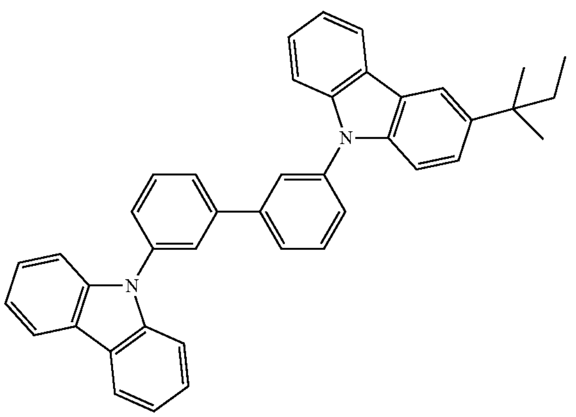
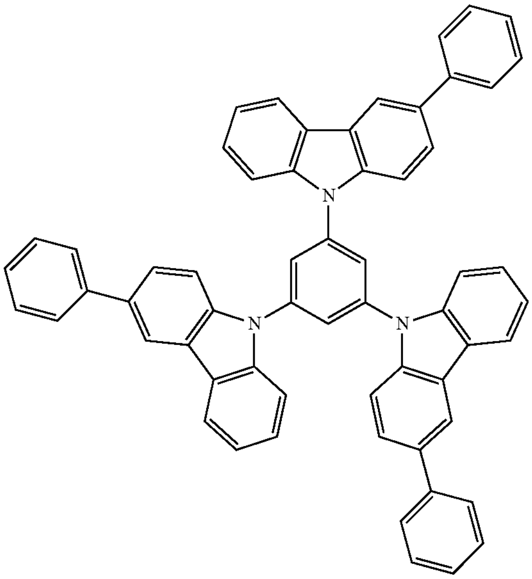
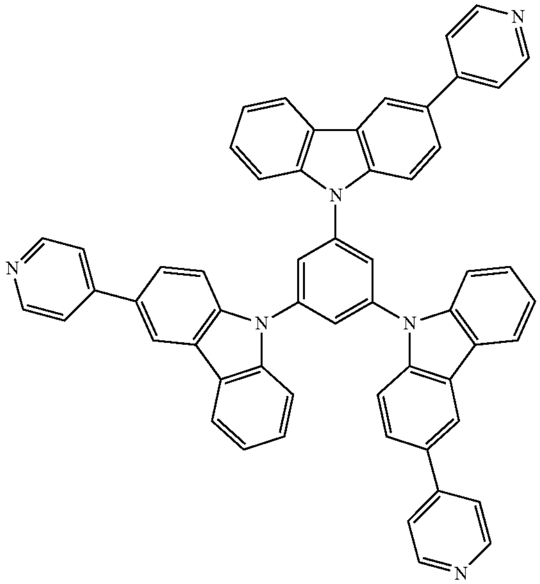
-continued
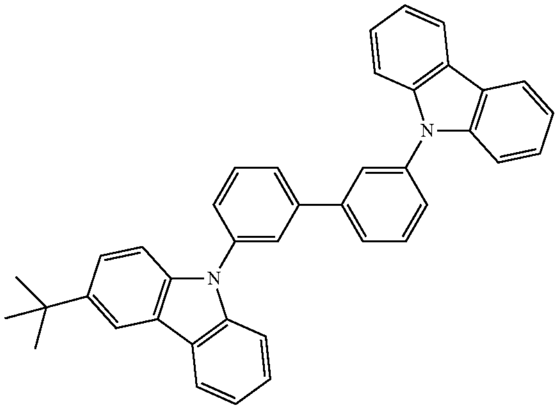
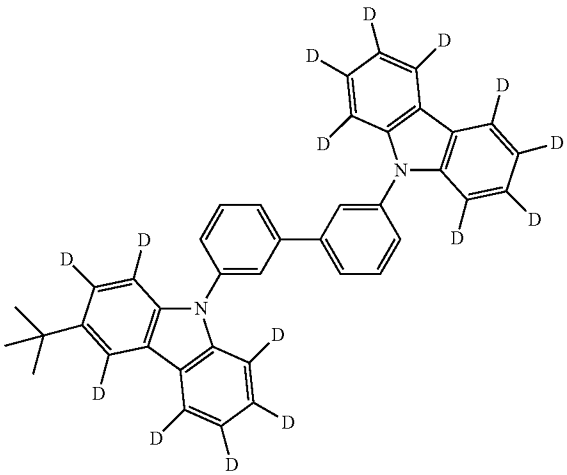
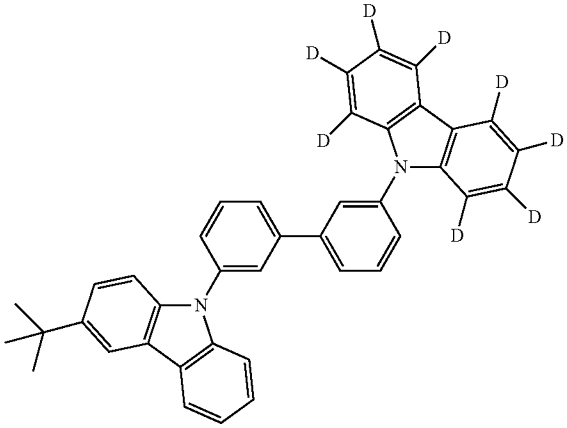
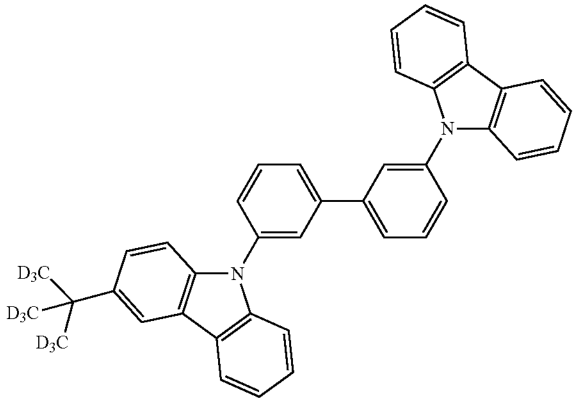

-continued
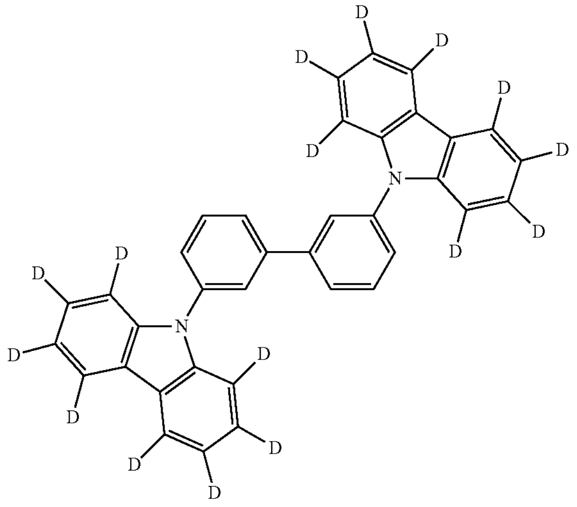 [SMILES: [2H]c1cc2c(c([2H])c1[2H])c1c([2H])c([2H])c([2H])cc1n2-c1cccc(-c2cccc(-n3c4cc([2H])c([2H])c([2H])c4c4c([2H])c([2H])c([2H])cc43)c2)c1]
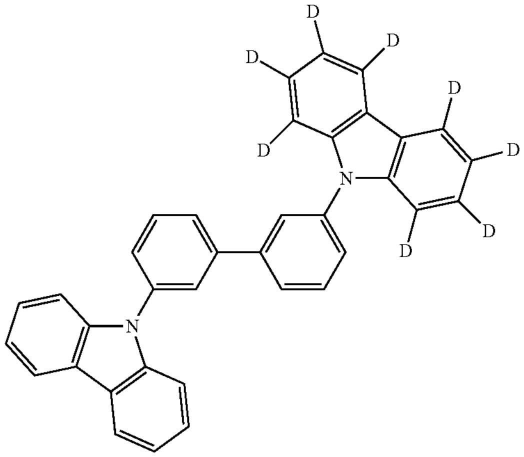
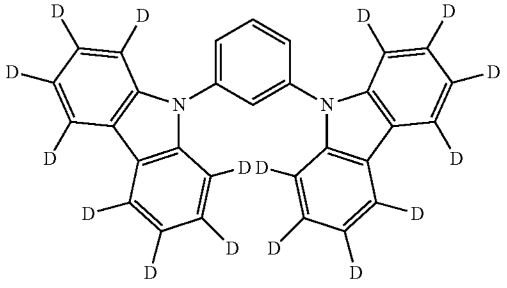
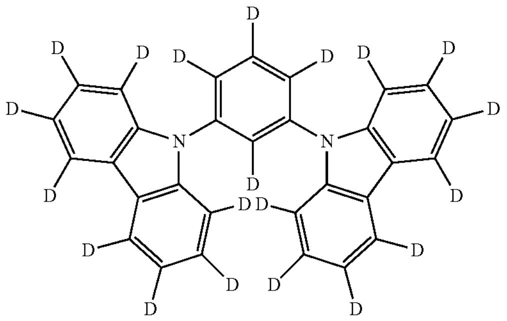
-continued
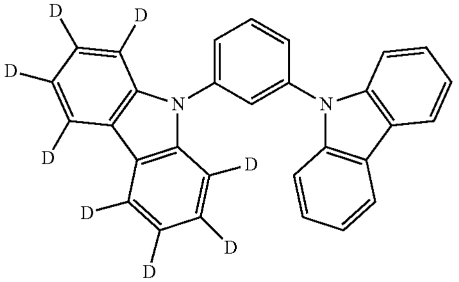
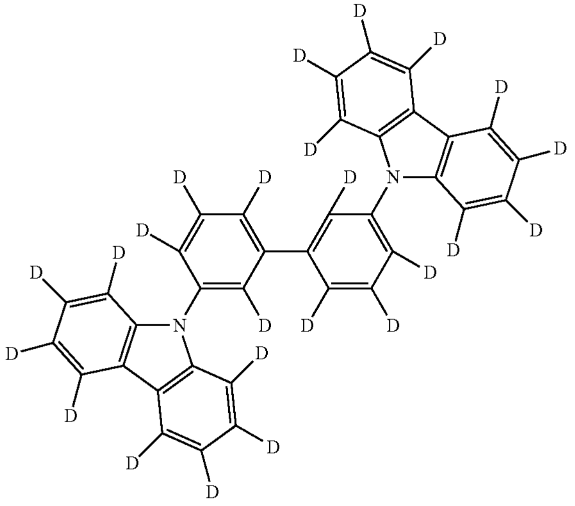
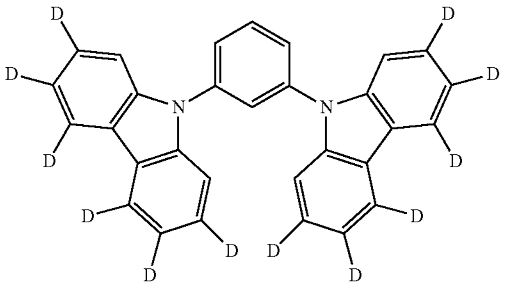
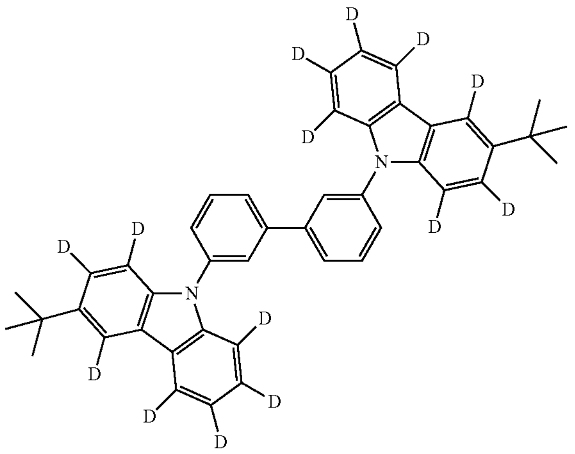

-continued

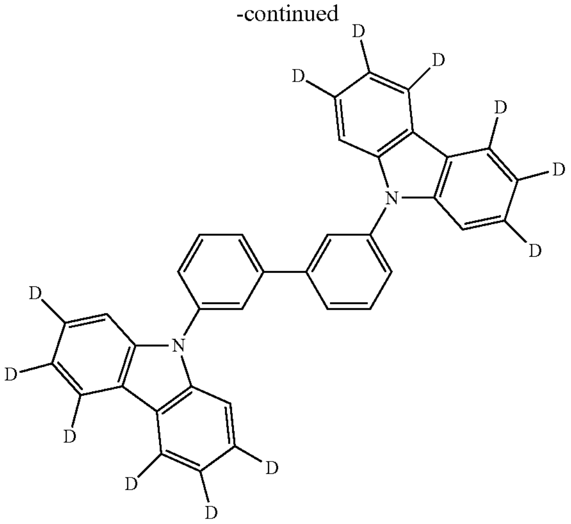

A content of the phosphorescent organometallic complex in the light emitting layer of the invention is preferably from 0.1 to 50% by mass, more preferably from 1 to 40% by mass, and most preferably from 5 to 30% by mass in the light emitting layer. (In this specification, mass ratio is equal to weight ratio.)

A content of the host material (preferably the compound represented by the formula (4-1) or (4-2)) in the light emitting layer of the invention is preferably from 30 to 95% by mass, more preferably from 40 to 95% by mass, further preferably from 50 to 95% by mass, and especially preferably from 70 to 95% by mass.

[Composition Containing the Material for Organic Electroluminescence Device Having a Water Content Before Film Formation of 100 ppm or More and not More than 1,000 ppm]

The invention is also concerned with a composition containing the foregoing material for organic electroluminescence material having a water content before film formation of 100 ppm or more and not more than 1,000 ppm.

A content of the material for organic electroluminescence device having a water content before film formation of 100 ppm or more and not more than 1,000 ppm in the composition of the invention is preferably from 0.1 to 50% by mass, more preferably from 1 to 40% by mass, and most preferably from 5 to 30% by mass.

Other component which may be contained in the composition of the invention may be an organic material or an inorganic material. As the organic material, the host material represented by the formula (4-1) or (4-2), or materials which are exemplified later as other host material, a fluorescent material, a phosphorescent material and a hydrocarbon material can be applied. Of these, a host material and a hydrocarbon material are preferable; and the compound represented by the formula (4-1) or (4-2) is more preferable.

A content of the host material to be contained in the composition of the invention is preferably from 30 to 95% by mass, more preferably from 40 to 95% by mass, further preferably from 50 to 95% by mass, and especially preferably from 70 to 95% by mass.

The composition of the invention can be formed into an organic layer of the organic electroluminescence device by a dry film formation method such as a vapor deposition method and a sputtering method, a transfer method, a printing method or the like.

(Organic Electroluminescence Device)

The device of the invention is described in detail.

The organic electroluminescence device of the invention is an organic electroluminescence device comprising a substrate having thereon a pair of electrodes and at least one organic layer including a light emitting layer between the electrodes, wherein the foregoing material for organic electroluminescence device is used in the at least one organic layer.

In the organic electroluminescence device of the invention, the layer formed of the material for organic electroluminescence device having a water content before film formation of 100 ppm or more and not more than 1,000 ppm is an organic layer, and preferably a light emitting layer, and furthermore, it may have plural organic layers.

In view of the nature of the luminescence device, it is preferable that at least one electrode of an anode and a cathode is transparent or translucent.

FIG. 1 shows an example of a configuration of the organic electroluminescence device according to the invention. In an organic electroluminescence according to the invention shown in FIG. 1, a light emitting layer 6 is interposed between an anode 3 and a cathode 9 on a supporting substrate 2. Specifically, a hole injection layer 4, a hole transport layer 5, the light emitting layer 6, a hole blocking layer 7 and an electron transport layer 8 are laminated in this order between the anode 3 and the cathode 9.

<Configuration of Organic Layer>

The layer configuration of the organic layer is not particularly limited and can be properly selected depending upon an application and a purpose of the organic electroluminescence device. However, it is preferable that the organic layer is formed on the foregoing transparent electrode or a back electrode. In that case, the organic layer is formed entirely or partially on the foregoing transparent electrode or the foregoing back electrode.

The organic layer is not particularly limited with respect to its shape, size and thickness and so on and may be properly selected depending upon its purpose.

Specific examples of the layer configuration are exemplified below, but it should not be construed that the invention is limited to these configurations.

- Anode/hole transport layer/light emitting layer/electron transport layer/cathode
- Anode/hole transport layer/light emitting layer/second electron transport layer (hole blocking layer)/first electron transport layer/cathode
- Anode/hole transport layer/light emitting layer/second electron transport layer (hole blocking layer)/first electron transport layer/electron injection layer/cathode
- Anode/hole injection layer/hole transport layer/light emitting layer/second electron transport layer (hole blocking layer)/first electron transport layer/cathode
- Anode/hole injection layer/hole transport layer/light emitting layer/second electron transport layer (hole blocking layer)/first electron transport layer/electron injection layer/cathode
- Anode/hole injection layer/first hole transport layer/second hole transport layer (electron blocking layer)/light emitting layer/second electron transport layer (hole blocking layer)/first electron transport layer/electron injection layer/cathode The device configuration, substrate, cathode and anode of the organic electroluminescence device are disclosed in detail in, for example, JP-A-2008-270736, and the matters disclosed in this patent document can be applied to the invention.

<Substrate>

It is preferable that the substrate which is used in the invention is a substrate which does not scatter or decay light emitted from the organic layer. In the case of an organic material, it is preferable that the organic material is excellent in heat resistance, dimensional stability, solvent resistance, electric insulating properties and processability.

<Anode>

In general, the anode may have a function as an electrode for feeding a hole into the organic layer. The anode is not particularly limited with respect to its shape, structure and size and so on and can be properly selected among known electrode materials depending upon an application and a purpose of the luminescence device. As described previously, the anode is usually provided as a transparent anode.

<Cathode>

In general, the cathode may have a function as an electrode for injecting an electron into the organic layer. The cathode is not particularly limited with respect to its shape, structure and size and so on and can be properly selected among known electrode materials depending upon an application and a purpose of the luminescence device.

With respect to the substrate, the anode and the cathode, the matters disclosed in paragraphs [0070] to [0089] of JP-A-2008-270736 can be applied to the invention.

<Organic Layer>

The organic layer in the invention is described.

(Formation of Organic Layer)

In the organic electroluminescence device of the invention, each of the organic layers can be suitably formed by any of a dry film formation method such as a vapor deposition method and a sputtering method, a transfer method or a printing method or the like. As the film formation method, a vapor deposition method is preferable.

(Light Emitting Layer)

—Light Emitting Material—

It is preferable that the light emitting layer contains at least one light emitting material.

The light emitting material in the invention is preferably the foregoing material for organic electroluminescence device having a water content before film formation of 100 ppm or more and not more than 1,000 ppm, and more preferably the compound represented by the foregoing formula (E-1). By using the material for organic electroluminescence device having a water content before film formation of 100 ppm or more and not more than 1,000 ppm, inclusion of fine dusts into the material to be caused due to electrification is prevented. As a result, attachment of fine dusts into the device can be prevented; a rate of occurrence of short-circuit device can be reduced; and a yield of the organic electroluminescence device can be enhanced. Also, occurrence of cloudiness of the device can be suppressed, and storage stability can be enhanced.

In general, a content of the light emitting material in the light emitting layer is preferably from 0.1% by mass to 50% by mass, more preferably from 1 to 40% by mass, and most preferably from 5 to 30% by mass relative to the mass of all of the compounds capable of forming the light emitting layer in the light emitting layer.

Though a thickness of the light emitting layer is not particularly limited, in general, it is preferably from 2 nm to 500 nm. From the viewpoint of external quantum efficiency, the thickness of the light emitting layer is more preferably from 3 nm to 200 nm, and further preferably from 5 nm to 100 nm.

The light emitting material may be any of a fluorescent material or a phosphorescent material, and from the viewpoint that a device with higher efficiency is obtainable, the light emitting material is preferably a phosphorescent material, and more preferably an organometallic complex type phosphorescent material represented by any one of the foregoing (E-1) to (E-4) or the foregoing formula (PQ-1). The light emitting material may be made of a single kind or two or more kinds thereof.

Fluorescent Material:

Examples of the fluorescent material which can be used in the invention include compounds, for example, benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, condensed aromatic compounds, perinone derivatives, oxadiazole derivatives, oxazine derivatives, aldazine derivatives, pyralizine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, diketopyrrolopyrrole derivatives, aromatic dimethylidine compounds, various complexes represented by complexes of 8-quinolinol derivatives and complexes of pyrromethene derivatives, polymer compounds such as polythiophene, polyphenylene and polyphenylene vinylene, organic silane derivatives, etc.

Phosphorescent Material:

Examples of the phosphorescent material which can be used in the invention include phosphorescent compounds disclosed in patent documents, for example, U.S. Pat. No. 6,303,238B1, U.S. Pat. No. 6,097,147, WO 00/57676, WO 00/70655, WO 01/08230, WO 01/39234A2, WO 01/41512A1, WO 02/02714A2, WO 02/15645A1, WO 02/44189A1, WO 05/19373A2, JP-A-2001-247859, JP-A-2002-302671, JP-A-2002-117978, JP-A-2003-133074, JP-A-2002-235076, JP-A-2003-123982, JP-A-2002-170684, EP 1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, JP-A-2007-96259, etc. Above all, more preferred examples of the light emitting dopant include Ir complexes, Pt complexes, Cu complexes, Re complexes, W complexes, Rh complexes, Ru complexes, Pd complexes, Os complexes, Eu complexes, Tb complexes, Gd complexes, Dy complexes and Ce complexes. In particular, Ir complexes, Pt complexes and Re complexes are preferable; and Ir complexes, Pt complexes and Re complexes each of which contains at least one coordination mode of a metal-carbon bond, a metal-nitrogen bond, a metal-oxygen bond and a metal-sulfur bond are more preferable. Furthermore, from the viewpoints of luminous efficiency, driving durability, chromaticity, etc., Ir complexes, Pt complexes and Re complexes each of which contains a tridentate or multidentate ligand are especially preferable.

A content of the phosphorescent material is preferably in the range of 0.1% by mass or more and not more than 50% by mass, more preferably in the range of 1% by mass or more and not more than 40% by mass, and most preferably in the range of 5% by mass and not more than 30% by mass relative to the total mass of the light emitting layer.

A content of the phosphorescent material (the compound represented by the formula (E-1) and/or the phosphorescent material to be jointly used) which can be used in the invention is preferably in the range of 0.1% by mass or more and not more than 50% by mass, more preferably in the range of 1% by mass or more and not more than 40% by mass, and most preferably in the range of 5% by mass and not more than 30% by mass relative to the total mass of the light emitting layer. In particular, when the content of the phosphorescent material is in the range of 5% by mass and not more than 30% by mass relative to the total mass of the light emitting layer, the chromaticity of light emission of the organic electroluminescence device is small with respect to the dependency on the addition concentration of the phosphorescent material.

In the organic electroluminescence device of the invention, it is the most preferable that at least one kind of the compound represented by the formula (E-1) or the compound represented by the formula (PQ-1) is contained in an amount of from 5 to 30% by mass relative to the total mass of the light emitting layer.

—Host Material—

The light emitting layer in the device of the invention may be constituted of only a light emitting material, or may be constituted of a mixed layer of a host material and a light emitting material. It is preferable that the host material is a charge transport material. The host material may be made of a single kind or two or more kinds thereof. For example, there is exemplified a configuration of a mixture of an electron transporting host material and a hole transporting host material. Furthermore, a material which does not have charge transporting properties and which does not undergo light emission may be contained in the light emitting layer. Though the compound represented by the formula (4-1) or (4-2) is preferable as the host material which is used in the invention, the following compounds may be further contained as the host material. That is, there can be exemplified pyrrole, indole, carbazole, CBP (4,4'-di(9-carbazoyl)biphenyl)), azaindole, azacarbazole, triazole, oxazole, oxadiazole, pyrazole, imidazole, thiophene, polyarylalkanes, pyrazoline, pyrazolone, phenylenediamine, arylamines, amino-substituted chalcone, styrylanthracene, fluorenone, hydrazone, stilbene, silazane, aromatic tertiary amine compounds, styrylamine compounds, porphyrin based compounds, polysilane based compounds, poly(N-vinylcarbazole), aniline based copolymers, thiophene oligomers, conductive high-molecular weight oligomers such as polythiophene, organic silanes, carbon films, pyridine, pyrimidine, triazine, imidazole, pyrazole, triazole, oxazole, oxadiazole, fluorenone, anthraquinodimethane, anthrone, diphenylquinone, thiopyrane dioxide, carbodiimide, fluorenylidenemethane, distyrylpyrazine, fluorine-substituted aromatic compounds, heterocyclic tetracarboxylic acid anhydrides such as naphthaleneperillene, phthalocyanine, metal complexes of an 8-quinolinol derivative, metal phthalocyanines, various metal complexes represented by metal complexes containing benzoxazole or benzothiazole as a ligand and derivatives thereof (may have a substituent or a condensed ring).

In the light emitting layer in the invention, from the standpoints of color purity, luminous efficiency and driving durability, it is preferable that the lowest excited triplet energy ($T_1$ energy) of the host material (also including the compound represented by the formula (4-1) or (4-2)) is higher than the $T_1$ energy of the foregoing phosphorescent material.

Also, though a content of the host compound in the invention is not particularly limited, from the viewpoints of luminous efficiency and driving voltage, it is preferably 15% by mass or more and not more than 95% by mass relative to the mass of all of the compounds capable of forming the light emitting layer.

As the light emitting layer in the device of the invention, one using, as a host material, the compound represented by the formula (4-1) or (4-2) and, as a light emitting material, the material for organic electroluminescent device having a water content before film formation of 100 ppm or more and not more than 1,000 ppm, and preferably the compound represented by the formula (E-1) is preferable.

Also, the light emitting layer may be made of a single layer or multiple layers of two or more layers. In the case where the light emitting layer is made of plural layers, the compound represented by the formula (4-1) or (4-2) and the material for organic electroluminescent device having a water content before film formation of 100 ppm or more and not more than 1,000 ppm may be contained in the two or more light emitting layers. Also, the respective light emitting layers may undergo light emission in a different luminescent color from each other.

—Hole Injection Layer and Hole Transport Layer—

Each of the hole injection layer and the hole transport layer is a layer having a function of accepting a hole from the anode or the anode side to transport it into the cathode side.

—Electron Injection Layer and Electron Transport Layer—

Each of the electron injection layer and the electron transport layer is a layer having a function of accepting an electron from the cathode or the cathode side to transport it into the anode side.

With respect to the hole injection layer, the hole transport layer, the electron injection layer and the electron transport layer, the matters disclosed in paragraphs [0165] to [0167] of JP-A-2008-270736 can be applied to the invention.

—Hole Blocking Layer—

The hole blocking layer is a layer having a function of preventing permeation of the hole having been transported from the anode side to the light emitting layer into the cathode side from occurring. In the invention, the hole blocking layer can be provided as an organic layer adjacent to the light emitting layer on the cathode side.

As an example of an organic compound constituting the hole blocking layer, for example, those exemplified previously as the hole transport material can be applied. Examples of the organic compound constituting the hole blocking layer include aluminum complexes such as aluminum(III)bis(2-methyl-8-quinolinato)4-phenylphenolate (abbreviated as "BAlq"); triazole derivatives; and phenanthroline derivatives such as 2,9-dimethyl-4,7-diphenyl-1,10-phenanthroline (abbreviated as "BCP").

A thickness of the hole blocking layer is preferably from 1 nm to 500 nm, more preferably from 5 nm to 200 nm, and further preferably from 10 nm to 100 nm The hole blocking layer may be of a single-layered structure composed of one or two or more kinds of the foregoing materials, or may be of a multilayered structure composed of a plurality of layers of the same composition as or a different composition from each other.

—Electron Blocking Layer—

The electron blocking layer is a layer having a function of preventing permeation of an electron having been transported from the cathode side to the light emitting layer into the anode side from occurring. In the invention, the electron blocking layer can be provided as an organic layer adjacent to the light emitting layer on the anode side.

As an example of an organic compound constituting the electron blocking layer, for example, those exemplified previously as the hole transport material can be applied.

A thickness of the electron blocking layer is preferably from 1 nm to 500 nm, more preferably from 5 nm to 200 nm, and further more preferably from 10 nm to 100 nm.

The electron blocking layer may be of a single-layered structure composed of one or two or more kinds of the foregoing materials, or may be of a multilayered structure composed of a plurality of layers of the same composition as or a different composition from each other.

<Protective Layer>

In the invention, the whole of the organic electroluminescence device may be protected by a protective layer.

With respect to the protective layer, the matters disclosed in paragraphs [0169] to [0170] of JP-A-2008-270736 can be applied to the invention.

<Sealing Vessel>

In the device of the invention, the whole of the device may be sealed using a sealing vessel.

With respect to the sealing vessel, the matters disclosed in paragraph [0171] of JP-A-2008-270736 can be applied to the invention.

[Film Formation Method]

In the invention, it is preferable that the light emitting layer is subjected to film formation by simultaneously heating the compound represented by the formula (4-1) or (4-2) and the material for organic electroluminescence device having a water content before film formation of 100 ppm or more and not more than 1,000 ppm, thereby achieving sublimation and vapor deposition.

During the film formation, it is preferable to mix the compound represented by the formula (4-1) or (4-2) and the material for organic electroluminescence device having a water content before film formation of 100 ppm or more and not more than 1,000 ppm, and the composition of the invention may be used. With respect to a content proportion of the compound represented by the formula (4-1) or (4-2) and the material for organic electroluminescence device having a water content before film formation of 100 ppm or more and not more than 1,000 ppm, a ratio of the material for organic electroluminescence device having a water content before film formation of 100 ppm or more and not more than 1,000 ppm to the compound represented by the formula (4-1) or (4-2) is preferably in the range of 0.1% by mass or more and not more than 50% by mass, more preferably in the range of 1% by mass or more and not more than 40% by mass, and most preferably in the range of 5% by mass or more and not more than 30% by mass.

A temperature of heating in the vapor deposition is preferably from 200° C. to 400° C., and more preferably from 250° C. to 320° C.

A time of heating in the vapor deposition is preferably 0.1 hours to 350 hours, and more preferably from 0.1 hours to 150 hours.

According to the film formation method of the invention, there is an advantage that a light emitting film which is high in efficiency and durability and small in a color change at the time of high-temperature driving can be easily prepared.

[Driving]

According to the organic electroluminescence device of the invention, light emission can be obtained by impressing a voltage of direct current (optionally including an alternating current component) (usually from 2 volts to 15 volts) or a current of direct current between the anode and the cathode.

As to the driving method of the organic electroluminescence device of the invention, driving methods disclosed in JP-A-2-148687, JP-A-6-301355, JP-A-5-29080, JP-A-7-134558, JP-A-8-234685, JP-A-8-241047, Japanese Patent No. 2784615 and U.S. Pat. Nos. 5,828,429 and 6,023,308 can be applied.

In the luminescence device of the invention, a light collecting efficiency can be enhanced by various known ways and means. For example, it is possible to enhance the light collecting efficiency and to enhance the external quantum efficiency by processing a surface shape of the substrate (for example, forming a fine uneven pattern), controlling a refractive index of each of the substrate, the ITO layer and the organic layer, controlling a thickness of each of the substrate, the ITO layer and the organic layer, or the like.

The external quantum efficiency of the luminescence device of the invention is preferably 5% or more and not more than 100%, more preferably 10% or more and not more than 100%, further preferably 15% or more and not more than 100%, and especially preferably 20% or more and not more than 30%. With respect to the numerical value of the external quantum efficiency, a maximum value of the external quantum efficiency at the time of driving the device at 20° C., or a value of the external quantum efficiency in the vicinity of from 100 to 2,000 cd/$m^2$ at the time of driving the device at 20° C., can be employed.

The luminescence device of the invention may be of a so-called top emission mode for collecting light emission from the anode side.

The organic electroluminescence device in the invention may have a resonator structure. For example, the organic electroluminescence device in the invention includes a transparent substrate having a multilayered film mirror composed of plural laminated films having a different refractive index from each other, a transparent or translucent electrode, a light emitting layer and a metal electrode superimposed thereon. The light emitted in the light emitting layer repeats reflection between the multilayered film mirror and the metal electrode while making them function as a reflector and resonates.

In another preferred embodiment, each of a transparent or translucent electrode and a metal electrode functions as a reflector on a transparent substrate, and the light emitted in the light emitting layer repeats reflection therebetween and resonates.

In order to form a resonator structure, an optical path length which is determined from effective refractive indexes of the two reflectors and a refractive index and a thickness of each layer between the reflectors is regulated so as to have an optimal value for the purpose of obtaining a desired resonance wavelength. A calculation expression of the case of the first embodiment is disclosed in JP-A-9-180883. A calculation expression of the case of the second embodiment is disclosed in JP-A-2004-127795.

The invention is also concerned with a method for manufacturing an organic electroluminescence device using the foregoing material for organic electroluminescence device. That is, the method is a method for manufacturing a device comprising using an organic material having a water content, as measured before film formation, of 100 ppm or more and not more than 1,000 ppm as a material to be used for an organic electroluminescence device.

The invention is also concerned with a method for reducing a rate of occurrence of short-circuit device using the foregoing material for organic electroluminescence device. That is, the invention is a method for reducing a rate of occurrence of short-circuit device comprising using an organic material having a water content, as measured before film formation, of 100 ppm or more and not more than 1,000 ppm as a material to be used for an organic electroluminescence device.

(Application of Luminescence Device of the Invention)

The luminescence device of the invention can be suitably utilized for light emission apparatuses, pixels, display devices, displays, backlights, electro-photographs, illumination light sources, recording light sources, exposure light sources, read light sources, markers, signboards, interiors, optical communications and so on. In particular, the luminescence device of the invention is preferably used for devices which are driven in a region with high brightness, such as illumination apparatuses and display apparatuses.

Next, the light emission apparatus of the invention is described by reference to FIG. 2.

The light emission apparatus of the invention is one using the foregoing organic electroluminescence device.

Figure 2:
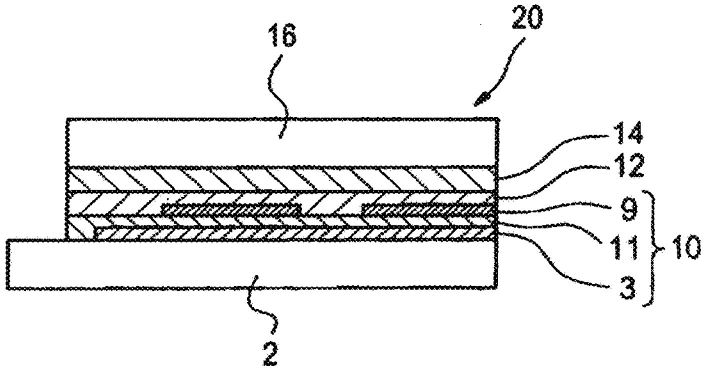
FIG. 2 is a diagrammatic view showing an example of a light emission apparatus according to the invention.

FIG. 2 is a sectional view diagrammatically showing an example of the light emission apparatus of the invention.

A light emission apparatus 20 of FIG. 2 is configured to include a transparent substrate (supporting substrate) 2, an organic electroluminescence device 10, a sealing vessel 16 and so on.

The organic electroluminescence device 10 is configured in such a manner that an anode (first electrode) 3, an organic layer 11 and a cathode (second electrode) 9 are laminated in this order on the substrate 2. Also, a protective layer 12 is laminated on the cathode 9, and furthermore, the sealing vessel 16 is provided on the protective layer 12 via an adhesive layer 14. In this respect, a part of each of the electrodes 3 and 9, a partition, an insulating layer and the like are omitted.

Here, a photocurable adhesive or a thermosetting adhesive such as an epoxy resin can be used as the adhesive layer 14, and for example, a thermosetting adhesive sheet can also be used.

The application of the light emission apparatus of the invention is not particularly limited, and examples thereof include, in addition to illumination apparatuses, display apparatuses of television receiver, personal computer, mobile phone, electronic paper, etc.

Next, the illumination apparatus according to an embodiment of the invention is described by reference to FIG. 3.

Figure 3:
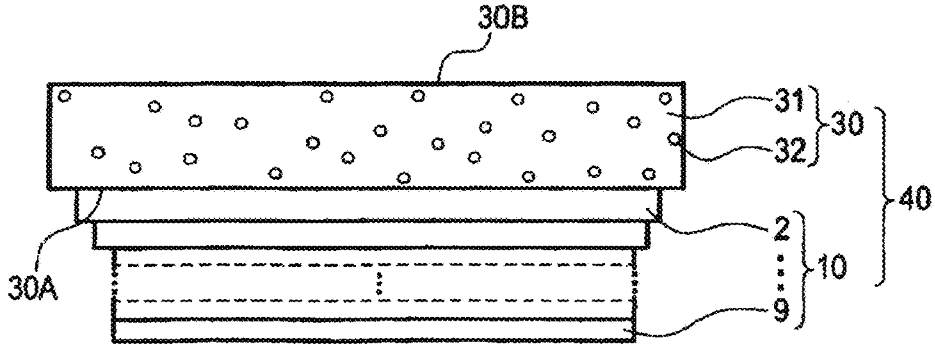
FIG. 3 is a diagrammatic view showing an example of an illumination apparatus according to the invention.

FIG. 3 is a sectional view diagrammatically showing an example of the illumination apparatus according to an embodiment of the invention.

As shown in FIG. 3, an illumination apparatus 40 according to an embodiment of the invention is provided with the foregoing organic EL device 10 and a light scattering member 30. More specifically, the illumination apparatus 40 is configured in such a manner that the substrate 2 of the organic EL device 10 and the light scattering member 30 come into contact with each other.

The light scattering member 30 is not particularly limited so far as it is able to scatter light. In FIG. 3, the light scattering member 30 works as a member having a fine particle 32 dispersed in a transparent substrate 31. As the transparent substrate 31, for example, a glass substrate can be suitably exemplified. As the fine particle 32, a transparent resin fine particle can be suitably exemplified. As each of the glass substrate and the transparent resin fine particle, those which are known can be used. Such illumination apparatus 40 is an apparatus which when light emission from the organic electroluminescence device 10 is made incident into a light incident surface 30A of the light scattering member 30, scatters the incident light by the light scattering member 30 and outputs the scattered light as illumination light from a light outgoing surface 30B.

EXAMPLES

The invention is more specifically described below by reference to the following Examples, but it should not be construed that the scope of the invention is limited to those Examples.

Examples 1 to 22

All of materials used for the preparation of a device were subjected to sublimation purification and confirmed to have a purity (absorption intensity area ratio at 254 nm) of 99.9% or more by means of high-performance liquid chromatography (TSKgel ODS-110Z, manufactured by Tosoh Corporation).

An indium tin oxide (ITO) film-provided glass substrate having a thickness of 0.5 mm and a size of 2.5 cm in square (manufactured by GEOMATEC Corporation, surface resistance: 10Ω/□) was put in a washing vessel, ultrasonically washed in 2-propanol and then subjected to a UV-ozone treatment for 30 minutes. The following organic layers were successively vapor deposited on this transparent anode (ITO film) by means of vacuum vapor deposition so as to have each of device configurations shown in Tables 1 to 22.

The devices described in each of Tables 1 to 22 had the same device configuration, except for changing a water content before film formation of a compound as an objective material, as measured by the following method. The water content was regulated by the addition of water so as to have a value shown in each of Tables 1 to 22. For example, the "water content" in Table 1 is a value obtained by measuring a water content of Compound 1 as the "objective material" before film formation by the following method. A symbol "<" in the column of "Water content" in each of Tables 1 to 22 means a sign of inequality, and for example, "<5 ppm" means that the water content of a compound as the "objective material" before film formation is less than 5 ppm.

For example, the terms "Device configuration: ITO/CuPc (10)/NPD (30)/CBP+8% Compound 1 (30)/BAlq (10)/Alq (30)/LiF (0.1)/Al (100)" in Table 1 mean that CuPc (film thickness: 10 nm); NPD (film thickness: 30 nm); a mixture of 8% by mass of Compound 1 and 92% by mass of CBP (film thickness: 30 nm); BAlq (film thickness: 10 nm); Alq (film thickness: 30 nm); LiF (film thickness: 0.1 nm); and Al (film thickness: 100 nm) were laminated in this order on the ITO film.

The obtained laminate was placed in a nitrogen gas-purged glove box without being exposed to the air and sealed using a stainless steel-made sealing can and an ultraviolet ray-curable adhesive (XNR5516HV, manufactured by Nagase-CHIBA Ltd.), thereby obtaining each of devices shown in Tables 1 to 22.

(Water Content of Material for Organic Electroluminescence Device)

With respect to a material as the objective material, from 30 minutes to 2 hours before putting into a vapor deposition machine, by using a Karl Fischer trace moisture meter (CA-200, manufactured by Mitsubishi Chemical Analytech Co., Ltd.), the material was heated to 140° C. by a water vaporizer (VA-200, manufactured by Mitsubishi Chemical Analytech Co., Ltd.), and vaporized moisture was sent to a titration cell with dry $N_2$ at a flow rate of 250 mL/min, thereby measuring a water content of the material for organic electroluminescence device.

A material as the objective material was preserved so as not to change in the water content from the measurement of the water content to being put into a vapor deposition machine.

(Performance Evaluation of Organic Electroluminescence Device)

The performance of each of the obtained devices was evaluated.

<Device Evaluation>

(a) External Quantum Efficiency:

Each of the devices was subjected to light emission upon being impressed with a direct current voltage using a source measure unit MODEL 2400, manufactured by Toyo Corporation. Its brightness was measured using a brightness meter BM-8, manufactured by Topcon Corporation. An emission spectrum and a light emission wavelength were measured using a spectral analyzer PMA-11, manufactured by Hamamatsu Photonics K.K. An external quantum efficiency at a brightness in the vicinity of 1,000 cd/$m^2$ was calculated based on the thus measured values according to the brightness conversion method. The evaluation results are shown in each table while defining the case where a reduction value of efficiency was less than 0.3% as "A", the case where the efficiency was reduced by 0.3% or more and less than 1.5% as "B" and the case where the efficiency was reduced by 1.5% or more "C", respectively on the basis of a value of a device using a material having a water content of not more than a detection limit (namely, Comparative Devices C1-1 to C22-1 shown in the uppermost row in the respective tables).

(b) Driving Durability:

Each of the devices was continuously subjected to light emission upon being impressed with a direct current voltage such that the brightness was 1,000 cd/$m^2$. A time T required until the brightness reached 500 cd/$m^2$ was evaluated. The evaluation results are shown in each table while defining the case where a ratio of the time T to that of the basis device was higher than 95% "A", the case where a ratio of the time T to that of the basis device was higher than 90% and not more than 95% as "B" and the case where a ratio of the time T to that of the basis device was not higher than 90% as "C", respectively on the basis of a value of a device using a material having a water content of not more than a detection limit (namely, Comparative Devices C1-1 to C22-1 shown in the uppermost row in the respective tables).

(c) Driving Voltage:

A voltage when each of the devices was impressed with a direct current voltage such that the brightness was 1,000 cd/$m^2$ was evaluated as a driving voltage. The evaluation results are shown in each table while defining the case where an elevation value was 0 V or more and less than 2 V as "A", the case where an elevation value was 0.2 V or more and less than 0.5 V as "B" and the case where an elevation value was 0.5 V or more as "C", respectively on the basis of a value of a device using a material having a water content of not more than a detection limit (namely, Comparative Devices C1-1 to C22-1 shown in the uppermost row in the respective tables).

(d) Number of Short-Circuit Devices:

Fifty devices (5×10 times vapor deposition within the same chamber) were prepared under the same condition, and each of the devices was impressed with a direct current voltage of from 0 V to 20 V using a source measure unit MODEL 2400, manufactured by Toyo Corporation. On that occasion, the number of devices which caused a short circuit and became non-light emitting was evaluated in terms of a percentage.

(e) Storage Stability (Presence or Absence of Cloudy Device by Visual Inspection):

Each of the devices was stored in a thermostat at 50° C. for 30 days. The evaluation results are shown in each table while defining the case where one or more devices wherein cloudiness could be confirmed by visual inspection were present as "B" and the case where any device wherein cloudiness could be confirmed by visual inspection was not present as "A", respectively.

TABLE 1

Example 1

Device configuration: ITO/CuPc (10)/NPD (30)/CBP + 8% Compound 1 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective | C1-1 | <5 ppm | Basis | Basis | Basis | 12% | B | Comparison |
| material: | C1-2 | 54 ppm | A | A | A | 10% | A | |
| Compound 1 | C1-3 | 70 ppm | A | A | A | 10% | B | |
| | C1-4 | 86 ppm | A | A | A | 12% | B | |
| | C1-5 | 95 ppm | A | A | A | 6% | A | |
| | 1-1 | 127 ppm | A | A | A | 4% | A | Invention |
| | 1-2 | 301 ppm | A | A | A | 2% | A | |
| | 1-3 | 457 ppm | A | A | A | 2% | A | |
| | 1-4 | 756 ppm | A | A | A | 0% | A | |
| | C1-6 | 1050 ppm | A | A | B | 2% | A | Comparison |
| | C1-7 | 1460 ppm | A | B | C | 6% | A | |
| | C1-8 | 2980 ppm | B | C | C | 14% | A | |

TABLE 2

Example 2

Device configuration: ITO/CuPc (10)/NPD (30)/CBP + 8% Compound 2 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective material: Compound 2 | C2-1 | <5 ppm | Basis | Basis | Basis | 10% | B | Comparison |
| | C2-2 | 30 ppm | A | A | A | 12% | B | |
| | C2-3 | 57 ppm | A | A | A | 12% | B | |
| | 2-1 | 103 ppm | A | A | A | 4% | B | Invention |
| | 2-2 | 390 ppm | A | A | A | 0% | A | |
| | 2-3 | 695 ppm | A | A | A | 4% | A | |
| | 2-4 | 940 ppm | A | A | A | 2% | A | |
| | C2-4 | 1200 ppm | A | B | C | 10% | A | Comparison |
| | C2-5 | 1940 ppm | A | B | C | 16% | A | |
| | C2-6 | 2600 ppm | A | C | C | 12% | A | |

TABLE 3

Example 3

Device configuration: ITO/CuPc (10)/NPD (30)/CBP + 8% Compound 12 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective material: Compound 12 | C3-1 | <5 ppm | Basis | Basis | Basis | 10% | B | Comparison |
| | C3-2 | 15 ppm | A | A | A | 10% | B | |
| | C3-3 | 51 ppm | A | A | A | 8% | B | |
| | 3-1 | 104 ppm | A | A | A | 4% | A | Invention |
| | 3-2 | 260 ppm | A | A | A | 2% | A | |
| | 3-3 | 680 ppm | A | A | A | 2% | A | |
| | 3-4 | 900 ppm | A | A | A | 4% | A | |
| | C3-4 | 1200 ppm | A | C | C | 6% | A | Comparison |
| | C3-5 | 2500 ppm | A | C | C | 2% | A | |
| | C3-6 | 3100 ppm | B | C | C | 6% | A | |

TABLE 4

Example 4

Device configuration: ITO/CuPc (10)/NPD (30)/CBP + 8% Compound 8 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective material: Compound 8 | C4-1 | <5 ppm | Basis | Basis | Basis | 18% | B | Comparison |
| | C4-2 | 10 ppm | A | A | A | 16% | B | |
| | C4-3 | 40 ppm | A | A | A | 16% | B | |
| | C4-4 | 68 ppm | A | A | A | 10% | A | |
| | C4-5 | 92 ppm | A | A | A | 12% | B | |
| | 4-1 | 115 ppm | A | A | A | 6% | A | Invention |
| | 4-2 | 360 ppm | A | A | A | 0% | A | |
| | 4-3 | 870 ppm | A | A | A | 4% | A | |
| | C4-6 | 1050 ppm | A | B | C | 8% | A | Comparison |
| | C4-7 | 2000 ppm | A | B | C | 8% | A | |
| | C4-8 | 3500 ppm | B | C | C | 12% | A | |

TABLE 5

Example 5

Device configuration:
ITO/CuPc (10)/NPD (30)/mCP + 8% Compound 9 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective | C5-1 | <5 ppm | Basis | Basis | Basis | 12% | B | Comparison |
| material: | C5-2 | 17 ppm | A | A | A | 10% | B | |
| Compound 9 | C5-3 | 80 ppm | A | A | A | 12% | B | |
| | 5-1 | 110 ppm | A | A | A | 6% | A | Invention |
| | 5-2 | 240 ppm | A | A | A | 4% | A | |
| | 5-3 | 595 ppm | A | A | A | 2% | A | |
| | 5-4 | 760 ppm | A | A | A | 2% | A | |
| | C5-4 | 1100 ppm | A | C | C | 2% | A | Comparison |
| | C5-5 | 1900 ppm | C | C | C | 6% | A | |
| | C5-6 | 2750 ppm | C | C | C | 16% | A | |
| | C5-7 | 3200 ppm | C | C | C | 14% | A | |

TABLE 6

Example 6

Device configuration:
ITO/CuPc (10)/NPD (30)/BAlq + 8% Compound 3 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective | C6-1 | <5 ppm | Basis | Basis | Basis | 10% | B | Comparison |
| material: | C6-2 | 35 ppm | A | A | A | 8% | B | |
| Compound 3 | C6-3 | 60 ppm | A | A | A | 8% | B | |
| | C6-4 | 84 ppm | A | A | A | 10% | A | |
| | 6-1 | 150 ppm | A | A | A | 4% | A | Invention |
| | 6-2 | 480 ppm | A | B | A | 4% | A | |
| | 6-3 | 900 ppm | A | A | A | 4% | A | |
| | C6-5 | 1800 ppm | B | B | C | 6% | A | Comparison |
| | C6-6 | 2700 ppm | C | C | C | 4% | A | |

TABLE 7

Example 7

Device configuration: ITO/CuPc (10)/NPD (30)/BAlq +
8% Compound 4 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective | C7-1 | <5 ppm | Basis | Basis | Basis | 8% | B | Comparison |
| material: | C7-2 | 10 ppm | A | A | A | 8% | B | |
| Compound 4 | C7-3 | 75 ppm | A | A | A | 10% | B | |
| | 7-1 | 145 ppm | A | A | A | 2% | A | Invention |
| | 7-2 | 360 ppm | A | A | A | 0% | A | |
| | 7-3 | 800 ppm | A | A | A | 2% | A | |
| | C7-4 | 1100 ppm | A | A | B | 4% | A | Comparison |
| | C7-5 | 2200 ppm | B | B | C | 10% | A | |
| | C7-6 | 4000 ppm | B | C | C | 8% | A | |

TABLE 8

Example 8

Device configuration: ITO/CuPc (10)/NPD (30)/BAlq + 8% Compound 5 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective | C8-1 | <5 ppm | Basis | Basis | Basis | 10% | B | Comparison |
| material: | C8-2 | 10 ppm | A | A | A | 8% | B | |
| Compound 5 | C8-3 | 65 ppm | A | A | A | 10% | B | |
| | 8-1 | 245 ppm | A | A | A | 2% | A | Invention |
| | 8-2 | 460 ppm | A | A | A | 0% | A | |
| | 8-3 | 830 ppm | A | A | A | 2% | B | |
| | C8-4 | 1200 ppm | A | A | B | 0% | A | Comparison |
| | C8-5 | 2100 ppm | B | B | C | 10% | A | |
| | C8-6 | 3700 ppm | B | C | C | 10% | A | |

TABLE 9

Example 9

Device configuration: ITO/CuPc (10)/NPD (30)/BAlq + 8% Compound 6 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective | C9-1 | <5 ppm | Basis | Basis | Basis | 8% | B | Comparison |
| material: | C9-2 | 10 ppm | A | A | A | 8% | B | |
| Compound 6 | C9-3 | 45 ppm | A | A | A | 8% | B | |
| | 9-1 | 150 ppm | A | A | A | 2% | A | Invention |
| | 9-2 | 380 ppm | A | A | A | 0% | B | |
| | 9-3 | 810 ppm | A | A | A | 0% | A | |
| | C9-4 | 1300 ppm | A | A | B | 6% | A | Comparison |
| | C9-5 | 2700 ppm | B | B | C | 8% | A | |
| | C9-6 | 3300 ppm | B | C | C | 12% | A | |

TABLE 10

Example 10

Device configuration: ITO/CuPc (10)/NPD (30)/BAlq + 8% Compound 7 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective | C10-1 | <5 ppm | Basis | Basis | Basis | 12% | B | Comparison |
| material: | C10-2 | 60 ppm | A | A | A | 10% | B | |
| Compound 7 | C10-3 | 83 ppm | A | B | A | 10% | B | |
| | 10-1 | 127 ppm | A | A | A | 4% | A | Invention |
| | 10-2 | 450 ppm | A | A | A | 4% | A | |
| | 10-3 | 950 ppm | A | A | A | 2% | A | |
| | C10-4 | 1600 ppm | B | C | C | 4% | A | Comparison |
| | C10-5 | 2450 ppm | B | C | C | 6% | A | |
| | C10-6 | 3000 ppm | B | C | C | 10% | A | |

TABLE 11

Example 11

Device configuration: ITO/CuPc (10)/NPD (30)/mCBP + 8% Compound 10 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective material: Compound 10 | C11-1 | <5 ppm | Basis | Basis | Basis | 8% | B | Comparison |
| | C11-2 | 14 ppm | A | A | A | 14% | B | |
| | C11-3 | 46 ppm | A | A | A | 12% | B | |
| | C11-4 | 87 ppm | A | A | A | 8% | A | |
| | 11-1 | 130 ppm | A | A | A | 4% | A | Invention |
| | 11-2 | 420 ppm | A | A | A | 2% | A | |
| | 11-3 | 645 ppm | A | A | A | 2% | A | |
| | C11-5 | 1300 ppm | A | B | C | 6% | A | Comparison |
| | C11-6 | 2900 ppm | A | C | C | 10% | A | |

TABLE 12

Example 12

Device configuration: ITO/CuPc (10)/NPD (30)/mCBP + 8% Compound 11 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective material: Compound 11 | C12-1 | <5 ppm | Basis | Basis | Basis | 8% | B | Comparison |
| | C12-2 | 16 ppm | A | A | A | 12% | B | |
| | C12-3 | 60 ppm | A | A | A | 12% | B | |
| | C12-4 | 84 ppm | A | A | A | 8% | A | |
| | 12-1 | 110 ppm | A | A | A | 4% | A | Invention |
| | 12-2 | 520 ppm | A | A | A | 4% | A | |
| | 12-3 | 700 ppm | A | A | A | 2% | A | |
| | C12-5 | 1100 ppm | A | B | C | 6% | A | Comparison |
| | C12-6 | 1900 ppm | A | C | C | 12% | A | |

TABLE 13

Example 13

Device configuration: ITO/CuPc (10)/NPD (30)/mCBP + 8% Compound 51 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective material: Compound 51 | C13-1 | <5 ppm | Basis | Basis | Basis | 6% | B | Comparison |
| | C13-2 | 40 ppm | A | A | A | 10% | B | |
| | C13-3 | 50 ppm | A | A | A | 12% | B | |
| | C13-4 | 96 ppm | A | A | A | 8% | B | |
| | 13-1 | 120 ppm | A | A | A | 4% | A | Invention |
| | 13-2 | 430 ppm | A | A | A | 2% | A | |
| | 13-3 | 690 ppm | A | A | A | 2% | A | |
| | C13-5 | 1300 ppm | A | C | C | 6% | A | Comparison |
| | C13-6 | 1600 ppm | A | C | C | 10% | B | |

TABLE 14

Example 14

Device configuration: ITO/CuPc (10)/NPD (30)/mCBP + 8% Compound 94 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective material: Compound 94 | C14-1 | <5 ppm | Basis | Basis | Basis | 10% | B | Comparison |
| | C14-2 | 30 ppm | A | A | A | 10% | B | |
| | C14-3 | 70 ppm | A | A | A | 12% | B | |
| | C14-4 | 85 ppm | A | A | A | 8% | B | |
| | 14-1 | 110 ppm | A | A | A | 2% | A | Invention |
| | 14-2 | 530 ppm | A | A | A | 2% | A | |
| | 14-3 | 720 ppm | A | A | A | 2% | A | |
| | C14-5 | 1500 ppm | A | C | C | 8% | A | Comparison |
| | C14-6 | 2100 ppm | A | C | C | 10% | B | |

TABLE 15

Example 15

Device configuration: ITO/CuPc (10)NPD (30)/mCBP + 8% Compound 95 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective material: Compound 95 | C15-1 | <5 ppm | Basis | Basis | Basis | 8% | B | Comparison |
| | C15-2 | 20 ppm | A | A | A | 8% | B | |
| | C15-3 | 40 ppm | A | A | A | 12% | B | |
| | C15-4 | 70 ppm | A | A | A | 10% | B | |
| | 15-1 | 140 ppm | A | A | A | 2% | A | Invention |
| | 15-2 | 690 ppm | A | A | A | 4% | A | |
| | 15-3 | 780 ppm | A | A | A | 2% | A | |
| | C15-5 | 1400 ppm | A | C | C | 10% | A | Comparison |
| | C15-6 | 2000 ppm | A | C | C | 12% | A | |

TABLE 16

Example 16

Device configuration: ITO/CuPc (10)NPD (30)/mCBP + 8% Compound 97 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective material: Compound 97 | C16-1 | <5 ppm | Basis | Basis | Basis | 6% | B | Comparison |
| | C16-2 | 30 ppm | A | A | A | 8% | B | |
| | C16-3 | 60 ppm | A | A | A | 10% | B | |
| | C16-4 | 70 ppm | A | A | A | 10% | B | |
| | 16-1 | 110 ppm | A | A | A | 2% | A | Invention |
| | 16-2 | 640 ppm | A | A | A | 2% | A | |
| | 16-3 | 720 ppm | A | A | A | 4% | A | |
| | C16-5 | 1100 ppm | A | C | C | 12% | A | Comparison |
| | C16-6 | 2300 ppm | A | C | C | 12% | A | |

TABLE 17

Example 17

Device configuration: ITO/CuPc (10)/NPD (30)/mCBP + 8% Compound 98 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective material: Compound 98 | C17-1 | <5 ppm | Basis | Basis | Basis | 6% | B | Comparison |
| | C17-2 | 50 ppm | A | A | A | 8% | B | |
| | C17-3 | 70 ppm | A | A | A | 8% | B | |
| | C17-4 | 80 ppm | A | A | A | 10% | B | |
| | 17-1 | 150 ppm | A | A | A | 2% | A | Invention |
| | 17-2 | 330 ppm | A | A | A | 4% | A | |
| | 17-3 | 590 ppm | A | A | A | 4% | A | |
| | C17-5 | 1600 ppm | A | C | C | 14% | A | Comparison |
| | C17-6 | 3100 ppm | A | C | C | 12% | A | |

TABLE 18

Example 18

Device configuration: ITO/CuPc (10)/NPD (30)/mCBP + 8% Compound 99 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective material: Compound 99 | C18-1 | <5 ppm | Basis | Basis | Basis | 6% | B | Comparison |
| | C18-2 | 20 ppm | A | A | A | 8% | B | |
| | C18-3 | 40 ppm | A | A | A | 6% | B | |
| | C18-4 | 60 ppm | A | A | A | 10% | B | |
| | 18-1 | 160 ppm | A | A | A | 2% | A | Invention |
| | 18-2 | 410 ppm | A | A | A | 2% | A | |
| | 18-3 | 750 ppm | A | A | A | 4% | A | |
| | C18-5 | 1900 ppm | A | C | C | 10% | A | Comparison |
| | C18-6 | 2700 ppm | C | C | C | 12% | A | |

TABLE 19

Example 19

Device configuration: ITO/CuPc (10)/NPD (30)/mCBP + 8% Compound 100 (30)/BAlq (10)/Alq (30)/LiF (0.1)/Al (100)

| | Device No. | Water content | Driving voltage | External quantum efficiency | Driving durability | Number of short-circuit devices | Storage stability | Remark |
|---|---|---|---|---|---|---|---|---|
| Objective material: Compound 100 | C19-1 | <5 ppm | Basis | Basis | Basis | 6% | B | Comparison |
| | C19-2 | 10 ppm | A | A | A | 8% | B | |
| | C19-3 | 20 ppm | A | A | A | 6% | B | |
| | C19-4 | 50 ppm | A | A | A | 8% | B | |
| | 19-1 | 260 ppm | A | A | A | 2% | A | Invention |
| | 19-2 | 350 ppm | A | A | A | 2% | A | |
| | 19-3 | 540 ppm | A | A | A | 4% | A | |
| | C19-5 | 1700 ppm | A | C | C | 10% | A | Comparison |
| | C19-6 | 2100 ppm | A | C | C | 12% | A | |

TABLE 20

| Example 20 | | | | | | | | |
|---|---|---|---|---|---|---|---|---|
| | Device configuration: ITO/CuPc (10)/NPD (30)/mCBP + 8% Compound 101 (30)/BAlq (10)/Alq (30)/LiF (0.1)/Al (100) | | | | | | | |
| | Device No. | Water content | Driving voltage | External quantum efficiency | Driving durability | Number of short-circuit devices | Storage stability | Remark |
| Objective material: Compound 101 | C20-1 | <5 ppm | Basis | Basis | Basis | 6% | B | Comparison |
| | C20-2 | 10 ppm | A | A | A | 8% | B | |
| | C20-3 | 20 ppm | A | A | A | 6% | B | |
| | C20-4 | 40 ppm | A | A | A | 4% | B | |
| | 20-1 | 160 ppm | A | A | A | 2% | A | Invention |
| | 20-2 | 230 ppm | A | A | A | 2% | A | |
| | 20-3 | 660 ppm | A | A | A | 2% | A | |
| | C20-5 | 2100 ppm | A | C | C | 8% | A | Comparison |
| | C20-6 | 5100 ppm | C | C | C | 12% | A | |

TABLE 21

| Example 21 | | | | | | | | |
|---|---|---|---|---|---|---|---|---|
| | Device configuration: ITO/CuPc (10)/NPD (30)/mCBP + 8% Compound 102 (30)/BAlq (10)/Alq (30)/LiF (0.1)/Al (100) | | | | | | | |
| | Device No. | Water content | Driving voltage | External quantum efficiency | Driving durability | Number of short-circuit devices | Storage stability | Remark |
| Objective material: Compound 102 | C21-1 | <5 ppm | Basis | Basis | Basis | 6% | B | Comparison |
| | C21-2 | 10 ppm | A | A | A | 12% | B | |
| | C21-3 | 30 ppm | A | A | A | 6% | B | |
| | C21-4 | 60 ppm | A | A | A | 10% | B | |
| | 21-1 | 360 ppm | A | A | A | 2% | A | Invention |
| | 21-2 | 430 ppm | A | A | A | 2% | A | |
| | 21-3 | 650 ppm | A | A | A | 2% | A | |
| | C21-5 | 3300 ppm | C | C | C | 8% | A | Comparison |
| | C21-6 | 4700 ppm | C | C | C | 10% | A | |

TABLE 22

| Example 22 | | | | | | | | |
|---|---|---|---|---|---|---|---|---|
| | Device configuration: ITO/CuPc (10)/NPD (30)/mCBP + 8% Compound 103 (30)/BAlq (10)/Alq (30)/LiF (0.1)/Al (100) | | | | | | | |
| | Device No. | Water content | Driving voltage | External quantum efficiency | Driving durability | Number of short-circuit devices | Storage stability | Remark |
| Objective material: Compound 103 | C22-1 | <5 ppm | Basis | Basis | Basis | 6% | B | Comparison |
| | C22-2 | 10 ppm | A | A | A | 12% | B | |
| | C22-3 | 50 ppm | A | A | A | 10% | B | |
| | C22-4 | 60 ppm | A | A | A | 8% | B | |
| | 22-1 | 260 ppm | A | A | A | 2% | A | Invention |
| | 22-2 | 480 ppm | A | A | A | 2% | A | |
| | 22-3 | 850 ppm | A | A | A | 2% | A | |
| | C22-5 | 4300 ppm | C | C | C | 10% | A | Comparison |
| | C22-6 | 5700 ppm | C | C | C | 10% | A | |

Figure 4:
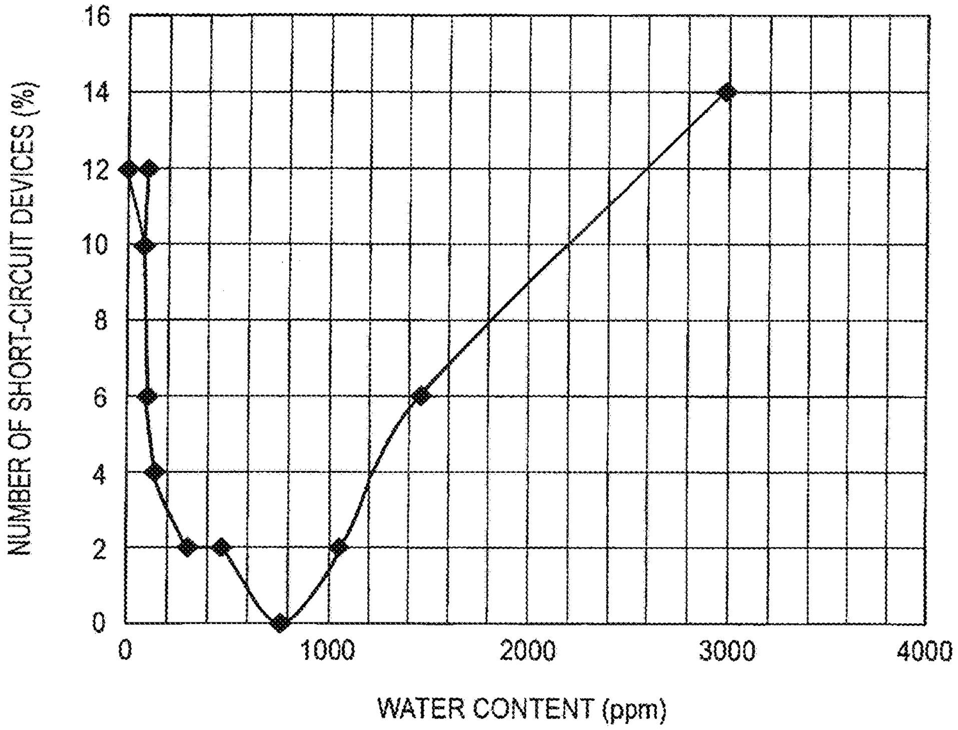
FIG. 4 is a graph showing a relation between a water content (ppm) of a material for organic electroluminescence device according to the invention and the number of short-circuit devices (%) in the obtained devices.

From the results of Table 1, a relation between a water content (ppm) (abscissa) of Compound 1 as the objective material of Example 1 and the number of short-circuit devices (%) in the devices obtained using the subject material is shown in a graph of FIG. 4.

From the results of Tables 1 to 22, it is understood that by using the material having a water content before film formation of from 100 to 1,000 ppm, the devices of the invention are excellent in external quantum efficiency and driving durability and are able to reduce the number of short-circuit devices without dropping device characteristics and to enhance yields, as compared with the devices of the Comparative Examples. In particular, the devices of the Comparative Examples using a material having a water content before film formation of less than 100 ppm are not preferable because the number of short-circuit devices increases. Also, it is understood that the devices of the Comparative Examples using a material having a water content before film formation exceeding 1,000 ppm are inferior in external quantum efficiency and driving durability to the devices of the invention. Also, it is understood that in the devices of the invention, cloudiness that may be estimated to be caused due to crystallization of a fine material can be suppressed so that a device with excellent storage stability can be provided.

Also, the device of the invention is suitable for a light emission apparatus, a display apparatus and an illumination apparatus.

Structures of the compounds used in the foregoing Examples and Comparative Examples are shown below.

1

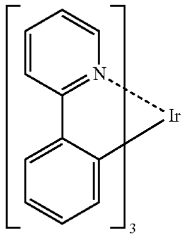

2

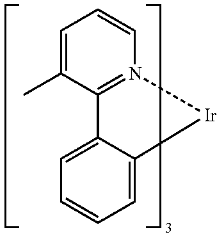

3

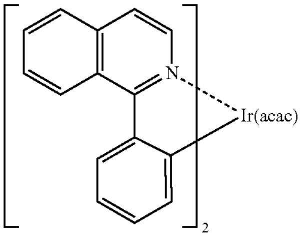

4

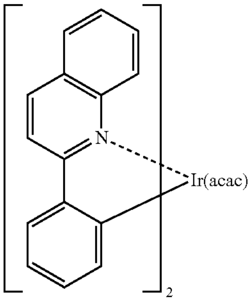

-continued

5

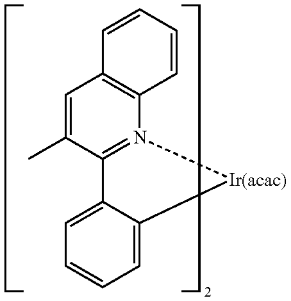

6

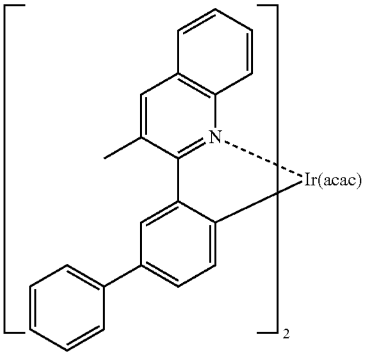

7

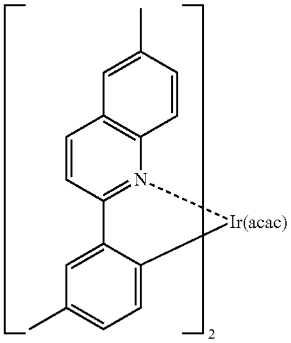

8

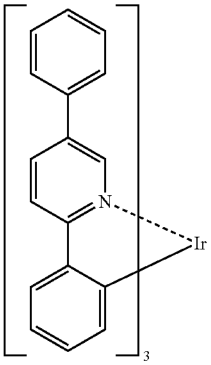

-continued
9
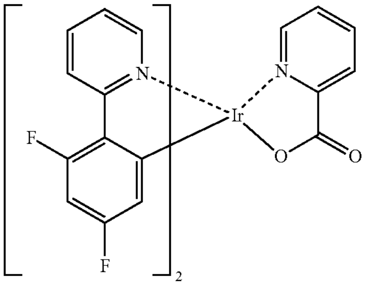
10
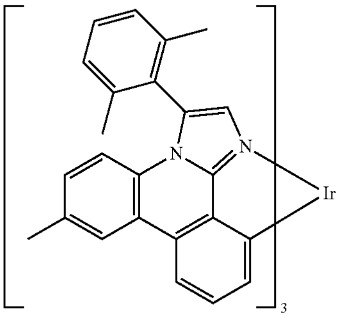
11
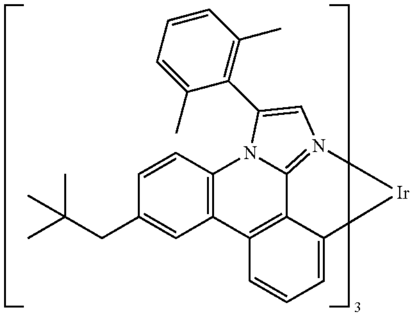
12
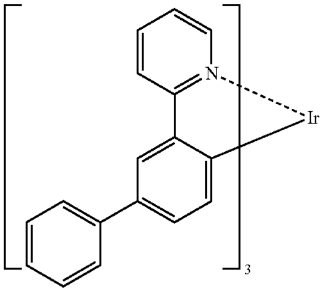
51
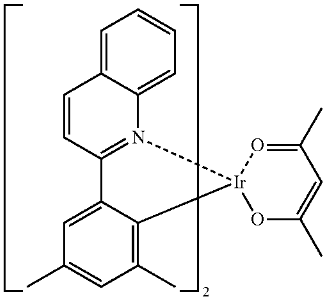
-continued
94
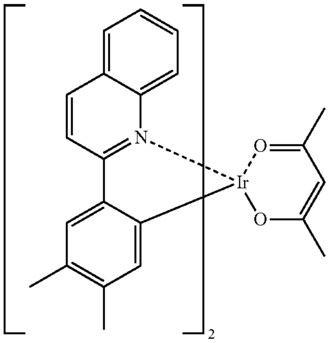
95
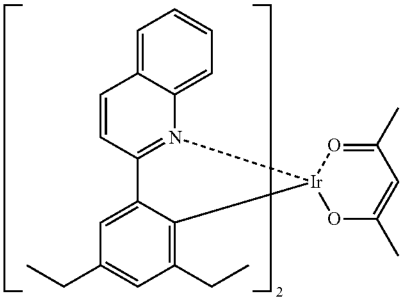
97
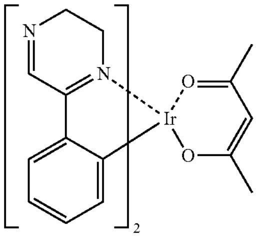
98
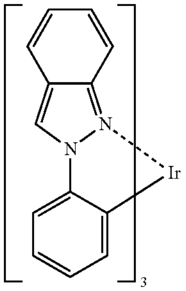
99
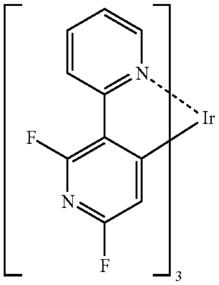

-continued
100
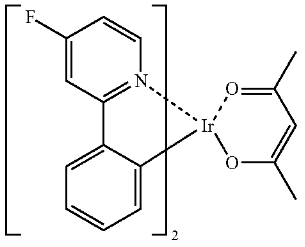
101
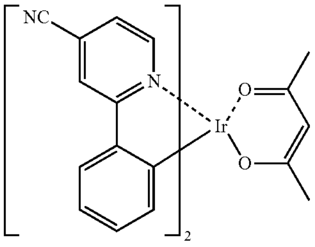
102
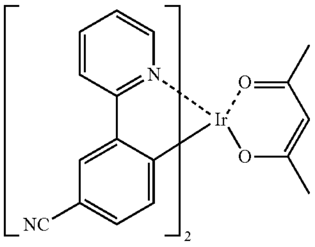
103
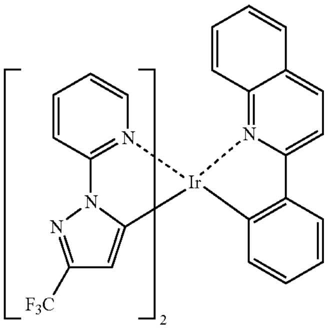
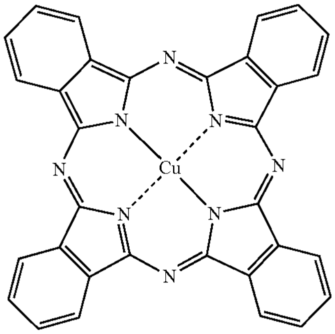
CuPc
-continued
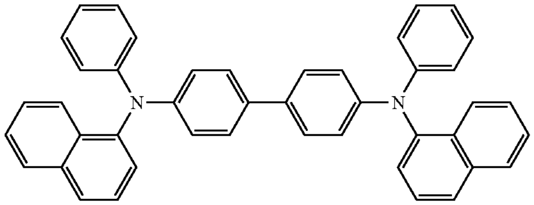
NPD
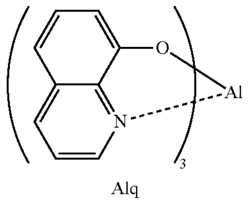
Alq
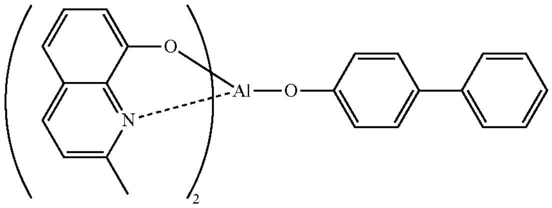
BAlq
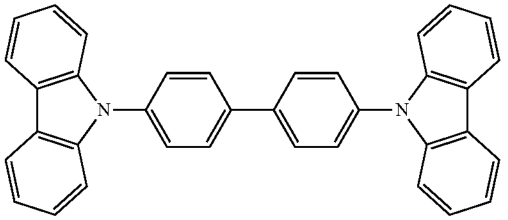
CBP
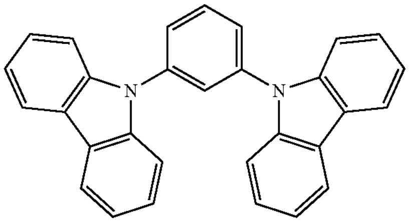
mCP
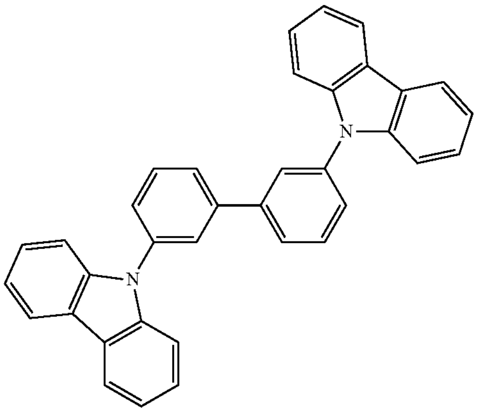
mCBP
According to the material for organic electroluminescence device of the invention, it is possible to obtain an organic electroluminescence device with excellent light emitting characteristics and to reduce the number of short-circuit devices, thereby enhancing the productivity.

The organic electroluminescence device of the invention is small in power consumption, has a high external quantum efficiency and is excellent in driving durability and storage durability.

This application is based on Japanese patent application Nos. 2009-201159 filed on Aug. 31, 2009, 2009-223453 filed on Sep. 28, 2009, and 2010-100396 filed on Apr. 23, 2010, the entire content of which is hereby incorporated by reference, the same as if set forth at length.

What is claimed is:

1. A material in a solid state, said material being for an organic electroluminescence device, comprising:

an organometallic compound that is to be provided for a dry film formation process of any of at least one layer included in the electroluminescence device, wherein the material has a water content before the dry film formation process, as measured by the Karl Fischer method, of 100 ppm or more and not more than 1,000 ppm, wherein the organometallic compound is an iridium complex represented by the following formula (E-3):

(E-3)

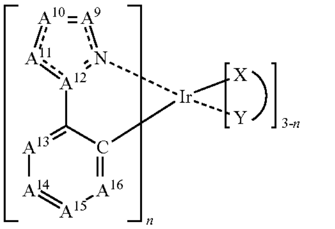

in the formula (E-3), each of $A^9$ to $A^{11}$ and $A^{13}$ to $A^{16}$ independently represents C—R, N or N—R';

$A^{12}$ represents a carbon atom or a nitrogen atom;

R represents a hydrogen atom, an alkyl group, an aryl group, an aromatic heterocyclic group, a cyano group, a silyl group, an amino group or a fluorine atom;

R' represents a hydrogen atom, an alkyl group or an aryl group;

n represents an integer of from 1 to 3; and

X—Y represents a monoanionic bidentate ligand represented by the following formula (I-1), (I-2) or (I-3):

(I-1)

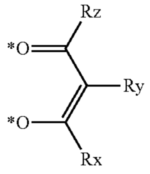

(I-2)

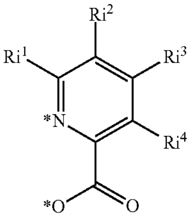

-continued (I-3)

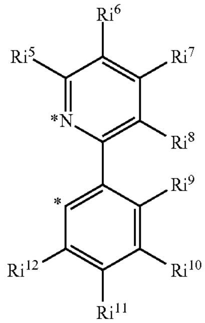

in the formula (I-1), each of Rx and Rz independently represents an alkyl group, a perfluoroalkyl group or an aryl group; and Ry represents a hydrogen atom, an alkyl group, a perfluoroalkyl group or an aryl group, in the formula (I-2), each of $Ri^1$ to $Ri^4$ independently represents a hydrogen atom, an alkyl group, a perfluoroalkyl group, an aryl group, an alkoxy group, an aryloxy group, a dialkylamino group, a diarylamino group, a cyano group, a fluorine atom, a trialkylsilyl group, a triarylsilyl group, an alkyldiarylsilyl group, a dialkylarylsilyl group, a heterocyclic group or a heterocyclic oxy group; and adjacent substituents among $Ri^1$ to $Ri^4$ may be connected to each other, and in the formula (I-3), each of $Ri^5$ to $Ri^{12}$ independently represents a hydrogen atom, an alkyl group, a perfluoroalkyl group, an aryl group, an alkoxy group, an aryloxy group, a dialkylamino group, a diarylamino group, a cyano group, a fluorine atom, a trialkylsilyl group, a triarylsilyl group, an alkyldiarylsilyl group, a dialkylarylsilyl group, a heterocyclic group or a heterocyclic oxy group; and adjacent substituents among $Ri^5$ to $Ri^8$, adjacent substituents among $Ri^9$ to $Ri^{12}$, and $Ri^8$ and $Ri^9$ may be each connected to each other.

2. The material for an organic electroluminescence device according to claim 1, wherein the iridium complex represented by the formula (E-3) is represented by the following formula (E-4):

(E-4)

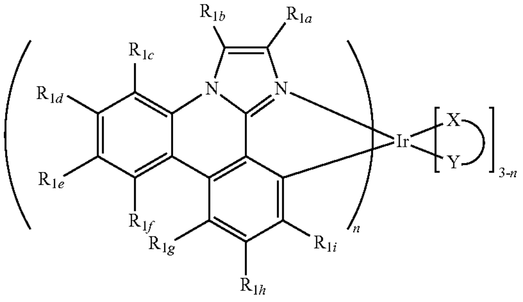

in the formula (E-4), each of $R_{1a}$ to $R_{1i}$ independently represents a hydrogen atom, an alkyl group, an aryl group, an aromatic heterocyclic group, a cyano group, a silyl group, an amino group or a fluorine atom;

X—Y is synonymous with X—Y in the formula (E-3); and n represents an integer of from 1 to 3.

3. The material for an organic electroluminescence device according to claim 2, wherein in the formula (E-4), n is 3.

4. A material in a solid state, said material being for an organic electroluminescence device, comprising:

an organometallic compound that is to be provided for a dry film formation process of any of at least one organic layer included in the electroluminescence device, wherein the material has a water content before the dry film formation process, as measured by the Karl Fischer method, of 100 ppm or more and not more than 1,000 ppm, wherein the organometallic compound is an iridium complex represented by the following formula (PQ-1):

(PQ-1)

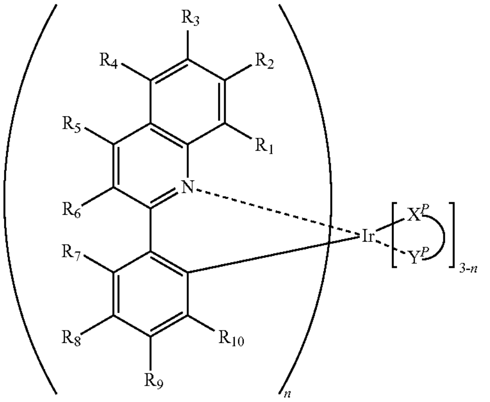

in the formula (PQ-1), each of $R_1$ to $R_{10}$ independently represents a hydrogen atom, an alkyl group, an aryl group, an aromatic heterocyclic group, a cyano group, a silyl group, an amino group or a fluorine atom;

$R_1$ to $R_{10}$ may be bonded to each other to form a ring, if possible;

n is 2; and $X^P—Y^P$ is a monoanionic bidentate ligand represented by the following formula L:

Formula L

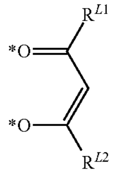

in the formula L, each of $R^{L1}$ and $R^{L2}$ independently represents an alkyl group having from 1 to 5 carbon atoms or a phenyl group which may have a substituent selected from the substituent group T2 consisting of an alkyl group having from 1 to 6 carbon atoms, an alkenyl group having from 2 to 6 carbon atoms, a phenyl group, and aromatic heterocyclic group having from 5 to 10 carbon atoms, an alkoxy group having from 1 to 4 carbon atoms, a phenoxy group, a fluorine atom, a silyl group, an amino group, a cyano group and a group composed of a combination of these groups; and plural substituents selected from the substituent group T2 may be joined or fused to each other to form a ring.

5. A composition in a solid state that is to be provided for a dry film formation process, comprising:

the material for an organic electroluminescence device according to claim 1.

6. The composition according to claim 5, further comprising:

a compound represented by the following formula (4-1) or (4-2):

Formula (4-1)

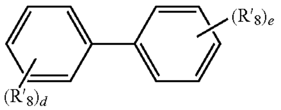

Formula (4-2)

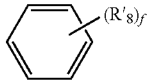

in the formulae (4-1) and (4-2), each of d and e independently represents an integer of from 0 to 3, and at least one of d and e is 1 or more;

f represents an integer of from 1 to 4;

$R'_8$ represents an alkyl group, an aryl group, a heteroaryl group, a fluorine atom, a cyano group, an alkoxy group, an aryloxy group, an amino group or a silyl group, and when plural $R'_8$s are present, each $R'_8$ may be the same as or different from every other $R'_8$; and at least one of $R'_8$s represents a group represented by the following formula (5):

(5)

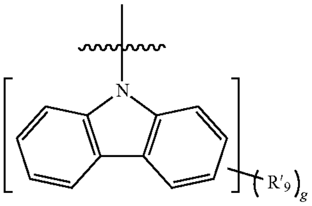

in the formula (5), each of $R'_9$s independently represents an alkyl group, an aryl group, a heteroaryl group, a fluorine atom, a cyano group, an alkoxy group, an aryloxy group, an amino group or a silyl group; and g represents an integer of from 0 to 8.

7. A method for manufacturing an organic electroluminescence device, comprising: forming a layer comprising the material for an organic electroluminescence device according to claim 1.

8. A method for reducing a rate of occurrence of short-circuit device, comprising: forming a layer comprising the material for an organic electroluminescence device according to claim 1.

9. A composition in a solid state that is to be provided for a dry film formation process, comprising:

the material for an organic electroluminescence device according to claim 4.

* * * * *